US011192894B2

(12) United States Patent
Hall et al.

(10) Patent No.: US 11,192,894 B2
(45) Date of Patent: *Dec. 7, 2021

(54) CELL IMPERMEABLE COELENTERAZINE ANALOGUES

(71) Applicant: PROMEGA CORPORATION, Madison, WI (US)

(72) Inventors: Mary Hall, Waunakee, WI (US); Thomas Kirkland, Atascadero, CA (US); Poncho Meisenheimer, San Luis Obispo, CA (US); Rachel Friedman Ohana, Madison, WI (US); Anton Shakhmin, Santa Clara, CA (US); Joel R. Walker, San Luis Obispo, CA (US); Wenhui Zhou, San Luis Obispo, CA (US)

(73) Assignee: PROMEGA CORPORATION, Madison, WI (US)

( * ) Notice: Subject to any disclaimer, the term of this patent is extended or adjusted under 35 U.S.C. 154(b) by 14 days.

This patent is subject to a terminal disclaimer.

(21) Appl. No.: 16/725,602

(22) Filed: Dec. 23, 2019

(65) Prior Publication Data

US 2020/0239475 A1 Jul. 30, 2020

Related U.S. Application Data

(63) Continuation of application No. 15/829,262, filed on Dec. 1, 2017, now Pat. No. 10,577,370.

(60) Provisional application No. 62/477,512, filed on Mar. 28, 2017, provisional application No. 62/428,997, filed on Dec. 1, 2016.

(51) Int. Cl.
*C07D 487/04* (2006.01)
*G01N 33/58* (2006.01)
*C12Q 1/66* (2006.01)

(52) U.S. Cl.
CPC .......... *C07D 487/04* (2013.01); *C12Q 1/66* (2013.01); *G01N 33/581* (2013.01); *G01N 2333/90241* (2013.01)

(58) Field of Classification Search
CPC .......... A61K 2121/00; A61K 2123/00; C07D 487/04; G01N 33/581; G01N 2333/90241; C12Q 1/66
USPC .... 424/1.11, 1.65, 1.81, 1.85, 1.89, 9.1, 9.2, 424/9.3, 9.4, 9.5, 9.6
See application file for complete search history.

(56) References Cited

U.S. PATENT DOCUMENTS

| | | | |
|---|---|---|---|
| 8,557,970 B2 | 10/2013 | Encell et al. | |
| 8,669,103 B2 | 3/2014 | Binkowski et al. | |
| 8,809,529 B2 | 8/2014 | Klaubert et al. | |
| 9,790,537 B2 | 10/2017 | Zhou et al. | |
| 9,924,073 B2 | 3/2018 | Shakhmin et al. | |
| 9,927,430 B2 | 3/2018 | Zhou et al. | |
| 9,938,564 B2 | 4/2018 | Klaubert et al. | |
| 10,000,500 B2 * | 6/2018 | Hall | C07D 519/00 |
| 10,280,447 B2 * | 5/2019 | Hall | C07D 487/04 |
| 10,308,975 B2 * | 6/2019 | Shakhmin | H04N 1/6041 |
| 10,428,075 B2 * | 10/2019 | Hall | C07D 519/00 |
| 10,577,370 B2 * | 3/2020 | Hall | C07D 487/04 |
| 2008/0248511 A1 | 10/2008 | Daily et al. | |
| 2011/0275134 A1 | 11/2011 | Bouvier et al. | |
| 2012/0107849 A1 | 5/2012 | Klaubert et al. | |
| 2012/0117667 A1 | 5/2012 | Klaubert et al. | |
| 2013/0130289 A1 | 5/2013 | Benink et al. | |
| 2013/0230466 A1 | 9/2013 | Hermanson et al. | |
| 2016/0376568 A1 | 12/2016 | Duellman et al. | |
| 2018/0119200 A1 | 5/2018 | Hall et al. | |
| 2018/0334463 A1 | 11/2018 | Hall et al. | |

FOREIGN PATENT DOCUMENTS

| | | |
|---|---|---|
| WO | WO 2003/040100 | 5/2003 |
| WO | WO 2012/061530 | 5/2012 |
| WO | WO 2013/078244 | 5/2013 |

OTHER PUBLICATIONS

Adamczyk et al., "Synthesis of 3,7-dihydroimidazo[1,2a]pyrazine-3-ones and their chemiluminescent properties," Tetrahedron, 2003, vol. 59, No. 41, pp. 8129-8142.
Chou et al., *Heterocycles*, vol. 86, No. 2, 2012, pp. 1323-1339 (2012).
Cross et al., "IUPAC Commission on Nomeclature of Organic Chemistry. Rules for the Nomeclature of Organic Chemistry. Section E: Stereochemistry (Recommendations 1974)," Pure & Appl. Chem., 1976, vol. 45 pp. 13-30.
Hall et al., "Engineered Luciferase Reporter from a Deep Sea Shrimp Utilizing a Novel Imidazopyrazinone Substrate," ACS Chemical Biology, 2012, vol. 7, No. 11, pp. 1848-1857.
Hirayama et al., "Fluorogenic probes reveal a role of GLUT4 N-glycosylation in intracellular trafficking," Nature Chemical Biology, 2016, vol. 12, pp. 853-859.
Kojima et al., "Rational Design and Development of Near-Infrared-Emitting Firefly Luciferins Available In Vivo," Angewandte Chemie International Edition, 2013, 52: 1175-1179.
Larock, Comprehensive Organic Transformations, VCH Publishers, Inc., New York, 1989.
Lavis et al., "Bright Building Blocks for Chemical Biology," ACS Chemical Biology, 2014, 9, 855-866.
Lindberg et al., "Development of cell-impermeable coelenterazine derivatives," Chemical Science, 2013, 4(12): 4395-4400.
International Search Report and Written Opinion for Application No. PCT/US2017/059495 dated Feb. 12, 2018 (14 pages).
Invitation to Pay Additional Fees for Application No. PCT/US2017/064229 dated Mar. 13, 2018 (13 pages).

(Continued)

*Primary Examiner* — D. L. Jones

(74) *Attorney, Agent, or Firm* — Casimir Jones, S.C.

(57) ABSTRACT

Described are coelenterazine analogues, methods for making the analogues, kits comprising the analogues, and methods of using the compounds for the detection of luminescence in luciferase-based assays.

36 Claims, 13 Drawing Sheets

Specification includes a Sequence Listing.

(56) References Cited

OTHER PUBLICATIONS

International Search Report and Written Opinion for Application No. PCT/US2017/064229 dated May 16, 2018 (18 pages).
United States Patent Office Action for U.S. Appl. No. 15/800,649 dated Jun. 18, 2018 (20 pages).

* cited by examiner

JRW-0769 / 40x / EM400 / 2.5 sec

Furimazine / 40x / EM400 / 0.5 sec

SEQUENCE LISTING

<160> NUMBER OF SEQ ID NOS: 2

<210> SEQ ID NO 1

<211> LENGTH: 169
<212> TYPE: PRT
<213> ORGANISM: Artificial
<220> FEATURE:
<223> OTHER INFORMATION: Synthetic Peptide

<400> SEQUENCE: 1

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ala Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

Gly Thr Leu Trp Asn Gly Asn Lys Ile Tyr Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165

<210> SEQ ID NO 2
<211> LENGTH: 171
<212> TYPE: PRT
<213> ORGANISM: Artificial
<220> FEATURE:
<223> OTHER INFORMATION: Synthetic Peptide

<400> SEQUENCE: 2

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val

| 145 | | | 150 | | | 155 | | | 160 | |
|---|---|---|---|---|---|---|---|---|---|---|
| Thr | Gly | Trp | Arg | Leu | Cys | Glu | Arg | Ile | Leu | Ala |
| | | | | 165 | | | 170 | | | |

CELL IMPERMEABLE COELENTERAZINE ANALOGUES

CROSS-REFERENCE TO RELATED APPLICATIONS

This application is a continuation of U.S. patent application Ser. No. 15/829,262, filed on Dec. 1, 2017, now U.S. Pat. No. 10,577,370, issued on Mar. 3, 2020, which claims priority to U.S. Provisional Patent Application No. 62/428,997, filed on Dec. 1, 2016, and U.S. Provisional Patent Application No. 62/477,512, filed on Mar. 28, 2017, the entire contents of each of which are incorporated herein by reference.

TECHNICAL FIELD

The present disclosure relates to coelenterazine analogues, methods for making coelenterazine analogues, and methods of using coelenterazine analogues in luciferase-based assays.

BACKGROUND

Bioluminescent assays are used extensively in the investigation of cellular physiology, especially processes associated with gene expression. In particular, luciferase reporter enzymes are quite valuable tools in this field, and, to date, there has been intense protein engineering to obtain small and environmentally insensitive luciferases that may be useful in bioluminescent assays. There exist a number of efficient luciferase reporters enabling whole-cell biosensor measurements, drug discovery through high-throughput screening, and in vivo imaging, which also permits the study of protein-protein interactions in living cells, apoptosis, and cell viability. Luciferases that use coelenterazine and coelenterazine analogues as substrates are among the most widely used systems due to their brightness and acceptance in whole cell applications.

SUMMARY OF THE INVENTION

There is great interest in bioluminescence imaging of cell surfaces and monitoring exocytotic events such as luciferase-fusion protein secretion, quantifying receptor recycling, cellular uptake or trafficking, neurotransmitter release, study of synaptic and vesicle release, etc. However, many known coelenterazine and coelenterazine analogues are highly cell permeable, and as such, selectively observing cell surface or extracellular events is currently not possible. Current methods for monitoring or imaging exocytotic events are limited and some require expensive equipment. Accordingly, there exists a need for cell impermeable coelenterazine analogues and methods for synthesizing the analogues.

The disclosed compounds may include a coelenterazine analog core, a covalent chain linker, and a polar group. The coelenterazine analog core may bind to a luciferase at the enzyme's binding site. The covalent chain may extend out of the enzyme's binding pocket such that the polar group diminishes the membrane permeability of the coelenterazine analog. The disclosed compounds thus are structurally distinctive from the conventional luciferase substrates in that the luciferase substrate core is covalently attached to a functional group, which may provide additional solubility and alter the permeability of the substrate. Yet, the disclosed compounds unexpectedly maintain the luciferase substrate activities that emit bioluminescence while simultaneously displaying reduced cell permeability.

In one aspect, disclosed are compounds of formula (I),

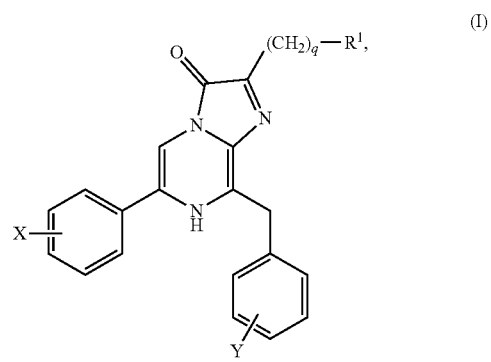

or a tautomer, or a pharmaceutically acceptable salt thereof, wherein

X and Y are independently absent, hydroxy, amino, —$COOR^2$, —$SO_2$—$OR^3$, —$PO(OR^4)(OR^5)$, or —O—$(CR^{1a}R^{1b})_m$—Z;

$R^1$ is optionally substituted aryl, optionally substituted heteroaryl, optionally substituted heterocycle, or optionally substituted cycloalkyl, provided that when both X and Y are absent, $R^1$ is substituted at least with -Q-L-Z;

Z at each occurrence is independently —$COOR^2$, —$SO_2$—$OR^3$, —$PO(OR^4)(OR^5)$, halogen, —$NR^6R^7$, or —$NR^8$—CO—$R^9$;

Q is —O—, —$NR^Q$—, —$NR^Q$—CO—, —CO—$NR^Q$—, —O—CO—$NR^Q$—, or —$NR^Q$—CO—O—;

L is —$(CR^{1a}R^{1b})_m$— or —$(CR^{1x}R^{1y}$—$CR^{1x}R^{1y}$—O$)_{t1}$—$(CR^{1x}R^{1y})_{t2}$-$Q^1$-, wherein $Q^1$ is absent, —O—, or —$NR^{Q1}$—;

$R^2$, $R^3$, $R^4$, $R^5$, $R^8$, and $R^9$ at each occurrence are independently hydrogen, optionally substituted $C_1$-$C_8$ alkyl, optionally substituted aryl, optionally substituted cycloalkyl, optionally substituted heteroaryl, or optionally substituted heterocycle;

$R^6$ and $R^7$ at each occurrence are independently hydrogen, optionally substituted $C_1$-$C_8$ alkyl, optionally substituted aryl, optionally substituted cycloalkyl, optionally substituted heteroaryl, or optionally substituted heterocycle; or $R^6$ and $R^7$, together with the nitrogen atom to which they are attached, together form an optionally substituted ring;

$R^{1a}$, $R^{1b}$, $R^Q$, $R^{Q1}$, $R^{1x}$, and $R^{1y}$ at each occurrence are independently hydrogen, $C_1$-$C_4$ alkyl, or $C_1$-$C_4$ haloalkyl;

q is 0, 1, or 2;

m at each occurrence is independently 1-12;

t1 is 1-10; and t2 is 0-5.

Also disclosed are methods of making the compounds, kits comprising the compounds, and methods of using the compounds as luciferase substrates in luciferase-based luminescence assays.

BRIEF DESCRIPTION OF THE DRAWINGS

FIG. 2A shows the RLU data with 10 µM substrate and ±20 µM JRW-0344 in the NanoLuc:KDR construct. Larger differences in RLU's are observed between substrates±inhibitor with the substrates containing a sulfonate group (JRW-0703, JRW-0728, JRW-0769). Small differences in RLU's are observed between substrates±inhibitor when the substrates contain an amine (TAK-0039), a carboxylate (JRW-0684), or a bromide (JRW-0720). FIG. 2B shows no significant differences in percent inhibition by the NANOLUC® inhibitor JRW-0344 using 10 µM and 20 µM substrate. FIG. 2C shows the RLU data with 10 µM substrate and ±20 µM JRW-0344 in the KDR:NanoLuc construct. The sulfonated, extracellular substrates (JRW-0703, JRW-0728, JRW-0769) are much dimmer and can be inhibited close to background level with the extracellular inhibitor. However, RLU's from cell permeable substrates (TAK-0039, JRW-0684, JRW-0720) are not affected by the extracellular inhibitor. FIG. 2D shows no significant differences in percent inhibition by the NANOLUC® inhibitor JRW-0344 using 10 µM and 20 µM substrate.

FIG. 3D shows the highest of the three concentrations for each substrate plotted by 'live' and 'lytic' formats for each compound, again comparing and contrasting cell permeable and non-cell permeable substrates.

FIG. 4A shows that Nluc-B2AR with JRW-0769 is limited to membrane-localized receptor (white arrows). FIG. 4B shows, in contrast imaging with furimazine, intracellular Nluc-B2AR (perinuclear structures, red arrows).

DETAILED DESCRIPTION

Figure 1A:
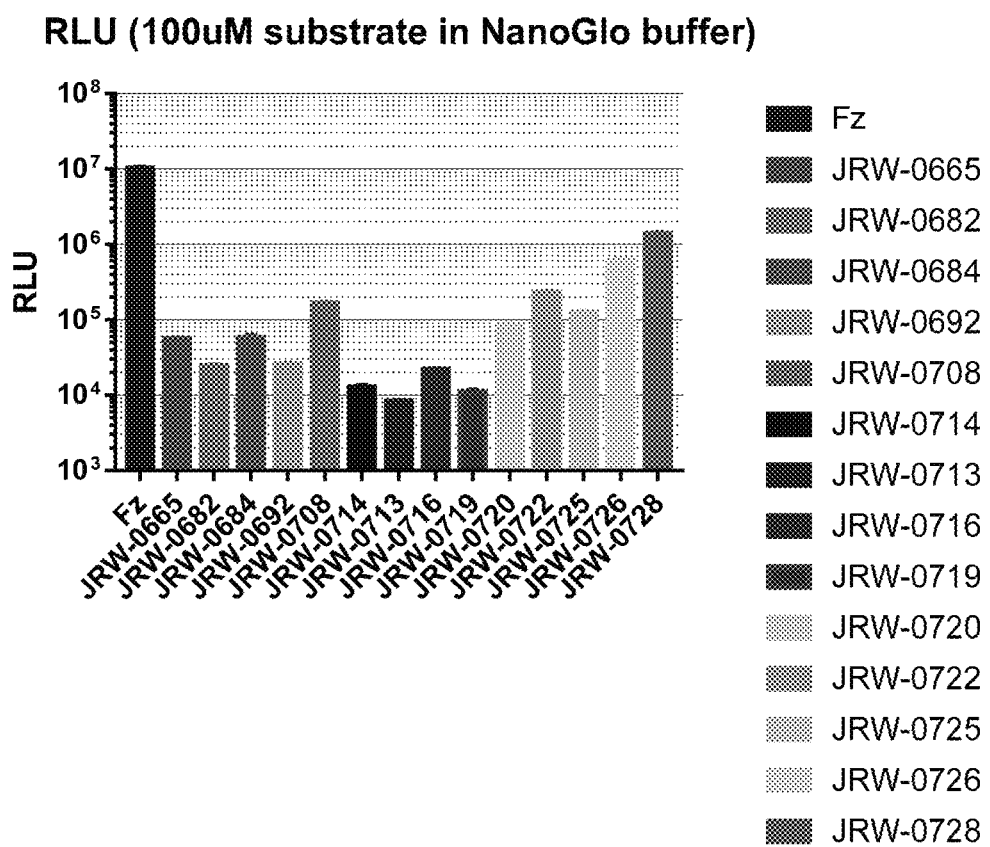
FIGS. 1A-1C show cellular bioluminescent activity of exemplary compounds in a biochemical format in comparison to furimazine (Fz).

Disclosed herein are coelenterazine analogues. The disclosed compounds may include a coelenterazine analog core, a covalent chain linker, and a polar group. The coelenterazine analog core may bind to a luciferase at the enzyme's binding site. The covalent chain may extend out of the enzyme's binding pocket such that the polar group diminishes the cell membrane permeability of the coelenterazine analog. The disclosed compounds thus are structurally distinctive from the conventional luciferase substrates in that the luciferase substrate core is covalently tethered to a polar group. The disclosed compounds unexpectedly maintain the luciferase substrate activities that emit bioluminescence while simultaneously allowing for reduced cell membrane permeability of the coelenterazine analog.

The coelenterazine analogues can be compounds of formula (I) and useful substrates of proteins that utilize coelenterazine to produce luminescence including, but not limited to, luciferases and photoproteins found in various marine organisms such as cnidarians (e.g., *Renilla* luciferase), jellyfish (e.g., aequorin from the *Aequorea* jellyfish) and decapods luciferases (e.g., luciferase complex of *Oplophorus gracilirostris*). The disclosed coelenterazine analogues may be tethered to a variety of polar groups by a stable linker. The polar group may be capable of diminishing the cell membrane permeability of the coelenterazine analog, thus enabling bioluminescence imaging of extracellular and cell surface events.

Also disclosed herein are methods of making the disclosed compounds. The described methodology enables access to coelenterazines tethered to a variety of polar groups and can be performed under mild conditions utilizing a wide variety of readily available starting materials. The disclosed synthetic methodology unexpectedly provides a variety of new applications and advancements in bioluminescence technology based on coelenterazine analogues.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a hydrocarbon chain containing from 2 to 10 carbon atoms with at least one carbon-carbon double bond. The alkenyl group may be substituted or unsubstituted. For example, the alkenyl group may be substituted with an aryl group, such as a phenyl.

The term "alkynyl" as used herein, means a hydrocarbon chain containing from 2 to 10 carbon atoms with at least one carbon-carbon triple bond. The alkynyl group may be substituted or unsubstituted. For example, the alkynyl group may be substituted with an aryl group, such as a phenyl.

The term "alkoxyalkyl" as used herein, refers to an alkoxy group, as defined herein, appended to the parent molecular moiety through an alkyl group, as defined herein.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "aryl" as used herein, refers to a phenyl group, or bicyclic aryl or tricyclic aryl fused ring systems. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl. The monocyclic, bicyclic, and tricyclic aryls are connected to the parent molecular moiety through any carbon atom contained within the rings, and can be unsubstituted or substituted.

The term "cycloalkyl" as used herein, refers to a carbocyclic ring system containing three to ten carbon atoms and zero heteroatoms, and optionally containing 1 or 2 double bonds. Representative examples of cycloalkyl include, but are not limited to, cyclopropyl, cyclobutyl, cyclopentyl, cyclohexyl, cycloheptyl, cyclooctyl, cyclononyl and cyclodecyl.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "alkoxyfluoroalkyl" as used herein, refers to an alkoxy group, as defined herein, appended to the parent molecular moiety through a fluoroalkyl group, as defined herein.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" or "halo" as used herein, means Cl, Br, I, or F.

The term "haloalkyl" as used herein, means an alkyl group, as defined herein, in which one, two, three, four, five, six, seven or eight hydrogen atoms are replaced by a halogen.

The term "haloalkoxy" as used herein, means at least one haloalkyl group, as defined herein, is appended to the parent molecular moiety through an oxygen atom.

The term "heteroalkyl" as used herein, means an alkyl group, as defined herein, in which one or more of the carbon atoms has been replaced by a heteroatom selected from S, Si, O, P, and N. The heteroatom may be oxidized. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O, and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a monocyclic heteroaryl ring appended to the parent molecular moiety and fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings, and can be unsubstituted or substituted.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4(1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3] heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "hydroxy" as used herein, means an —OH group.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The term "bioluminescence" or "luminescence" may refer to light produced as a result of a reaction between an enzyme and a substrate that generates light. Examples of such enzymes (bioluminescent enzymes) include Oplophorus luciferase, e.g., *Oplophorus gracilirostris*, firefly luciferase, e.g. *Photinus pyralis* or *Photuris pennsylvanica*, click beetle luciferase, *Renilla* luciferase, cypridina luciferase, Aequorin photoprotein, obelin photoprotein and the like.

The term "coelenterazine substrate" refers to a class of reporter molecules that luminesce when acted upon by a wide variety of bioluminescent proteins such as luciferases (e.g., marine luciferases). Coelenterazine substrates include coelenterazine as well as analogs and derivatives thereof.

As used herein, the term "halogen" or "halo" refers to a fluoro, chloro, bromo or iodo radical.

The term "luminescent enzyme," "bioluminescent enzyme," or "luciferase" as used interchangeably herein refers to a class of oxidative enzymes used in bioluminescence wherein the enzyme produces and emits light when given a substrate. The luciferase may be a naturally occurring, recombinant, or mutant luciferase that uses a luciferase substrate. The luciferase substrate may be luciferin, a luciferin derivative or analog, a preluciferin derivative or analog, a coelenterazine, or a coelenterazine derivative or analog. The luminescent enzyme, if naturally occurring, may be obtained easily by the skilled person from an organism. If the luminescent enzyme is one that occurs naturally or is a recombinant or mutant luminescent enzyme, e.g. one which retains activity in a luciferase-coelenterazine or luciferase-luciferin reaction of a naturally occurring luminescent enzyme, it can be obtained readily from a culture of bacteria, yeast, mammalian cells, insect cells, plant cells, or the like, transformed to express a nucleic acid encoding the luminescent enzyme. Further, the recombinant or mutant luminescent enzyme can be derived from an in vitro cell-free system using a nucleic acid encoding the luciferase. Suitable luminescent enzymes include luciferases derived from bioluminescent decapods such as those from the Oplophoroidea (e.g. *Oplophorus*-derived luciferases), beetle luciferases (e.g., *Photinus pyralis, Photuris pennsylvanica*, etc.), marine organisms such as cnidarians (e.g., *Renilla* luciferase), Aristeidae, Solenoceridae, Luciferidae, Sergestidae, Pasipheidae and Thalassocarididae decapoda families, copepod luciferases, such as *Gaussia* luciferase, such as *Gaussia princeps* luciferase, *Metridia* luciferases, such as *Metridia longa* and *Metridia pacifica* luciferases, *Vargula* luciferases, such as *Vargula hilgendorfii* luciferase, *Pleuromamma xiphias* luciferase, and photoproteins, such as Aequorin, and variants, recombinants, and mutants thereof.

A "luminescent reaction mixture" contains materials that will allow the luminescent enzyme to generate a light signal, i.e., luminescence. The mixture may also contain the enzyme, e.g., the luciferase enzyme or luciferase. The materials, and the particular concentrations and/or amounts, needed to generate a luminescent signal will vary depending on the luminescent enzyme used as well as the type of assay being performed. Often other materials will be added to the solution including: a buffer to maintain the reaction at the proper pH, an additive such as PRIONEX or Bovine serum albumin (BSA) to help maintain enzyme activity, reducing agents, detergents, etc.

As used herein, the terms "*Oplophorus* luciferase" and "*Oplophorus*-derived luciferase" are used interchangeably and refer to a luciferase secreted from the deep-sea shrimp *Oplophorus gracilirostris* (e.g., SEQ ID NO: 1), including wild-type, variants, and mutants thereof. For example, suitable *Oplophorus* luciferase variants are described in U.S. Pat. Nos. 8,557,970 and 8,669,103, each of which is incorporated herein by reference in its entirety. Exemplary *Oplophorus*-derived luciferases include, for example, that of SEQ ID NO: 2 (also interchangeably referred to herein as "NanoLuc", "Nluc," "Nluc luciferase," and "Nluc enzyme").

As used herein, the term "reporter moiety" may refer to a moiety that, under appropriate conditions, directly or indirectly generates a detectable signal. Exemplary reporter moieties include, but are not limited to, fluorophores, luminescent molecules, dyes, radiolabels and substrates for enzymes such as luciferase. In some embodiments, a reporter moiety may indirectly generate a detectable signal, for example, when the reporter moiety is a substrate for an enzyme. The reaction of the enzyme with the substrate then produces a detectable signal such as fluorescence or luminescence. As used herein, the term "bioluminescent reporter moiety" may refer to a moiety that is a substrate for a luciferase. For example, the bioluminescent reporter moiety can be a luciferin, a luciferin derivative, e.g., pre-luciferin, aminoluciferin, quionolyl-luciferin, naphthyl luciferin, fluoroluciferin, chloroluciferin, precursors of luciferin derivatives, a coelenterazine or a coelenterazine derivative or analog, e.g., furimazine. The luminescent signal generated may be detected using a luminometer. As used herein, the term "fluorescent reporter moiety" may refer to a moiety that fluoresces. For example, the fluorescent reporter moiety may be a fluorophore, such as coumarin, R110, fluorescein, DDAO, resorufin, cresyl violet, sily xanthene, or carbopyronine. Fluorescence may be detected using a fluorometer.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

In one aspect, disclosed are compounds of formula (I):

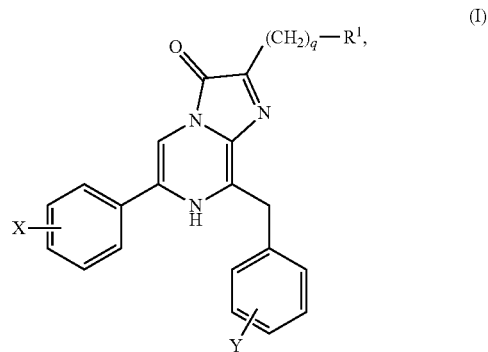

or a tautomer, or a pharmaceutically acceptable salt thereof, wherein

X and Y are independently absent, hydroxy, amino, —COOR$^2$, —SO$_2$—OR$^3$, —PO(OR$^4$)(OR$^5$), or —O—(CR$^{1a}$R$^{1b}$)$_m$—Z;

R$^1$ is optionally substituted aryl, optionally substituted heteroaryl, optionally substituted heterocycle, or optionally substituted cycloalkyl, provided that when both X and Y are absent, R$^1$ is substituted at least with -Q-L-Z;

Z at each occurrence is independently —COOR$^2$, —SO$_2$—OR$^3$, —PO(OR$^4$)(OR$^5$), halogen, —NR$^6$R$^7$, or —NR$^8$—CO—R$^9$;

Q is —O—, —NR$^Q$—, —NR$^Q$—CO—, —CO—NR$^Q$—, —O—CO—NR$^Q$—, or —NR$^Q$—CO—O—;

L is —(CR$^{1a}$R$^{1b}$)$_m$— or —(CR$^{1x}$R$^{1y}$—CR$^{1x}$R$^{1y}$—O)$_{t1}$—(CR$^{1x}$R$^{1y}$)$_{t2}$-Q$^1$-, wherein Q$^1$ is absent, —O—, or —NR$^{Q1}$—;

R$^2$, R$^3$, R$^4$, R$^5$, R$^8$, and R$^9$ at each occurrence are independently hydrogen, optionally substituted C$_1$-C$_8$ alkyl, optionally substituted aryl, optionally substituted cycloalkyl, optionally substituted heteroaryl, or optionally substituted heterocycle;

R$^6$ and R$^7$ at each occurrence are independently hydrogen, optionally substituted C$_1$-C$_8$ alkyl, optionally substituted aryl, optionally substituted cycloalkyl, optionally substituted heteroaryl, or optionally substituted heterocycle; or R$^6$ and R$^7$, together with the nitrogen atom to which they are attached, together form an optionally substituted ring;

R$^{1a}$, R$^{1b}$, R$^Q$, R$^{Q1}$, R$^{1x}$, and R$^{1y}$ at each occurrence are independently hydrogen, C$_1$-C$_4$ alkyl, or C$_1$-C$_4$ haloalkyl;

q is 0, 1, or 2;

m at each occurrence is independently 1-12;

t1 is 1-10; and t2 is 0-5.

In certain embodiments, $R^1$ is substituted at least with -Q-L-Z, in which Q is —O—, —NH—, —NH—CO—, —CO—NH—, —O—CO—NH—, or —NH—CO—O—; and L is —$(CR^{1a}R^{1b})_m$—.

In certain embodiments, $R^1$ is substituted at least with -Q-L-Z, in which Q is —O—; and L is —$(CR^{1a}R^{1b})_m$—. For example, -Q-L-Z may have the formula of —O—$(CR^{1a}R^{1b})_m$—Z.

In certain embodiments, $R^1$ is substituted at least with -Q-L-Z, in which L is —$(CR^{1x}R^{1y}-CR^{1x}R^{1y}-O)_{t1}$—$(CR^{1x}R^{1y})_{t2}$-$Q^1$-. In these embodiments, $Q^1$ may be absent or present. For example, $Q^1$, when present, may be —O— or —NH—.

In certain embodiments, $R^1$ is an aryl, heteroaryl, heterocycle, or cycloalkyl substituted with 0, 1, 2, 3, 4, 5, 6, 7, 8, 9, or 10 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, acyl, and -Q-L-Z. For example, $R^1$ may be an aryl, heteroaryl, heterocycle, or cycloalkyl substituted with 0 or at least one —O—$(CR^{1a}R^{1b})_m$—Z.

In certain embodiments, $R^1$ is an optionally substituted phenyl. For example, in certain embodiments, $R^1$ is a phenyl optionally substituted with 0, 1, 2, 3, or 4 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, acyl, and -Q-L-Z. For example, $R^1$ may be a phenyl substituted with 0 or at least one —O—$(CR^{1a}R^{1b})_m$—Z.

In certain embodiments, $R^1$ is an optionally substituted furyl. For example, in certain embodiments, $R^1$ is a furyl optionally substituted with 0, 1, 2, or 3 substituents, each independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, silyl, substituted silyl, t-butyldimethylsilyl, alkylsulfanyl, sulfanyl, acyl, -Q-L-Z. For $R^1$ may be a furyl substituted with 0 or at least one —O—$(CR^{1a}R^{1b})_m$—Z.

In certain embodiments, $R^1$ is a phenyl or furyl substituted with 0 or at least one -Q-L-Z, in which Q is —O—; and L is —$(CR^{1a}R^{1b})_m$—. For example, $R^1$ may be a phenyl or furyl substituted with 0 or at least one —O—$(CR^{1a}R^{1b})_m$—Z. In addition to -Q-L-Z, $R^1$ may be also substituted with one or more substituents selected from the group consisting of alkyl, halogen, cyano, nitro, haloalkyl, hydroxy, hydroxyalkyl, amino, and —COOH.

In certain embodiments, $R^1$ is selected from the group consisting of

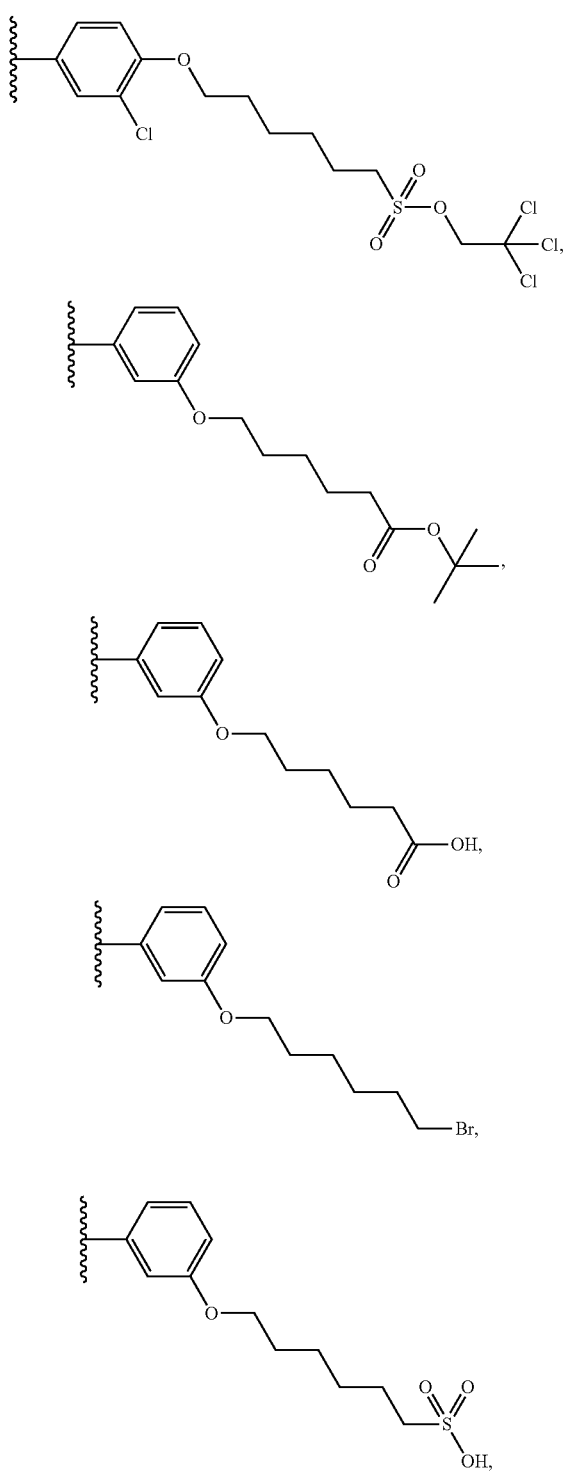

13
-continued
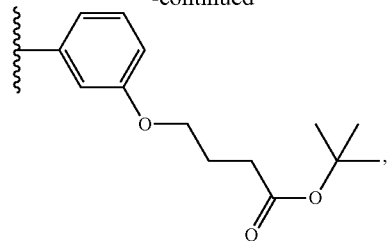
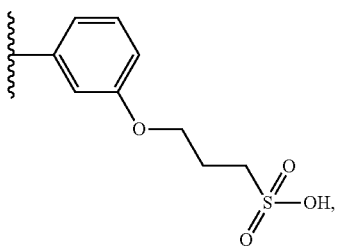
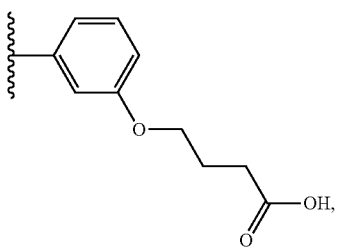
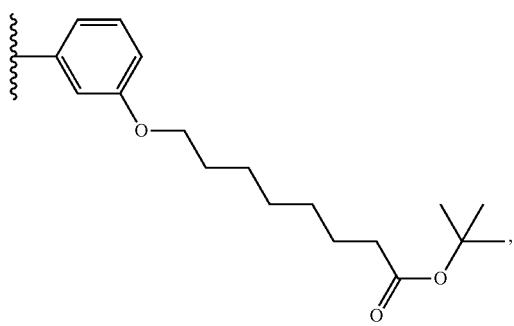
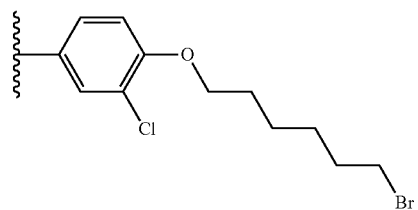
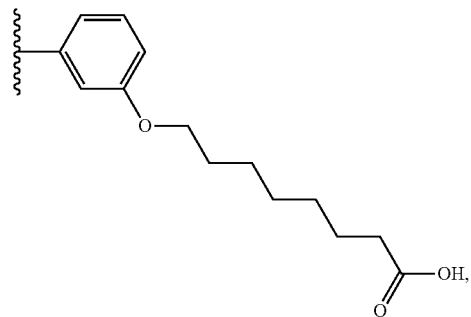
14
-continued
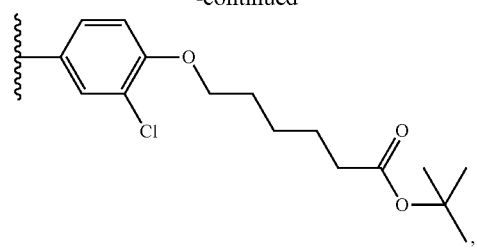
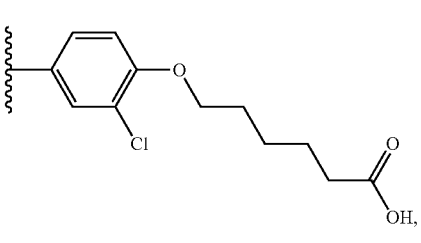
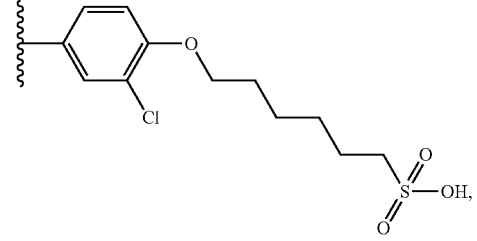
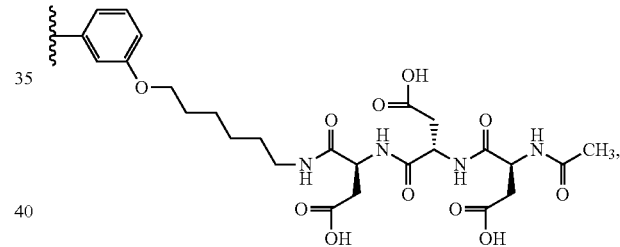
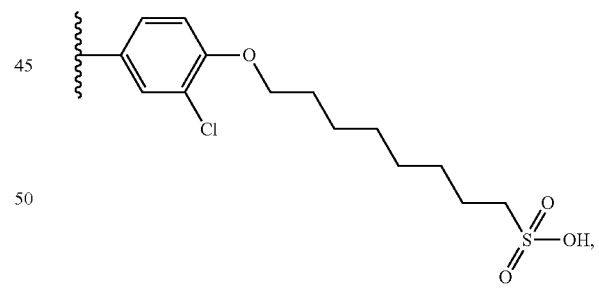
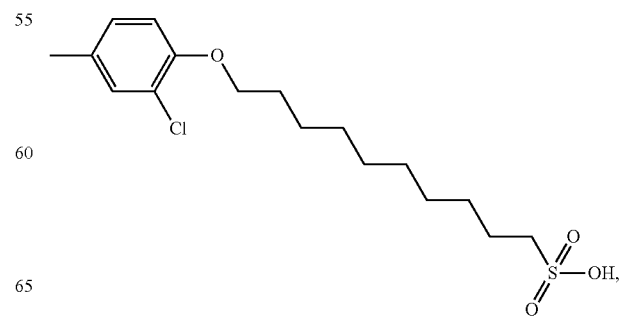

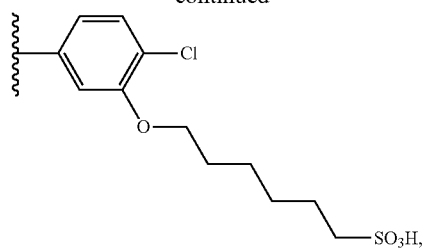
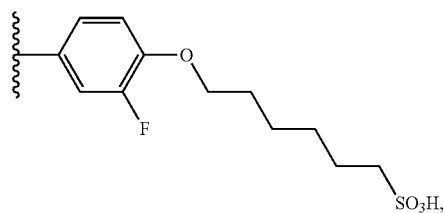
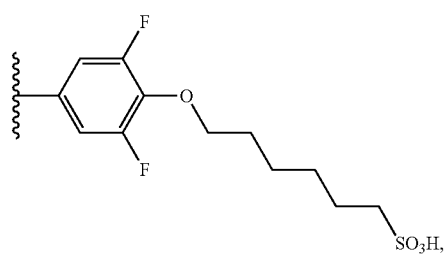
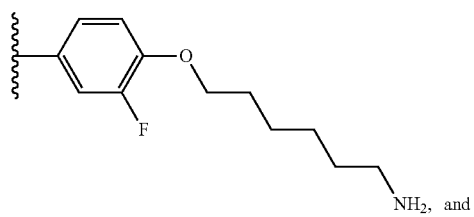
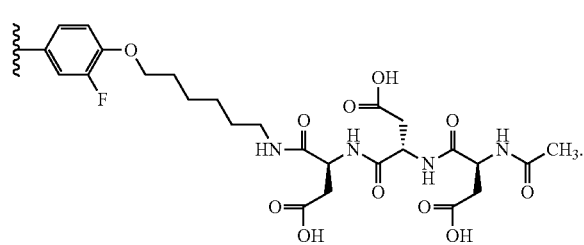
In certain embodiments, —O—$(CR^{1a}R^{1b})_m$—Z is selected from the group consisting of:
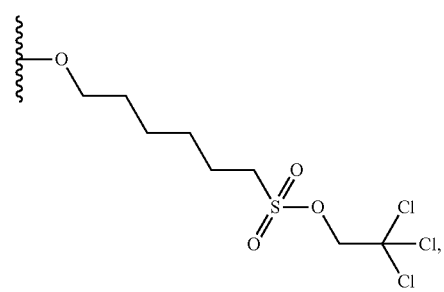
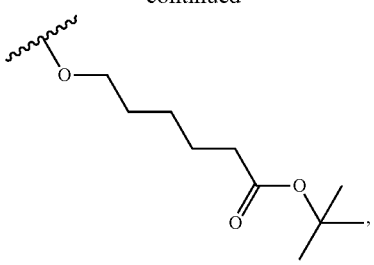
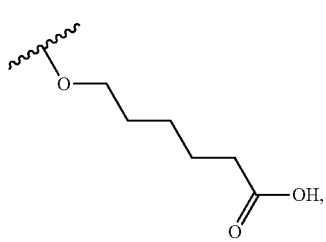
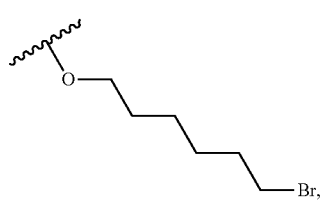
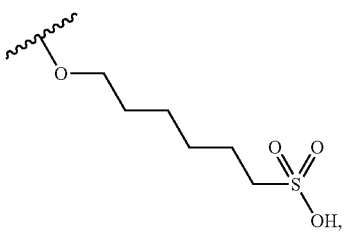
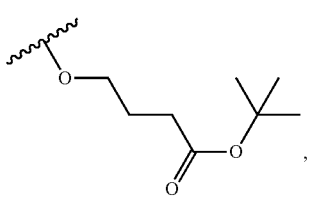
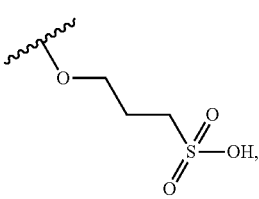
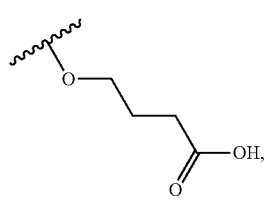
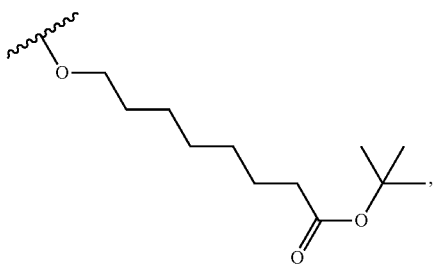

-continued

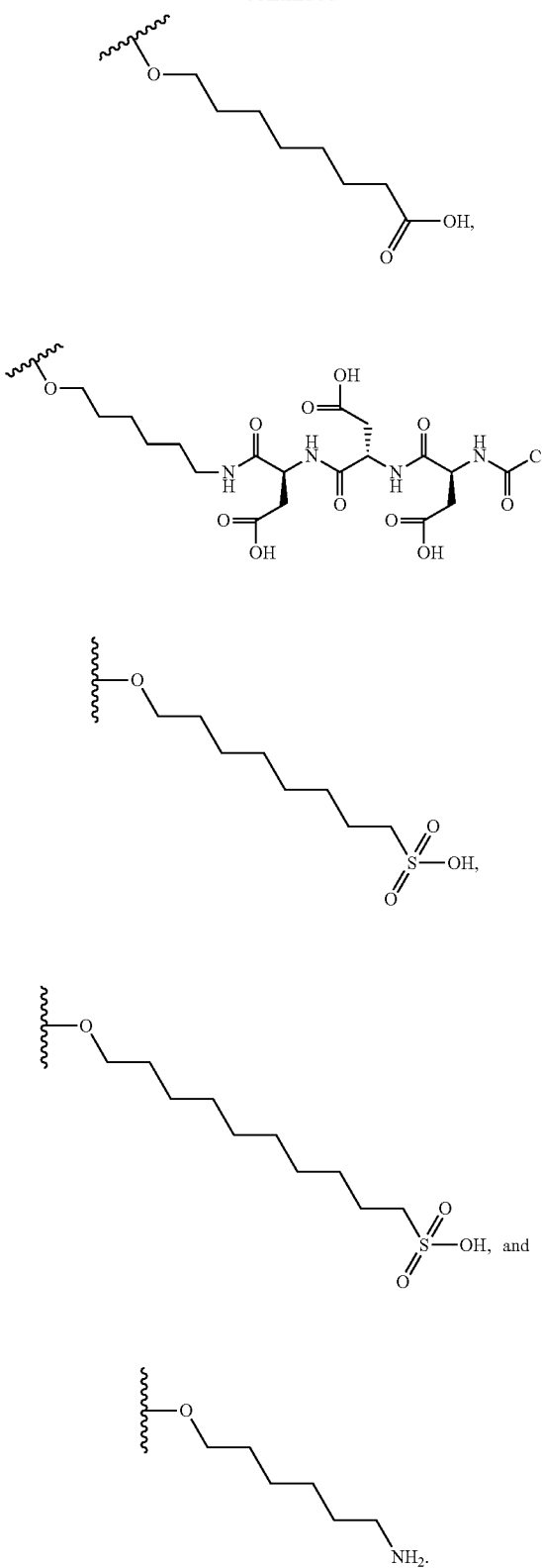

In certain embodiments, q is 1.

In certain embodiments, X is absent, hydroxy, —C(O)—OH, or —C(O)—O—$C_1$-$C_6$-alkyl; and Y is absent. In certain embodiments, X is absent and Y is absent.

In certain embodiments, the compound of formula (I) has formula (I-a):

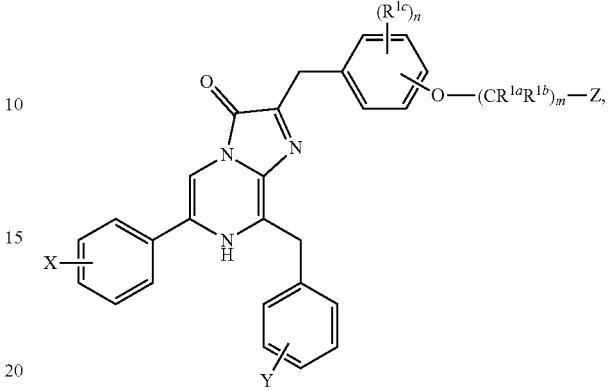

or a tautomer, or a pharmaceutically acceptable salt thereof, wherein $R^{1c}$ is selected from the group consisting of alkyl, halogen, cyano, nitro, haloalkyl, hydroxy, hydroxyalkyl, amino, and —COOH;

n is 0, 1, 2, 3, or 4; and

X, Y, $R^{1a}$, $R^{1b}$, m, and Z are as defined above.

In certain embodiments, the compound has formula (I) or formula (I-a), wherein at least is one of X and Y is absent. For example, in certain embodiments, the compound has formula (I-a), wherein X is absent, or Y is absent, or both X and Y are absent.

In certain embodiments, the compound has formula (I) or formula (I-a), wherein $R^{1c}$ is halogen (e.g., F, Cl, Br, or I).

In certain embodiments, the compound has formula (I) or formula (I-a), wherein m is 3, 4, 5, 6, 7, 8, 9, or 10. For example, m may be 4, 6, 8, or 10.

In certain embodiments, the compound has formula (I) or formula (I-a), wherein Z is —$COOR^2$, —$SO_2$—$OR^3$, or —PO ($OR^4$)($OR^5$), or pharmaceutically acceptable salt thereof. For example, in certain embodiments, the compound has formula (I-a) and Z is a carboxylate group, including —COOH, a carboxylic ester (such as t-butyl ester), or a salt thereof. In other embodiments, the compound has formula (I-a) and Z is a sulfonate group, such as —$SO_3H$, a sulfonate ester (such as 2,2,2-trichloroethyl ester), or a salt thereof (such as sodium salt). In other embodiments, the compound has formula (I-a) and Z is a phosphonate group, including —$PO(OH)_2$, a mono- or di-ester, or salt thereof.

In certain embodiments, the compound has formula (I) or formula (I-a), and Z is —$NR^6R^7$, or pharmaceutically acceptable salt thereof. For example, Z may be —$NR^6R^7$ wherein $R^6$ and $R^7$ at each occurrence are independently hydrogen or optionally substituted $C_1$-$C_8$ alkyl.

In certain embodiments, the compound has formula (I) or formula (I-a), and Z is —$NR^8$—CO—$R^9$, or pharmaceutically acceptable salt thereof wherein $R^9$ is —$(CR^{9a}R^{9b}$—NH—CO$)_u$—$R^{10}$;

$R^{9a}$ and $R^{9b}$ at each occurrence are independently hydrogen or $C_1$-$C_4$ alkyl optionally substituted with —$COOR^{9c}$;

$R^{9c}$ at each occurrence is independently hydrogen or $C_1$-$C_4$ alkyl;

$R^{10}$ is optionally substituted $C_1$-$C_8$ alkyl; and u is 0-10.

In certain embodiments, the compound has formula (I) or formula (I-a), and Z is —NR$^8$—CO—R$^9$ or pharmaceutically acceptable salt thereof, wherein R$^8$ is hydrogen, and R$^9$ is

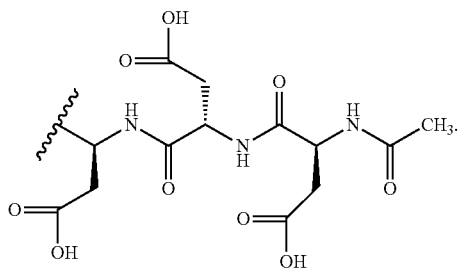 [SMILES: *[C@H](CC(=O)O)NC(=O)[C@H](CC(=O)O)NC(=O)[C@H](CC(=O)O)NC(C)=O]

For example, Z may be

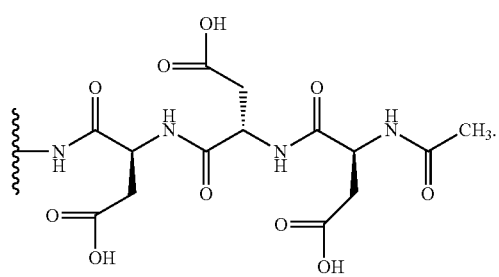 [SMILES: *NC(=O)[C@H](CC(=O)O)NC(=O)[C@H](CC(=O)O)NC(=O)[C@H](CC(=O)O)NC(C)=O]

In certain embodiments, Z is —NR$^8$—CO—R$^9$ or pharmaceutically acceptable salt thereof, wherein R$^9$ comprises residues of one or more amino acids or peptides, including amino acids with electronically charged side chains, such as arginine, histidine, lysine, aspartic acid, and glutamic acid, and peptides containing such amino acids.

In certain embodiments, the compound of formula (I) has formula (I-b):

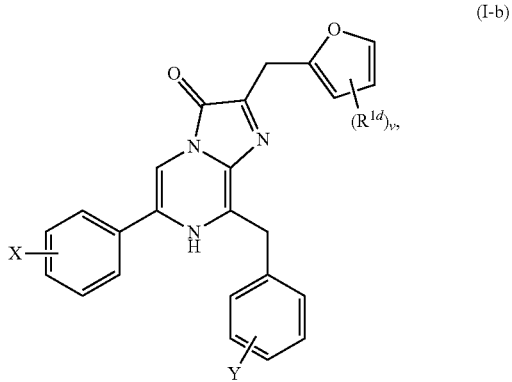

(I-b)

or a tautomer, or a pharmaceutically acceptable salt thereof, wherein

R$^{1d}$ is selected from the group consisting of hydrogen, alkyl, halogen, cyano, haloalkyl, hydroxyalkyl, and —COOH;

v is 0, 1, 2, or 3;

X and Y are each independently absent, —COOR$^2$, —SO$_2$—OR$^3$, —PO (OR$^4$)(OR$^5$), or —O—(CR$^{1a}$R$^{1b}$)$_m$—Z;

at least one of X and Y is present; and

R$^2$, R$^3$, R$^4$, R$^5$, R$^{1a}$, R$^{1b}$, m, and Z are as defined above.

In certain embodiments, the compound has formula (I-b), wherein X is present and Y is absent. In certain embodiments, the compound has formula (I-b), wherein X is absent and Y is present.

In certain embodiments, the compound has formula (I-b), wherein X is —COOR$^2$, —SO$_2$—OR$^3$, —PO (OR$^4$)(OR$^5$), or —O—(CR$^{1a}$R$^{1b}$)$_m$—Z; and Y is absent. For example, in certain embodiments, the compound has formula (I-b) and X is present, wherein X contains a carboxylate group, including —COOH, a carboxylic ester (such as t-butyl ester), or a salt thereof. In other embodiments, the compound has formula (I-b) and X is present, wherein X contains a sulfonate group, such as —SO$_3$H, a sulfonate ester (such as 2,2,2-trichloroethyl ester), or a salt thereof (such as sodium salt). In other embodiments, the compound has formula (I-b) and X is present, wherein X contains a phosphonate group, including —PO(OH)$_2$, a mono- or di-ester, or a salt thereof.

In certain embodiments, the compound has formula (I-b), wherein X is absent and Y is —COOR$^2$, —SO$_2$—OR$^3$, —PO (OR$^4$)(OR$^5$), or —O—(CR$^{1a}$R$^{1b}$)$_m$—Z. For example, in certain embodiments, the compound has formula (I-b) and Y is present, wherein Y contains a carboxylate group, including —COOH, a carboxylic ester (such as t-butyl ester), or a salt thereof. In other embodiments, the compound has formula (I-b) and Y is present, wherein Y contains a sulfonate group, such as —SO$_3$H, a sulfonate ester (such as 2,2,2-trichloroethyl ester), or a salt thereof (such as sodium salt). In other embodiments, the compound has formula (I-b) and Y is present, wherein Y contains a phosphonate group, including —PO(OH)$_2$, a mono- or di-ester, or a salt thereof.

Suitable compounds include the following:

2,2,2-trichloroethyl 6-(4-((8-benzyl-3-oxo-6-phenyl-3,7-dihydroimidazo[1,2-a]pyrazin-2-yl)methyl)-2-chlorophenoxy)hexane-1-sulfonate;

tert-butyl 6-(3-((8-benzyl-3-oxo-6-phenyl-3,7-dihydroimidazo[1,2-a]pyrazin-2-yl)methyl)phenoxy)hexanoate;

6-(3-((8-benzyl-3-oxo-6-phenyl-3,7-dihydroimidazo[1,2-a]pyrazin-2-yl)methyl)phenoxy)hexanoic acid;

8-benzyl-2-(3-((6-bromohexyl)oxy)benzyl)-6-phenylimidazo[1,2-a]pyrazin-3(7H)-one;

sodium 6-(3-((8-benzyl-3-oxo-6-phenyl-3,7-dihydroimidazo[1,2-a]pyrazin-2-yl)methyl)phenoxy)hexane-1-sulfonate;

tert-butyl 4-(3-((8-benzyl-3-oxo-6-phenyl-3,7-dihydroimidazo[1,2-a]pyrazin-2-yl)methyl)phenoxy)butanoate;

sodium 3-(3-((8-benzyl-3-oxo-6-phenyl-3,7-dihydroimidazo[1,2-a]pyrazin-2-yl)methyl)phenoxy)propane-1-sulfonate;

4-(3-((8-benzyl-3-oxo-6-phenyl-3,7-dihydroimidazo[1,2-a]pyrazin-2-yl)methyl)phenoxy)butanoic acid;

tert-butyl 8-(3-((8-benzyl-3-oxo-6-phenyl-3,7-dihydroimidazo[1,2-a]pyrazin-2-yl)methyl)phenoxy)octanoate;

8-benzyl-2-(4-((6-bromohexyl)oxy)-3-chlorobenzyl)-6-phenylimidazo[1,2-a]pyrazin-3(7H)-one;

8-(3-((8-benzyl-3-oxo-6-phenyl-3,7-dihydroimidazo[1,2-a]pyrazin-2-yl)methyl)phenoxy)octanoic acid;

tert-butyl 6-(4-((8-benzyl-3-oxo-6-phenyl-3,7-dihydroimidazo[1,2-a]pyrazin-2-yl)methyl)-2-chlorophenoxy) hexanoate;

6-(4-((8-benzyl-3-oxo-6-phenyl-3,7-dihydroimidazo[1,2-a]pyrazin-2-yl)methyl)-2-chlorophenoxy)hexanoic acid;

sodium 6-(4-((8-benzyl-3-oxo-6-phenyl-3,7-dihydroimidazo[1,2-a]pyrazin-2-yl)methyl)-2-chlorophenoxy)hexane-1-sulfonate;

(S)-3-acetamido-4-(((S)-1-(((S)-1-((6-(3-((8-benzyl-3-oxo-6-phenyl-3,7-dihydroimidazo[1,2-a]pyrazin-2-yl)methyl)phenoxy)hexyl)amino)-3-carboxy-1-oxopropan-2-yl)amino)-3-carboxy-1-oxopropan-2-yl)amino)-4-oxobutanoic acid;

sodium 8-(4-((8-benzyl-3-oxo-6-phenyl-3,7-dihydroimidazo[1,2-a]pyrazin-2-yl)methyl)-2-chlorophenoxy)octane-1-sulfonate;

sodium 10-(4-((8-benzyl-3-oxo-6-phenyl-3,7-dihydroimidazo[1,2-a]pyrazin-2-yl)methyl)-2-chlorophenoxy)decane-1-sulfonate;

sodium 6-(5-((8-benzyl-3-oxo-6-phenyl-3,7-dihydroimidazo[1,2-a]pyrazin-2-yl)methyl)-2-chlorophenoxy)hexane-1-sulfonate;

sodium 6-(4-((8-benzyl-3-oxo-6-phenyl-3,7-dihydroimidazo[1,2-a]pyrazin-2-yl)methyl)-2-fluorophenoxy)hexane-1-sulfonate;

sodium 6-(4-((8-benzyl-3-oxo-6-phenyl-3,7-dihydroimidazo[1,2-a]pyrazin-2-yl)methyl)-2,6-difluorophenoxy)hexane-1-sulfonate;

2-(4-((6-aminohexyl)oxy)-3-fluorobenzyl)-8-benzyl-6-phenylimidazo[1,2-a]pyrazin-3(7H)-one;

6-(4-((8-benzyl-6-(3-hydroxyphenyl)-3-oxo-3,7-dihydroimidazo[1,2-a]pyrazin-2-yl)methyl)-2-chlorophenoxy)hexane-1-sulfonic acid;

(S)-3-acetamido-4-(((S)-1-(((S)-1-((6-(4-((8-benzyl-3-oxo-6-phenyl-3,7-dihydroimidazo[1,2-a]pyrazin-2-yl)methyl)-2-fluorophenoxy)hexyl)amino)-3-carboxy-1-oxopropan-2-yl)amino)-3-carboxy-1-oxopropan-2-yl)amino)-4-oxobutanoic acid;

tert-butyl 3-(8-benzyl-2-(furan-2-ylmethyl)-3-oxo-3,7-dihydroimidazo[1,2-a]pyrazin-6-yl)benzoate;

3-(8-benzyl-2-(furan-2-ylmethyl)-3-oxo-3,7-dihydroimidazo[1,2-a]pyrazin-6-yl)benzoic acid;

4-(8-benzyl-2-(furan-2-ylmethyl)-3-oxo-3,7-dihydroimidazo[1,2-a]pyrazin-6-yl)benzoic acid; and 6-(4-((6-aminohexyl)oxy)phenyl)-8-benzyl-2-(furan-2-ylmethyl)imidazo[1,2-a]pyrazin-3(7H)-one.

Compound names are assigned by using Struct=Name naming algorithm as part of CHEMDRAW® ULTRA v. 12.0.

The compounds described herein can be in the form of a salt. A neutral form of the compound may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations. Examples of suitable organic cations include, but are not limited to, ammonium ion (i.e., $NH_4^+$) and substituted ammonium ions (e.g., $NH_3R_1^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine.

If the compound is cationic, or has a functional group that may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound herein also includes salt forms thereof.

The compounds may exist as stereoisomers wherein asymmetric or chiral centers are present. The stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof, and these are specifically included within the scope of this invention. Stereoisomers include enantiomers and diastereomers and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography, and optional liberation of the optically pure product from the auxiliary as described in Fumiss, Hannaford, Smith, and Tatchell, "Vogel's Textbook of Practical Organic Chemistry", 5$^{th}$ edition (1989), Longman Scientific & Technical, Essex CM20 2JE, England, or (2) direct separation of the mixture of optical enantiomers on chiral chromatographic columns, or (3) fractional recrystallization methods.

In some embodiments, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

It should be understood that the compounds may possess tautomeric forms, as well as geometric isomers, and that these also constitute an aspect of the invention.

The present disclosure also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^2H$, $^3H$, $^{13}C$, $^{14}C$, $^{15}N$, $^{18}O$, $^{17}O$, $^{31}P$, $^{32}P$, $^{35}$S, $^{18}$F, and $^{36}$Cl, respectively. Substitution with heavier isotopes such as deuterium, i.e., $^{2}$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

A. Properties of the Compounds of Formula (I)

The compounds of formula (I) may be substrates of luciferases to produce luminescence. "Luminescence" refers to the light output of a luciferase under appropriate conditions, e.g., in the presence of a suitable substrate such as a coelenterazine analogue. The light output may be measured as an instantaneous or near-instantaneous measure of light output (which is sometimes referred to as "T=0" luminescence or "flash") at the start of the luminescence reaction, which may be initiated upon addition of the coelenterazine substrate. The luminescence reaction in various embodiments is carried out in a solution. In other embodiments, the luminescence reaction is carried out on a solid support. The solution may contain a lysate, for example from the cells in a prokaryotic or eukaryotic expression system. In other embodiments, expression occurs in a cell-free system, or the luciferase protein is secreted into an extracellular medium, such that, in the latter case, it is not necessary to produce a lysate. In some embodiments, the reaction is started by injecting appropriate materials, e.g., coelenterazine analogue, buffer, etc., into a reaction chamber (e.g., a well of a multiwell plate such as a 96-well plate) containing the luminescent protein. In still other embodiments, the luciferase and/or coelenterazine analogues (e.g., compounds of formula (I)) are introduced into a host and measurements of luminescence are made on the host or a portion thereof, which can include a whole organism or cells, tissues, explants, or extracts thereof. In certain embodiments, the measurement of luminescence is made on the surface of host, such as on the cell surface. In still other embodiments, the luciferase and/or coelenterazine analogues (e.g., compounds of formula (I)) are introduced into a host and measurements of luminescence are made in the extracellular space. The reaction chamber may be situated in a reading device which can measure the light output, e.g., using a luminometer or photomultiplier. The light output or luminescence may also be measured over time, for example in the same reaction chamber for a period of seconds, minutes, hours, etc. The light output or luminescence may be reported as the average over time, the half-life of decay of signal, the sum of the signal over a period of time, or the peak output. Luminescence may be measured in Relative Light Units (RLUs).

Compounds of formula (I) can have an RLU of greater than or equal to 1, greater than or equal to 2, greater than or equal to 3, greater than or equal to 4, greater than or equal to 5, greater than or equal to 10, greater than or equal to 20, greater than or equal to 30, greater than or equal to 40, greater than or equal to 50, or greater than or equal to 100, relative to coelenterazine or a known coelenterazine analogue, such as furimazine.

"Cell permeability", "cell membrane permeability", or "membrane permeability" as used interchangeably herein refers to the ability of the compound to penetrate the cell membrane. This may refer to the ability of the compound to partially embed within the cell membrane. This may refer to the ability of the compound to completely pass through the cell membrane to reach the intracellular space. The coelenterazine analogues disclosed herein may display decreased cell permeability.

"Biocompatibility" refers to the tolerance of a cell (e.g., prokaryotic or eukaryotic) to a coelenterazine analogue (e.g., compounds of formula (I)). Biocompatibility of a coelenterazine analogue is related to the stress it causes on the host cell.

Enhanced biocompatibility of the coelenterazine analogues (e.g., compounds of formula (I)), may be determined by measuring cell viability and/or growth rate of cells. For example, enhanced biocompatibility of the coelenterazine analogues may be determined by measuring cell viability in the absence of luciferase expression of cells exposed to the coelenterazine analogues compared to native or known coelenterazines to determine how compatible and/or toxic the coelenterazine analogues are to the cells.

In particular, enhanced biocompatibility may be determined using cell viability analysis (e.g., using the CELL-TITER-GLO® Luminescent Cell Viability assay), an apoptosis assay (e.g., using the CASPASE-GLO® assay technology), or another method known in the art. The effect of the compounds of formula (I) on cell viability or apoptosis may be compared to the effect of native or known coelenterazine analogues on cell viability or apoptosis.

Enhanced biocompatibility may also be determined by measuring the effect of the coelenterazine analogues (e.g., compounds of formula (I)) on cell growth or gene expression. For example, enhanced biocompatibility of the compounds of formula (I) may be determined by measuring the cell number after a period of time or by determining the expression of stress response genes in a sample of cells that are exposed to compounds of formula (I) compared to cells exposed to a native or known coelenterazine or no coelenterazine. The effect of the compounds of formula (I) on cell growth or gene expression may be compared to a native or known coelenterazine.

B. Synthesis of Compounds of Formula (I)

Compounds of formula (I) may be prepared by synthetic processes or by metabolic processes. Preparation of the compounds by metabolic processes includes those occurring in the human or animal body (in vivo) or processes occurring in vitro.

Compounds of formula (I), wherein the groups $R^1$ and q have the meanings as set forth in the Summary section unless otherwise noted, can be synthesized as shown in Schemes 1-4 and General Procedures A-H. Suitable synthesis methods may also include, for example, those disclosed in U.S. Ser. No. 62/295,363 to Shakhmin et al., "COELENTERAZINE ANALOGUES," filed Feb. 15, 2016, which is incorporated by reference herein in its entirety.

Abbreviations which have been used in the descriptions of the Schemes that follow are: Ac$_2$O for acetic anhydride; CDI for carbonyldiimidazole; MeOH for methanol; TMG for 1,1,3,3-tetramethylguanidine; and TFA for trifluoroacetic acid.

Scheme 1. Synthesis of coelenterazine analogues containing carboxyl groups (General Procedures A, B, C, D, E, F)
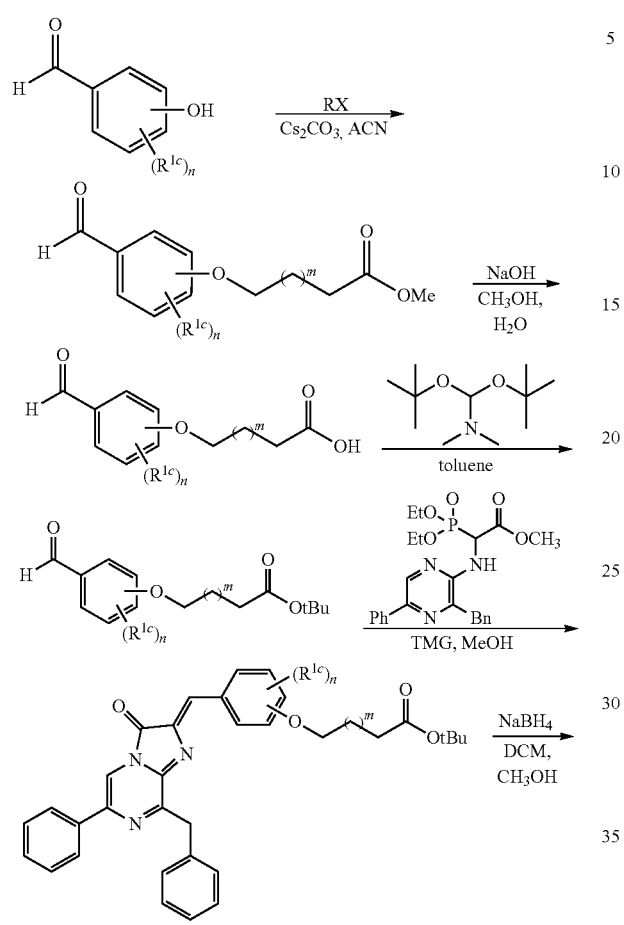
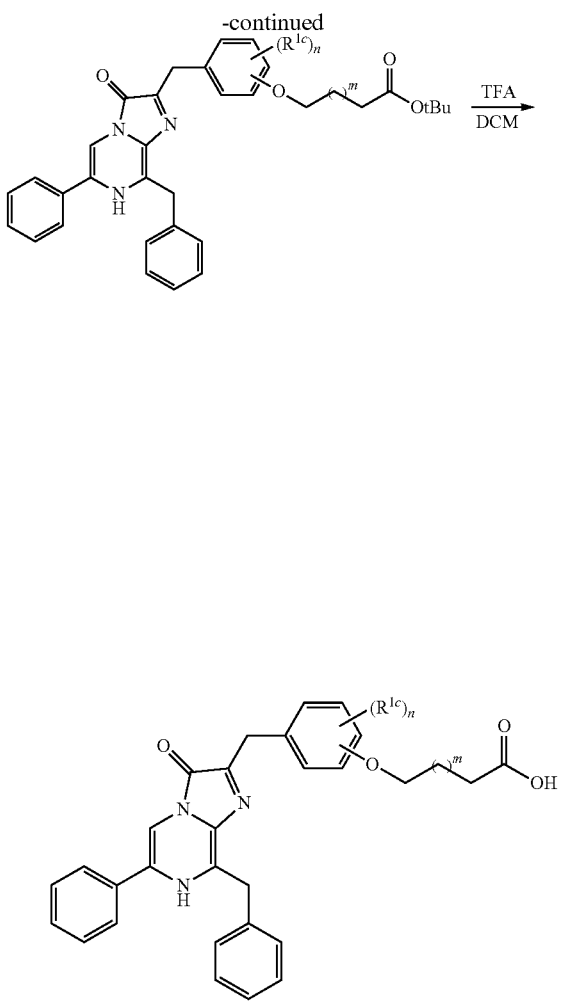
Scheme 2. Coelenterazine analogues containing amine groups (General Procedures A, D, E, F)
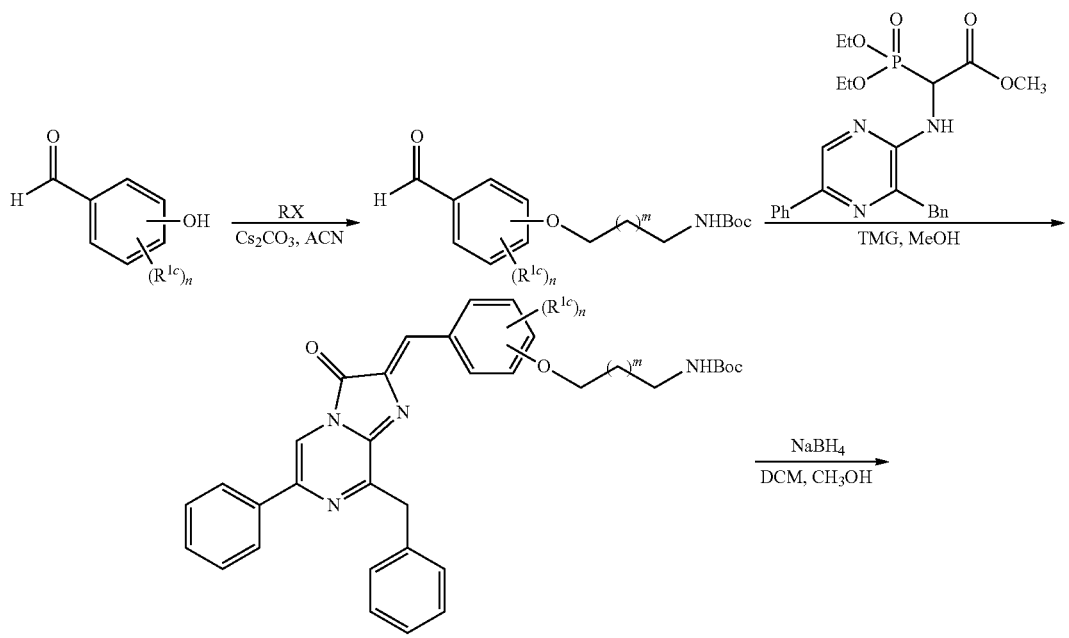

-continued
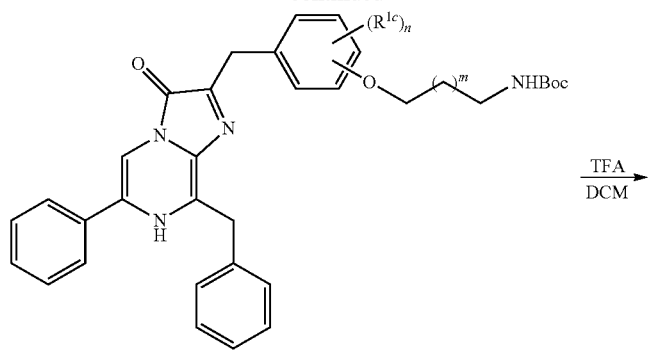
TFA / DCM →
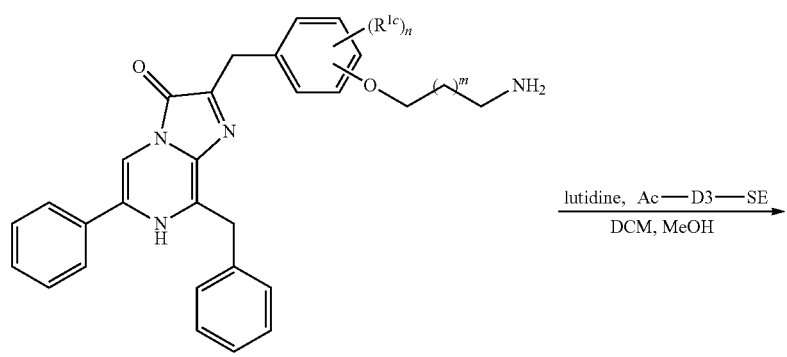
lutidine, Ac—D3—SE / DCM, MeOH →
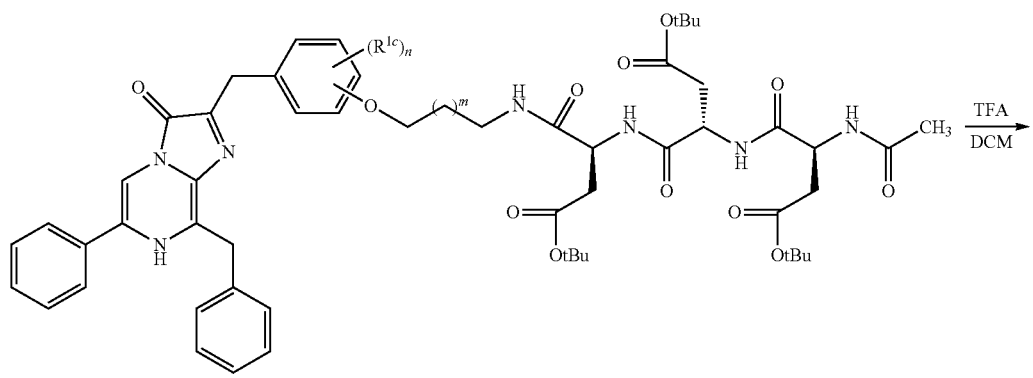
TFA / DCM →
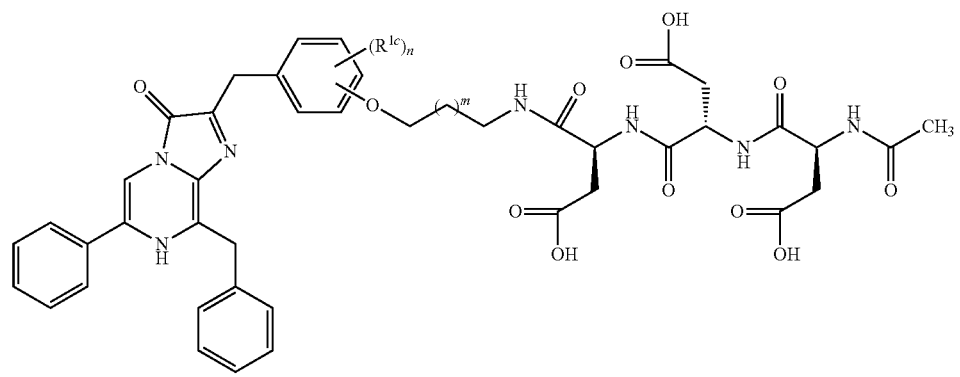

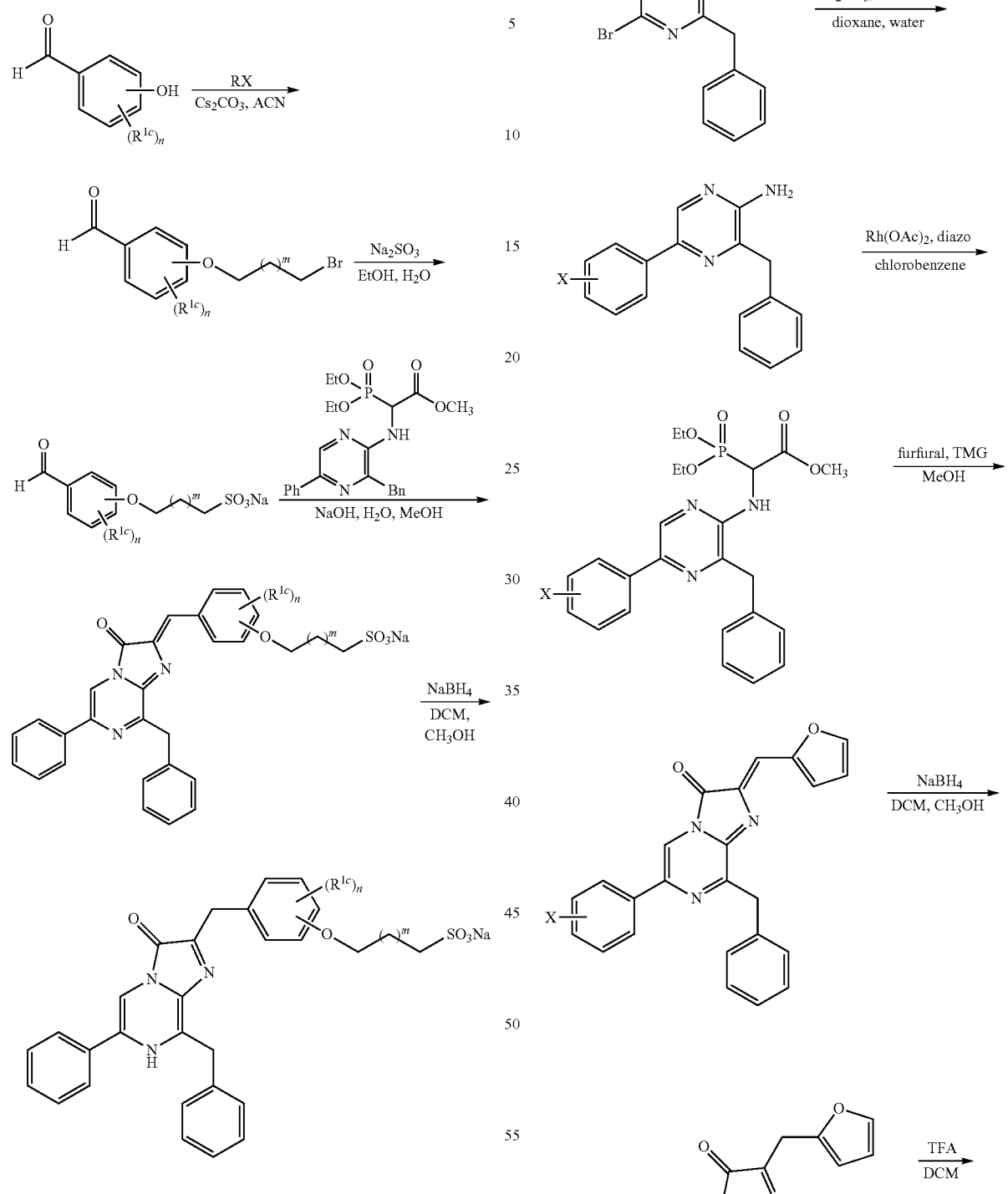
Scheme 3. Coelenterazine analogues containing sulfonate groups (General Procedures A, G, H, I)
Scheme 4. Coelenterazine of furimazine analogues containing 6-position modifications (General Procedures D, E, F)

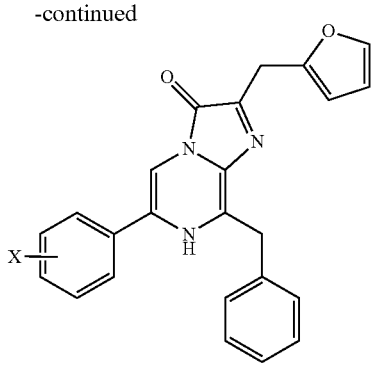

General Procedures

General Procedure a (Alkylation of Hydroxyl Benzaldehyde):

To a solution of the hydroxy benzaldehyde (1 eq) in acetonitrile, alkyl bromide (1.5 eq) and cesium carbonate (1.2 eq) was added. The mixture was heated to 60° C. for 4-18 h. The mixture was cooled, diluted with ethyl acetate and water, and the aqueous layer extracted with ethyl acetate. The organic layers were combined, dried with sodium sulfate, filtered, concentrated, and purified with silica gel chromatography.

General Procedure B (Saponification):

To a solution of methyl or ethyl ester (1 eq) in methanol, sodium hydroxide (2 M, 1.3 eq) was added. The solution was stirred at RT for 18 h. The solution was acidified with HCl (2 M), diluted with ethyl acetate and water, and the aqueous layer extracted with ethyl acetate. The organic layers were combined, dried with sodium sulfate, filtered, concentrated, and used as crude product in the next step.

General Procedure C (t-Butyl Ester Formation):

To a suspension of the carboxylate (1 eq) in toluene, 1,1-di-tert-butoxy-N,N-dimethylmethanamine (2 eq) was added. The mixture was heated to 85° C. for 18 h. The mixture was cooled, diluted with ethyl acetate and water, and the aqueous layer was extracted with ethyl acetate. The organic layers were combined, dried with sodium sulfate, filtered, concentrated, and purified with silica gel chromatography.

General Procedure D (HWE Reaction):

To a solution of the aldehyde (1 eq) and methyl 2-((3-benzyl-5-phenylpyrazin-2-yl)amino)-2-(diethoxyphosphoryl)acetate (1 eq) in methanol, 1,1,3,3-tetramethylguanidine (3 eq) was added. The solution was stirred at RT for 0.5-2 h. The mixture was diluted with dichloromethane and ~0.1 M HCl, and the aqueous layer was extracted with dichloromethane. The organic layers were combined, dried with sodium sulfate, filtered, concentrated, and purified with silica gel chromatography.

General Procedure E (Reduction):

A suspension of the dehydro-coelenterazine (1 eq) in dichloromethane and methanol (1:1) was chilled with an ice bath. Sodium borohydride (5 eq) was added, and the mixture stirred for 0.5-2 h. The mixture was diluted with dichloromethane and ~0.1 M HCl, and the aqueous layer was extracted with dichloromethane. The organic layers were combined, dried with sodium sulfate, filtered, concentrated, and purified with silica gel chromatography.

General Procedure F (TFA Deprotection):

To a solution of the coelenterazine analogue in dichloromethane (10 mL), trifluoroacetic acid (1 mL) was added. The solution was stirred for 2-6 h. The mixture was diluted with toluene, concentrated, resuspended in toluene, and concentrated. This was repeated two times. The crude product was purified with silica gel chromatography.

General Procedure G (Sulfonation):

A solution of the alkyl bromide (1 eq) in ethanol was heated to 75° C. An aqueous solution of sodium sulfite (5 eq) was added, and the mixture was stirred at 75° C. for 18 h. The mixture was diluted with ethanol, added to Celite, concentrated, and purified with silica gel chromatography.

General Procedure H (HWE Reaction with Sulfonates):

To a solution of the sulfonated aldehyde (1 eq) and methyl 2-((3-benzyl-5-phenylpyrazin-2-yl)amino)-2-(diethoxyphosphoryl)acetate (1 eq) in methanol, sodium hydroxide (2 M, 3 eq) was added. The solution was stirred at RT for 0.5-2 h. The mixture was diluted with ethanol, added to Celite, concentrated, and purified with silica gel chromatography.

General Procedure I (Reduction with Sulfonates):

A suspension of the dehydro-coelenterazine (1 eq) in dichloromethane and methanol (1:1) was chilled with an ice bath. Sodium borohydride (5 eq) was added, and the mixture stirred for 0.5-2 h. The mixture was diluted with ethanol, added to Celite, concentrated, and purified with silica gel chromatography.

Optimum reaction conditions and reaction times for each individual step can vary depending on the particular reactants employed and substituents present in the reactants used. Specific procedures are provided in the Examples section. Reactions can be worked up in the conventional manner, e.g., by eliminating the solvent from the residue and further purifying according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups, and the methods for protecting and deprotecting different substituents using such suitable protecting groups, are well known to those skilled in the art; examples of which can be found in PGM Wuts and TW Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step) or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material or by resolution of a mixture of the geometric isomers of the compound or intermediates using a standard procedure such as chromatographic separation.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. Methods of Use and Kits

The compounds of the disclosure may be used in any way that luciferase substrates, e.g., coelenterazine or coelenterazine analogues, have been used. For example, they may be used in a bioluminogenic method that employs an analogue of coelenterazine to detect one or more molecules in a sample, e.g., an enzyme, a cofactor for an enzymatic reaction, an enzyme substrate, an enzyme inhibitor, an enzyme activator, or OH radicals, or one or more conditions, e.g., redox conditions. The sample may include an animal (e.g., a vertebrate), a plant, a fungus, physiological fluid (e.g., blood, plasma, urine, mucous secretions), a cell, a cell lysate, a cell supernatant, or a purified fraction of a cell (e.g., a subcellular fraction). The presence, amount, spectral distribution, emission kinetics, or specific activity of such a molecule may be detected or quantified. The molecule may be detected or quantified in solution, including multiphasic solutions (e.g., emulsions or suspensions), or on solid supports (e.g., particles, capillaries, or assay vessels).

In certain embodiments, the compounds of formula (I) may be used to quantify small molecules. In some embodiments, a coelenterazine (e.g., a native or known coelenterazine or a compound of formula (I)) can be used as a probe of a specific biochemical activity, e.g., apoptosis or drug metabolism. In some embodiments, the coelenterazine concentration is coupled to a specific enzyme activity by a "pro-coelenterazine" or "pro-substrate" that can be acted on by the specific enzyme of interest. In some embodiments, the pro-coelenterazine is a molecule that cannot support luminescence directly when combined with a luciferase, but can be converted into coelenterazine through catalytic processing by a specific enzyme of interest. In some embodiments, the approach can be used for enzymes such as those used in drug metabolism, e.g., cytochrome P450 enzymes, monoamine oxidase, and glutathione S-transferase; and apoptosis, e.g., caspases. For example, coelenterazine (e.g., a native or known coelenterazine, or a compound of formula (I)) can be modified to contain a cleavable group, such as 6'-O-methyl. In some embodiments, when incubated with a specific cytochrome P450 enzyme, the 6'O-methyl is cleaved, and the pro-coelenterazine converted to coelenterazine, which can be detected with a luciferase. In some embodiments, the pro-coelenterazine can be combined with other components necessary to support luminescence, e.g., luminescent protein such as a luciferase, to provide a single reagent and a homogeneous assay. For example, when the reagent is added to a sample, luminescence is generated as pro-coelenterazine is converted to coelenterazine. In various embodiments, similar assays can be developed for other enzymes, small molecules, or other cellular processes that can be linked to the generation of coelenterazines from pro-coelenterazines.

In certain embodiments, the compounds of formula (I) can be used for detecting luminescence in live cells. In certain embodiments, the compounds of formula (I) may be used in a bioluminogenic method to measure extracellular events. In other embodiments, the compounds of formula (I) may be used in a bioluminogenic method to measure cell-surface events. In some embodiments, the compounds of formula (I) may be used in a bioluminogenic method to measure cell death. In a particular embodiment, the compounds of formula (I) may be used in a method for detecting cell death in a sample, the method comprising: (a) contacting a sample with a compound that induces cell death; (b) contacting the sample with a compound as described above; and (c) detecting luminescence in the sample, wherein the sample comprises cells expressing a coelenterazine-utilizing luciferase. For example, the target cell in may include cells expressing NanoLuc, and a compound of interest may be added to the target cells to induce cell death. The target cells may include HEK293 cells or other suitable cell lines or cell cultures.

In some embodiments, target cells expressing NanoLuc may also be mixed with effector cells, including but not limited to primary T cells, NK cells, CAR-T cells, or TALL-104 cells. A compound of interest may be added to the cells to activate the effector cells. Subsequent induction of cell death could be detected using the disclosed compounds.

In some embodiments, the target cell may be a tumor cell. The disclosed compounds may be used to monitor cell death, and thus may be used to determine the efficacy of an anti-tumor treatment. For example, the compound of interest may be an antibody designed to kill the tumor cell. The antibody may have any mode of action of killing tumor cells, including but not limited to ADCC, ADCP, CDC, ADC, BiTE or Immuno-Oncology drugs killing tumor cells. Antibody-induced death of the tumor cell would release the intracellular NanoLuc from the tumor cell, thus enabling detection by the disclosed cell-impermeable compounds.

In some embodiments, the compounds of formula (I) may be tethered by a stable covalent linker to a polar group diminishes the cell permeability of the coelenterazine analog. In addition to being cell impermeable, the compounds of formula (I) show comparable biocompatibility to native coelenterazine in terms of cell viability. In some embodiments, the compounds of formula (I) containing chemical modifications known to increase the stability of native coelenterazine in media can be synthesized and used for more robust, live cell luciferase-based reporter assays. In still other embodiments, a sample (including cells, tissues, animals, etc.) containing a luciferase and a compound of formula (I) may be assayed using various microscopy and imaging techniques. In still other embodiments, a secretable luciferase may be expressed in cells as part of a live-cell reporter system, and secretion of the luciferase may be detected by compounds of formula (I). In a particular embodiment, the present compound may be used in a method for detecting secretion of a bioluminescent enzyme in a sample, the method comprising: (a) contacting the sample with a compound as described above; and (b) detecting luminescence in the sample, wherein the sample comprises cells expressing a secretable bioluminescent enzyme. The sample in such method may include cells such as HEK293 cells or other suitable cell lines or cell cultures.

In certain embodiments, the compounds of formula (I) disclosed herein may be provided as part of a kit. In some embodiments, the kit may include one or more luciferases (in the form of a polypeptide, a polynucleotide, or both) and a coelenterazine, along with suitable reagents and instructions to enable a user to perform assays such as those disclosed herein. The coelenterazine may be any of the native, known, or compounds of formula (I) disclosed herein. The kit may also include one or more buffers, such as those disclosed herein.

4. Examples

Example 1

2,2,2-trichloroethyl 6-(4-((8-benzyl-3-oxo-6-phenyl-3,7-dihydroimidazo[1,2-a]pyrazin-2-yl)methyl)-2-chlorophenoxy)hexane-1-sulfonate (JRW-0665)

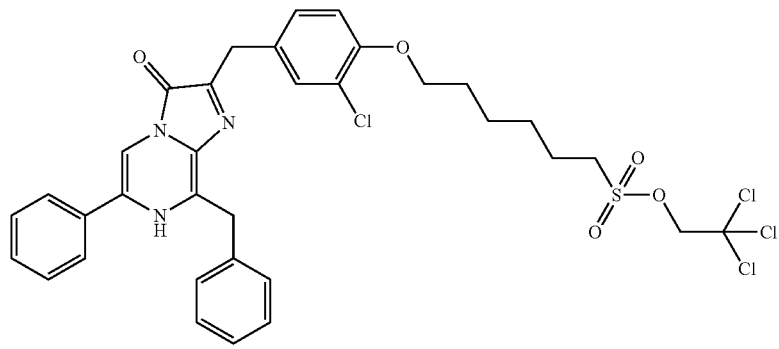 [SMILES: O=c1c(Cc2ccc(OCCCCCCS(=O)(=O)OCC(Cl)(Cl)Cl)c(Cl)c2)nc2c(Cc3ccccc3)[nH]c(-c3ccccc3)cn1-2]

Step 1. 4-((6-bromohexyl)oxy)benzaldehyde (JRW-0651)

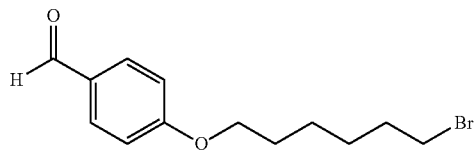 [SMILES: O=Cc1ccc(OCCCCCCBr)cc1]

Following general procedure A, 4-hydroxybenzaldehyde (2.0 g, 16.4 mmol) was reacted with 1,6-dibromohexane (8.0 g, 32.8 mmol) to afford the desired product (3.1 g, 66%) as a white solid. $^1$H NMR (300 MHz, CDCl$_3$) δ 10.87-10.46 (m, 1H), 8.87-8.48 (m, 2H), 7.85-7.78 (m, 2H), 5.01-4.67 (m, 2H), 4.41-4.07 (m, 2H), 2.83-2.52 (m, 4H), 2.45-2.25 (m, 4H); ESI MS m/z 285 [M+H]$^+$.

Scheme 5. Synthesis of Intermediate JRW-0656

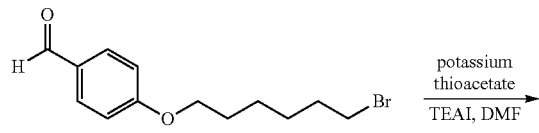

Step 2. S-(6-(4-formylphenoxy)hexyl) ethanethioate (JRW-0653)

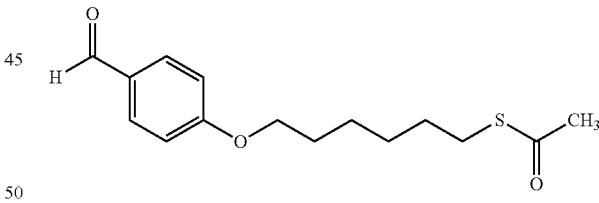

To a solution of 4-((6-bromohexyl)oxy)benzaldehyde (3.00 g, 10.5 mmol) in DMF (30 mL), tetraethylammonium iodide (0.27 g, 1.1 mmol) was added. The mixture was cooled with an ice bath and potassium thioacetate (1.32 g, 11.6 mmol) was added. The mixture was warmed to RT, stirred for 1 h, diluted with ethyl acetate and water, and the aqueous layer was extracted with ethyl acetate. The organic layers were combined, dried with sodium sulfate, filtered, concentrated, and purified with silica gel chromatography to afford the desired product (2.45 g, 83%) as a colorless oil. $^1$H NMR (300 MHz, CDCl$_3$) δ 9.87 (s, 1H), 7.85-7.77 (m, 2H), 7.02-6.94 (m, 2H), 4.02 (t, J=6.4, 2H), 2.93-2.82 (m, 2H), 2.32 (s, 3H), 1.92-1.34 (m, 8H); ESI MS m/z 281 [M+H]$^+$.

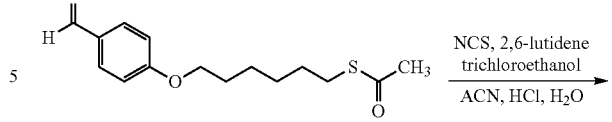

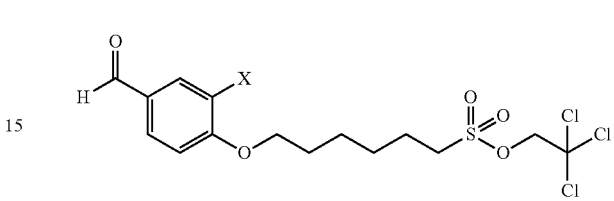

X = H, Cl

Step 3. 2,2,2-trichloroethyl 6-(4-formylphenoxy)hexane-1-sulfonate and 2,2,2-trichloroethyl 6-(2-chloro-4-formylphenoxy)hexane-1-sulfonate

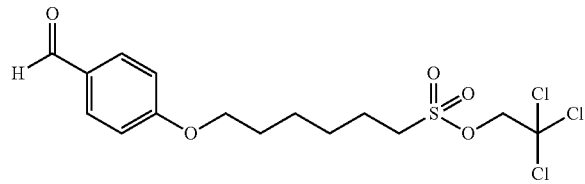 [SMILES: O=Cc1ccc(OCCCCCCS(=O)(=O)OCC(Cl)(Cl)Cl)cc1]

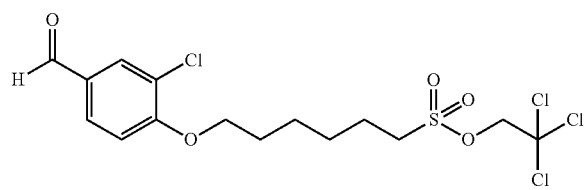 [SMILES: O=Cc1ccc(OCCCCCCS(=O)(=O)OCC(Cl)(Cl)Cl)c(Cl)c1]

To a solution of N-chlorosuccinamide (1.81 g, 13.6 mmol) in acetonitrile (8 mL) and HCl (2 M, 2 mL), S-(6-(4-formylphenoxy)hexyl) ethanethioate (1.0 g, 3.6 mmol) in acetonitrile (5 mL) was added dropwise over 5 min. The mixture was stirred for 30 min at RT, diluted with ether, and washed with brine. The organic layer was concentrated and redissolved in THF (20 mL). Trichloroethanol (3.5 mL) and 2,6-lutidene (1.53 g, 14.3 mmol) was added, and the mixture was heated at 85° C. for 2 d. The reaction was cooled, diluted with ethyl acetate, and washed with HCl (1 M) and brine. The organic layers were combined, dried with sodium sulfate, filtered, concentrated, and purified with silica gel chromatography to afford a mixture of products (0.54 g, 36%) as a light brown solid. ESI MS m/z 417, 451 [M+H]$^+$.

Step 4. 2,2,2-trichloroethyl (Z)-6-(4-((8-benzyl-3-oxo-6-phenylimidazo[1,2-a]pyrazin-2(3H)-ylidene)methyl)-2-chlorophenoxy)hexane-1-sulfonate (JRW-0663)

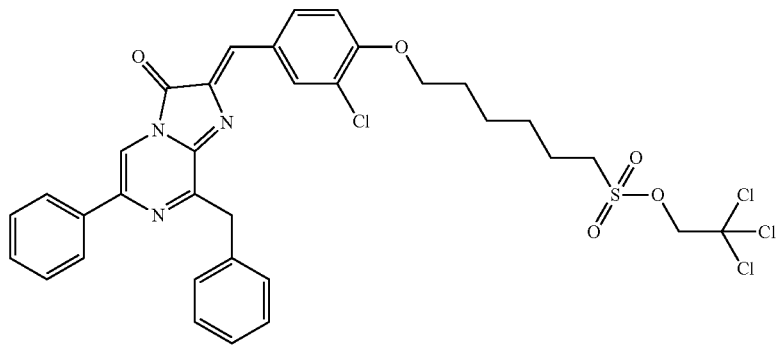 [SMILES: O=C1/C(=C/c2ccc(OCCCCCCS(=O)(=O)OCC(Cl)(Cl)Cl)c(Cl)c2)N=C2C(Cc3ccccc3)=NC(c3ccccc3)=CN12]

Following general procedure D, the mixture of 2,2,2-trichloroethyl 6-(4-formylphenoxy)hexane-1-sulfonate and 2,2,2-trichloroethyl 6-(2-chloro-4-formylphenoxy)hexane-1-sulfonate (92 mg, 0.22 mmol) was reacted with benzyl 2-((3-benzyl-5-phenylpyrazin-2-yl)amino)-2-(diethoxyphosphoryl)acetate (100 mg, 0.18 mmol) to afford the desired crude product (86 mg) as a red black solid. ESI MS m/z 734 [M+H]$^+$. Note: only 2,2,2-trichloroethyl 6-(2-chloro-4-formylphenoxy)hexane-1-sulfonate reacted under these reaction conditions.

Step 5. 2,2,2-trichloroethyl 6-(4-((8-benzyl-3-oxo-6-phenyl-3,7-dihydroimidazo[1,2-a]pyrazin-2-yl)methyl)-2-chlorophenoxy)hexane-1-sulfonate (JRW-0665)

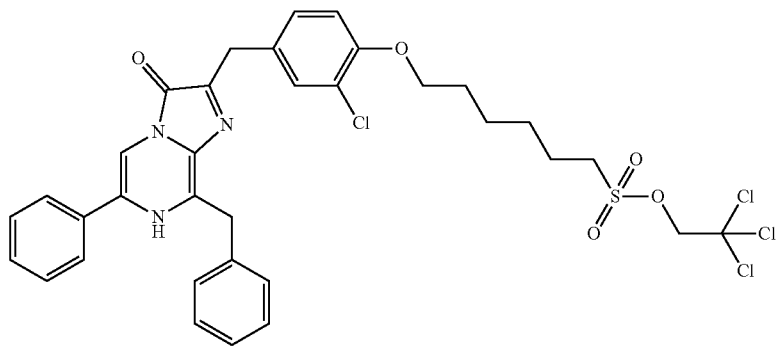 [SMILES: O=c1c(Cc2ccc(OCCCCCCS(=O)(=O)OCC(Cl)(Cl)Cl)c(Cl)c2)nc2c(Cc3ccccc3)[nH]c(-c3ccccc3)cn1-2]

Following general procedure E, 2,2,2-trichloroethyl (Z)-6-(4-((8-benzyl-3-oxo-6-phenylimidazo[1,2-a]pyrazin-2(3H)-ylidene)methyl)-2-chlorophenoxy)hexane-1-sulfonate (86 mg, 0.12 mmol) was reacted with sodium borohydride (13 mg, 0.35 mmol) to afford the desired product (73 mg, 55% over two steps) as an orange foam. $^1$H NMR (300 MHz, CD$_3$OD) δ 7.50-7.15 (m, 13H), 6.92-6.75 (m, 2H), 4.73 (s, 2H), 4.56 (s, 2H), 4.00-3.93 (m, 2H), 3.35-3.23 (m, 2H), 1.87-1.74 (m, 2H), 1.70-1.49 (m, 6H); ESI MS m/z 738 [M+H]+; HPLC 88.7% (AUC), T$_R$ 6.26 min; UV (MeOH) λ 428 nm, ε 6238.

Example 2 tert-butyl 6-(3-((8-benzyl-3-oxo-6-phenyl-3,7-dihydroimidazo[1,2-a]pyrazin-2-yl)methyl)phenoxy)hexanoate (JRW-0682)

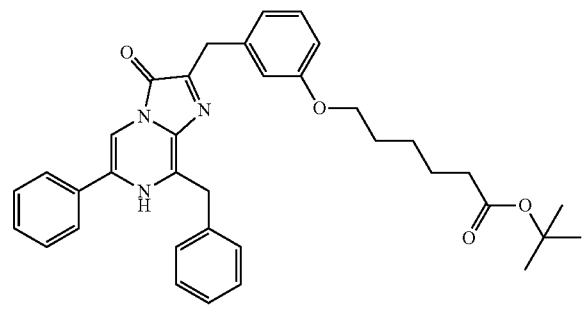 [SMILES: CC(C)(C)OC(=O)CCCCCOc1cccc(Cc2nc3c(Cc4ccccc4)[nH]c(-c4ccccc4)cn-3c2=O)c1]

Step 1. ethyl 6-(3-formylphenoxy)hexanoate (JRW-0669)

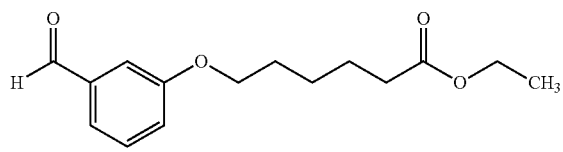 [SMILES: CCOC(=O)CCCCCOc1cccc(C=O)c1]

Following general procedure A, 3-hydroxybenzaldehyde (2.0 g, 16.4 mmol) was reacted with ethyl 6-bromohexanoate (7.3 g, 32.8 mmol) to afford the desired product (4.2 g, 97%) as a colorless oil. $^1$H NMR (300 MHz, CDCl$_3$) δ 9.96 (s, 1H), 7.46-7.42 (m, 2H), 7.37-7.35 (m, 1H), 7.18-7.12 (m, 1H), 4.13 (q, J=7.1, 2H), 4.01 (t, J=6.4, 2H), 2.33 (t, J=7.4, 2H), 1.91-1.42 (m, 6H), 1.25 (t, J=7.1 Hz, 3H); ESI MS m/z 265 [M+H]+.

Step 2. 6-(3-formylphenoxy)hexanoic acid (JRW-0672)

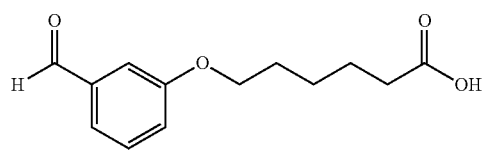 [SMILES: O=Cc1cccc(OCCCCCC(=O)O)c1]

Following general procedure B, ethyl 6-(3-formylphenoxy)hexanoate (4.0 g, 15.1 mmol) was reacted with sodium hydroxide (19.7 mL, 1 M, 19.7 mmol) to afford the desired product (3.6 g, quant) as a white solid. ESI MS m/z 237 [M+H]+.

Step 3. tert-butyl 6-(3-formylphenoxy)hexanoate (JRW-0675)

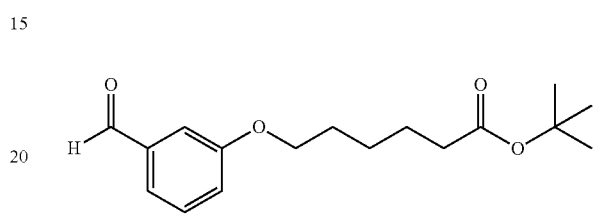

Following general procedure C, 6-(3-formylphenoxy)hexanoic acid (3.6 g, 15.2 mmol) was reacted with 1,1-di-tert-butoxy-N,N-dimethylmethanamine (4.65 g, 22.8 mmol) to afford the desired product (1.47 g, 33%) as a white solid. $^1$H NMR (300 MHz, CDCl$_3$) δ 9.96 (s, 1H), 7.47-7.33 (m, 3H), 7.21-7.09 (m, 1H), 4.01 (t, J=6.4, 2H), 2.25 (t, J=7.3, 2H), 1.88-1.74 (m, 2H), 1.74-1.58 (m, 2H), 1.57-1.38 (m, 11H). ESI MS m/z 293 [M+H]+.

Step 4. tert-butyl (Z)-6-(3-((8-benzyl-3-oxo-6-phenylimidazo[1,2-a]pyrazin-2(3H)-ylidene)methyl)phenoxy)hexanoate (JRW-0678)

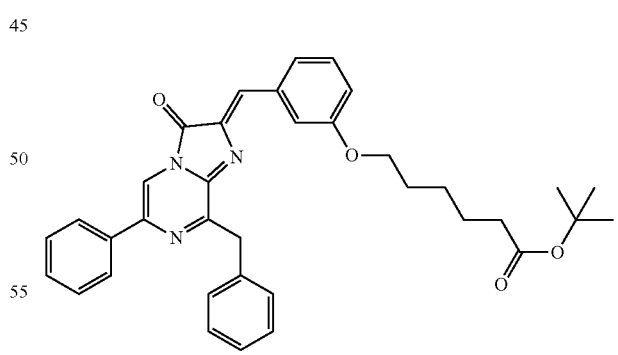

Following general procedure D, tert-butyl 6-(3-formylphenoxy)hexanoate (80 mg, 0.27 mmol) was reacted with benzyl 2-((3-benzyl-5-phenylpyrazin-2-yl)amino)-2-(diethoxyphosphoryl)acetate (100 mg, 0.18 mmol) to afford the desired crude product (89 mg) as a red black solid. ESI MS m/z 684 [M+H]+.

Step 5. tert-butyl 6-(3-((8-benzyl-3-oxo-6-phenyl-3,7-dihydroimidazo[1,2-a]pyrazin-2-yl)methyl)phenoxy)hexanoate (JRW-0682)

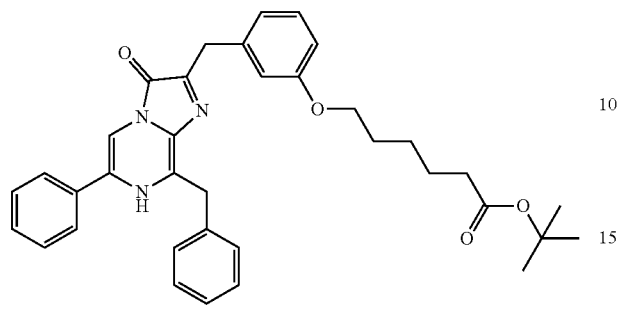

Following general procedure E, tert-butyl (Z)-6-(3-((8-benzyl-3-oxo-6-phenylimidazo[1,2-a]pyrazin-2(3H)-ylidene)methyl)phenoxy)hexanoate (89 mg, 0.15 mmol) was reacted with sodium borohydride (29 mg, 0.77 mmol) to afford the desired product (88 mg, 84% over two steps) as an orange foam. Note: isolated material was not pure, impurities present. $^1$H NMR (300 MHz, CD$_2$Cl$_2$) δ 7.50-7.21 (m, 13H), 6.92-6.75 (m, 2H), 4.39 (s, 2H), 4.10 (s, 2H), 3.93-3.81 (m, 2H), 2.27-2.15 (m, 2H), 1.87-1.40 (m, 12H); ESI MS m/z 578 [M+H]+; HPLC 89.6% (AUC), T$_R$ 6.14 min; UV (MeOH) λ 433 nm, ε 3462.

Example 3

6-(3-((8-benzyl-3-oxo-6-phenyl-3,7-dihydroimidazo[1,2-a]pyrazin-2-yl)methyl)phenoxy)hexanoic acid (JRW-0684)

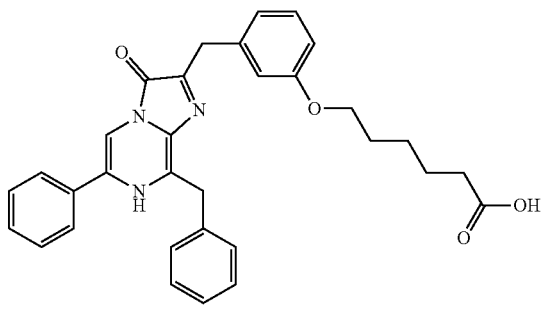 [SMILES: O=C(O)CCCCCOc1cccc(Cc2nc3c(Cc4ccccc4)[nH]c(-c4ccccc4)cn-3c2=O)c1]

Following general procedure F, tert-butyl 6-(3-((8-benzyl-3-oxo-6-phenyl-3,7-dihydroimidazo[1,2-a]pyrazin-2-yl)methyl)phenoxy)hexanoate (80 mg, 0.14 mmol) was reacted with trifluoroacetic acid (1 mL) to afford the desired product (32 mg, 44%) as an orange solid. $^1$H NMR (300 MHz, CD$_2$Cl$_2$) δ 7.76-7.12 (m, 12H), 6.96-6.88 (m, 2H), 6.75-6.68 (m, 1H), 4.36 (s, 2H), 4.12 (s, 2H), 3.92 (t, J=6.4, 2H), 2.28 (t, J=7.3, 2H), 1.82-1.39 (m, 6H); ESI MS m/z 522 [M+H]+; HPLC 97.6% (AUC), T$_R$ 4.52 min; UV (MeOH) λ 431 nm, ε 8435.

Example 4

8-benzyl-2-(3-((6-bromohexyl)oxy)benzyl)-6-phenylimidazo[1,2-a]pyrazin-3(7H)-one (JRW-0692)

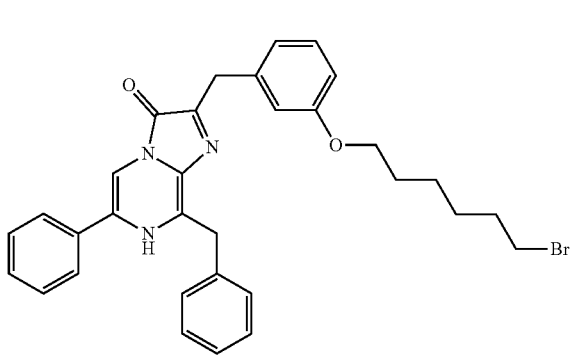 [SMILES: O=c1c(Cc2cccc(OCCCCCCBr)c2)nc2c(Cc3ccccc3)[nH]c(-c3ccccc3)cn1-2]

Step 1. 3-((6-bromohexyl)oxy)benzaldehyde (JRW-0690)

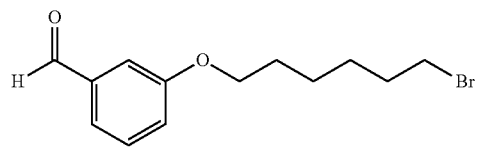 [SMILES: O=Cc1cccc(OCCCCCCBr)c1]

Following general procedure A, 3-hydroxybenzaldehyde (2.0 g, 16.4 mmol) was reacted with 1,6-dibromohexane (8.0 g, 32.8 mmol) to afford the desired product (3.4 g, 73%) as a colorless oil. ESI MS m/z 285 [M+H]$^+$.

Step 2. (Z)-8-benzyl-2-(3-((6-bromohexyl)oxy)benzylidene)-6-phenylimidazo[1,2-a]pyrazin-3(2H)-one (JRW-0691)

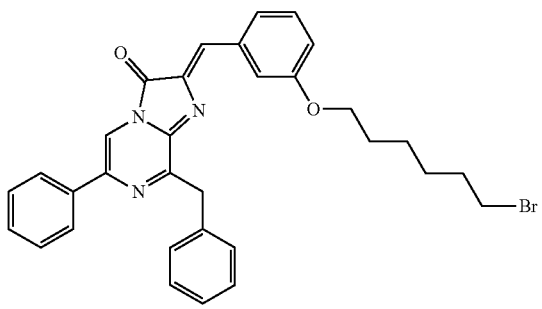 [SMILES: O=C1/C(=C/c2cccc(OCCCCCCBr)c2)N=C2C(Cc3ccccc3)=NC(c3ccccc3)=CN12]

Following general procedure D, 3-((6-bromohexyl)oxy)benzaldehyde (78 mg, 0.27 mmol) was reacted with benzyl 2-((3-benzyl-5-phenylpyrazin-2-yl)amino)-2-(diethoxyphosphoryl)acetate (100 mg, 0.18 mmol) to afford the desired crude product (93 mg) as a red black solid. ESI MS m/z 568 [M+H]$^+$.

Step 3. 8-benzyl-2-(3-((6-bromohexyl)oxy)benzyl)-6-phenylimidazo[1,2-a]pyrazin-3(7H)-one (JRW-0692)

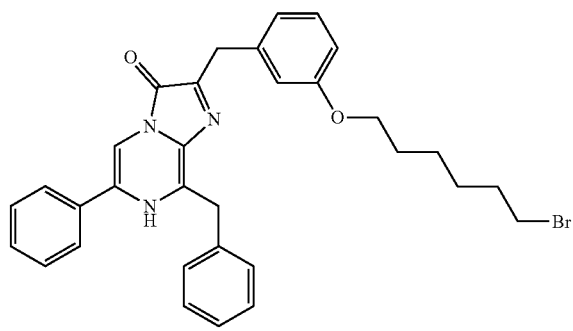 [SMILES: O=c1c(Cc2cccc(OCCCCCCBr)c2)nc2c(Cc3ccccc3)[nH]c(-c3ccccc3)cn1-2]

Following general procedure E, (Z)-8-benzyl-2-(3-((6-bromohexyl)oxy)benzylidene)-6-phenylimidazo[1,2-a]pyrazin-3(2H)-one (93 mg, 0.16 mmol) was reacted with sodium borohydride (31 mg, 0.82 mmol) to afford the desired product (57 mg, 56% over two steps) as an orange foam. $^1$H NMR (300 MHz, CD$_2$Cl$_2$) δ 7.52-70.3 (m, 12H), 6.98-6.80 (m, 2H), 6.72-6.62 (m, 1H), 4.39 (s, 2H), 4.08 (s, 2H), 3.92-3.78 (m, 2H), 3.41 (t, J=6.8, 2H), 1.96-1.65 (m, 4H), 1.52-1.38 (s, 4H); ESI MS m/z 570 [M+H]+; HPLC 97.3% (AUC), T$_R$ 6.11 min; UV (MeOH) λ 425 nm, ε 7250.

Example 5 sodium 6-(3-((8-benzyl-3-oxo-6-phenyl-3,7-dihydroimidazo[1,2-a]pyrazin-2-yl)methyl)phenoxy)hexane-1-sulfonate (JRW-0703)

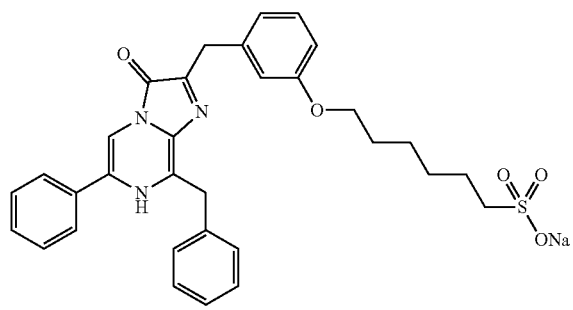

Step 1. sodium 6-(3-formylphenoxy)hexane-1-sulfonate (JRW-0698)

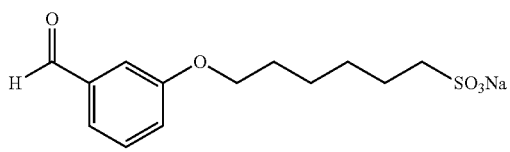

Following general procedure G, 3-((6-bromohexyl)oxy)benzaldehyde (200 mg, 0.70 mmol) was reacted with sodium sulfite (442 mg, 3.5 mmol) to afford crude product (375 mg) as a white solid. $^1$H NMR (300 MHz, CD$_3$OD) δ 9.93 (s, 1H), 7.52-7.40 (m, 3H), 7.28-7.20 (m, 1H), 4.06 (t, J=6.4, 2H), 2.88-2.78 (m, 2H), 1.89-1.75 (m, 4H), 1.60-1.45 (m, 4H); ESI MS m/z 285 [M–H–Na]–.

Step 2. sodium (Z)-6-(3-((8-benzyl-3-oxo-6-phenylimidazo[1,2-a]pyrazin-2(3H)-ylidene)methyl)phenoxy)hexane-1-sulfonate (JRW-0702)

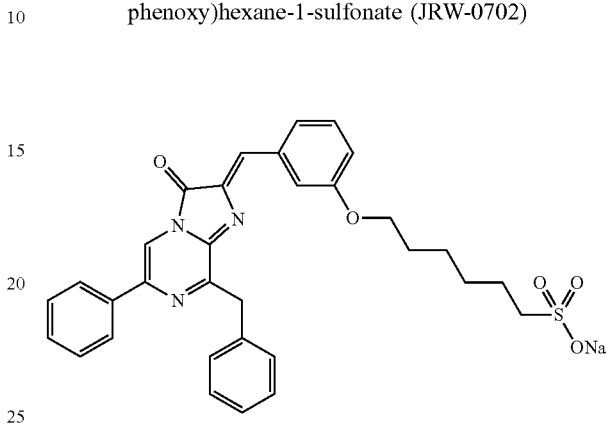

Following general procedure H, sodium 6-(3-formylphenoxy)hexane-1-sulfonate (84 mg, 0.28 mmol) was reacted with benzyl 2-((3-benzyl-5-phenylpyrazin-2-yl)amino)-2-(diethoxyphosphoryl)acetate (100 mg, 0.18 mmol) to afford crude product (66 mg) as a red black solid.

Step 3. sodium 6-(3-((8-benzyl-3-oxo-6-phenyl-3,7-dihydroimidazo[1,2-a]pyrazin-2-yl)methyl)phenoxy)hexane-1-sulfonate (JRW-0703)

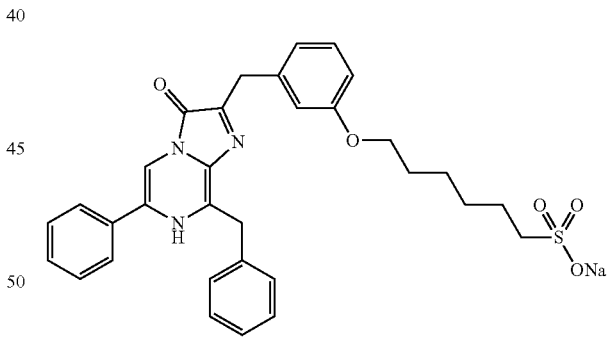

Following general procedure I, sodium (Z)-6-(3-((8-benzyl-3-oxo-6-phenylimidazo[1,2-a]pyrazin-2(3H)-ylidene)methyl)phenoxy)hexane-1-sulfonate (66 mg, 0.11 mmol) was reacted with sodium borohydride (21 mg, 0.56 mmol) to afford the desired product (17 mg, 16% over two steps) as a yellow solid. $^1$H NMR (300 MHz, CD$_3$OD) δ 7.80-7.57 (m, 2H), 7.50-7.36 (m, 5H), 7.33-7.11 (m, 5H), 6.92-6.85 (s, 2H), 6.75-6.67 (m, 1H), 4.41 (s, 2H), 4.13 (s, 2H), 3.99-3.87 (s, 2H), 2.83-2.73 (m, 2H), 1.89-1.68 (m, 4H), 1.54-1.41 (m, 4H); ESI MS m/z 572 [M+H–Na]+; HPLC 96.9% (AUC), T$_R$ 4.78 min; UV (MeOH) λ 430 nm, ε 5824.

Example 6 tert-butyl 4-(3-((8-benzyl-3-oxo-6-phenyl-3,7-dihydroimidazo[1,2-a]pyrazin-2-yl)methyl)phenoxy)butanoate (JRW-0714)

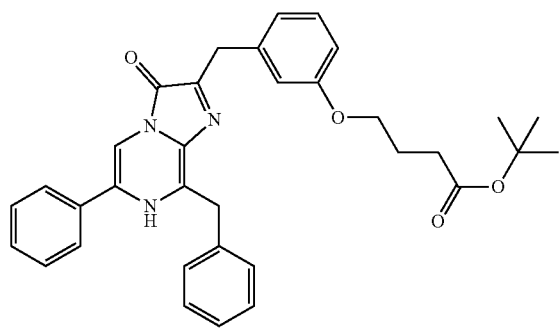 [SMILES: CC(C)(C)OC(=O)CCCOc1cccc(Cc2nc3c(Cc4ccccc4)[nH]c(-c4ccccc4)cn-3c2=O)c1]

Step 1. methyl 4-(3-formylphenoxy)butanoate (JRW-0688)

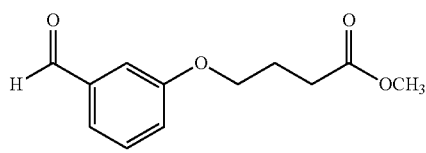 [SMILES: COC(=O)CCCOc1cccc(C=O)c1]

Following general procedure A, 3-hydroxybenzaldehyde (2.0 g, 16.4 mmol) was reacted with methyl 4-bromobutanoate (3.56 g, 19.7 mmol) to afford the desired product (3.52 g, 96%) as a colorless oil. $^1$H NMR (300 MHz, CDCl$_3$) δ 10.65-10.62 (m, 1H), 8.17-8.02 (m, 3H), 7.87-7.79 (m, 1H), 4.80-7.69 (m, 2H), 4.37 (s, 3H), 3.26-3.15 (m, 2H), 2.88-2.72 (m, 2H).

Step 2. 4-(3-formylphenoxy)butanoic acid (JRW-0689)

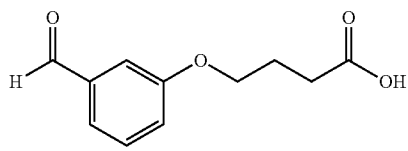 [SMILES: O=Cc1cccc(OCCCC(=O)O)c1]

Following general procedure B, methyl 4-(3-formylphenoxy)butanoate (3.5 g, 15.8 mmol) was reacted with sodium hydroxide (20.5 mL, 1 M, 20.5 mmol) to afford the desired product (2.64 g, 80%) as a white solid. ESI MS m/z 209 [M+H]$^+$.

Step 3. tert-butyl 4-(3-formylphenoxy)butanoate (JRW-709)

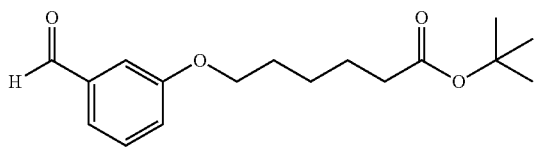 [SMILES: CC(C)(C)OC(=O)CCCCCOc1cccc(C=O)c1]

Following general procedure C, 4-(3-formylphenoxy)butanoic acid (0.5 g, 2.40 mmol) was reacted with 1,1-di-tert-butoxy-N,N-dimethylmethanamine (0.98 g, 4.80 mmol) to afford the desired product (0.16 g, 25%) as a colorless oil. $^1$H NMR (300 MHz, CDCl$_3$) δ 9.96 (s, 1H), 7.54-7.32 (m, 3H), 7.23-7.11 (m, 1H), 4.05 (t, J=6.2, 2H), 2.43 (t, J=7.3, 2H), 2.21-2.01 (m, 2H), 1.45 (s, 9H); ESI MS m/z 265 [M+H]$^+$.

Step 4. tert-butyl (Z)-4-(3-((8-benzyl-3-oxo-6-phenylimidazo[1,2-a]pyrazin-2(3H)-ylidene)methyl)phenoxy)butanoate (JRW-0712)

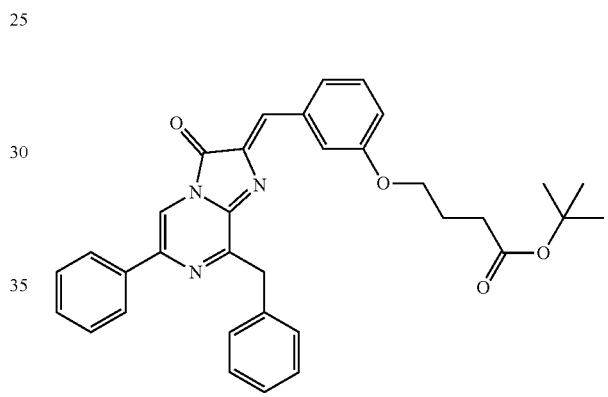

Following general procedure D, tert-butyl 4-(3-formylphenoxy)butanoate (148 mg, 0.60 mmol) was reacted with methyl 2-((3-benzyl-5-phenylpyrazin-2-yl)amino)-2-(diethoxyphosphoryl)acetate (175 mg, 0.37 mmol) to afford the desired crude product (180 mg) as a red black solid. ESI MS m/z 580 [M+H]$^+$

Step 5. tert-butyl 4-(3-((8-benzyl-3-oxo-6-phenyl-3,7-dihydroimidazo[1,2-a]pyrazin-2-yl)methyl)phenoxy)butanoate (JRW-0714)

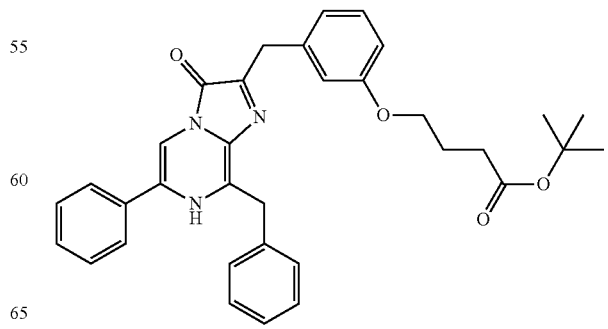

Following general procedure E, tert-butyl (Z)-4-(3-((8-benzyl-3-oxo-6-phenylimidazo[1,2-a]pyrazin-2(3H)-ylidene)methyl)phenoxy)butanoate (180 mg, 0.33 mmol) was reacted with sodium borohydride (62 mg, 1.64 mmol) to afford the desired product (110 mg, 54% over two steps) as an orange foam. $^1$H NMR (300 MHz, CD$_3$OD) δ 7.75-7.56 (m, 3H), 7.51-7.36 (m, 5H), 7.32-7.10 (m, 4H), 6.93-6.88 (m, 2H), 6.75-6.69 (m, 1H), 4.40 (s, 2H), 4.13 (s, 2H), 3.93 (t, J=6.2, 2H), 2.36 (t, J=7.3, 2H), 2.03-1.92 (m, 2H), 1.39 (s, 9H); ESI MS m/z 550 [M+H]+; HPLC 99.9% (AUC), T$_R$ 5.80 min; UV (MeOH) λ 433 nm, ε 9872.

Example 7 sodium 3-(3-((8-benzyl-3-oxo-6-phenyl-3,7-dihydroimidazo[1,2-a]pyrazin-2-yl)methyl)phenoxy)propane-1-sulfonate (JRW-0713)

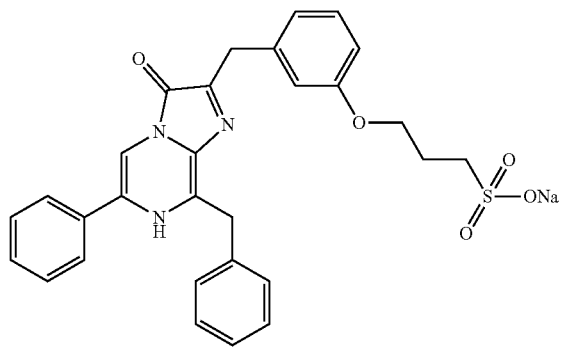

Step 1. 3-(3-formylphenoxy)propane-1-sulfonic acid (JRW-0671)

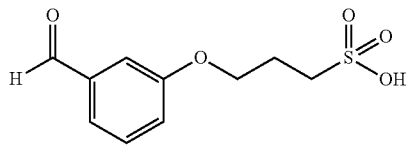 [SMILES: O=Cc1cccc(OCCCS(=O)(=O)O)c1]

Following general procedure A, 3-hydroxybenzaldehyde (1.0 g, 8.2 mmol) was reacted with 1,2-oxathiolane 2,2-dioxide (2.0 g, 16.4 mmol) to afford crude product (3.2 g) as a white solid. Note: isolated material was not pure, impurities present. $^1$H NMR (300 MHz, CD$_3$OD) δ 9.94 (s, 1H), 7.58-7.40 (m, 3H), 7.34-7.20 (m, 1H), 4.19 (t, J=6.3, 2H), 3.34-3.28 (m, 2H), 3.04-2.95 (m, 2H), 2.34-2.21 (m, 2H); ESI MS m/z 245 [M+H]+.

Step 2. sodium (Z)-3-(3-((8-benzyl-3-oxo-6-phenylimidazo[1,2-a]pyrazin-2(3H)-ylidene)methyl)phenoxy)propane-1-sulfonate (JRW-0711)

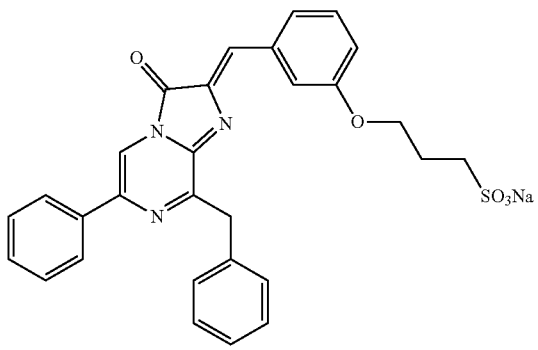

Following general procedure H, 3-(3-formylphenoxy)propane-1-sulfonic acid (179 mg, 0.73 mmol) was reacted with benzyl 2-((3-benzyl-5-phenylpyrazin-2-yl)amino)-2-(diethoxyphosphoryl)acetate (200 mg, 0.36 mmol) to afford crude product (410 mg) as a red black solid.

Step 3. sodium 3-(3-((8-benzyl-3-oxo-6-phenyl-3,7-dihydroimidazo[1,2-a]pyrazin-2-yl)methyl)phenoxy)propane-1-sulfonate (JRW-0713)

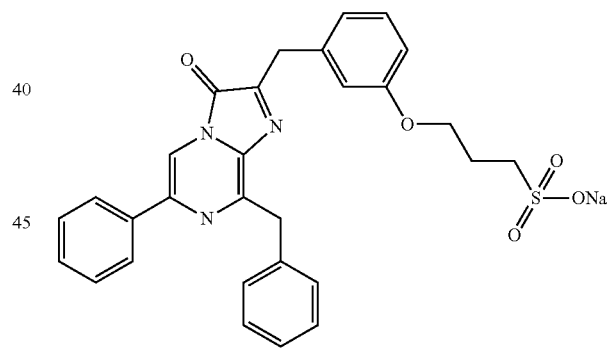

Following general procedure I, sodium (Z)-3-(3-((8-benzyl-3-oxo-6-phenylimidazo[1,2-a]pyrazin-2(3H)-ylidene)methyl)phenoxy)propane-1-sulfonate (0.36 mmol) was reacted with sodium borohydride (69 mg, 1.83 mmol) to afford the desired product (46 mg, 23% over two steps) as an orange brown solid. Note: isolated material was not pure, impurities present. $^1$H NMR (300 MHz, CD$_3$OD) δ 7.81-7.60 (s, 2H), 7.51-7.37 (m, 5H), 7.37-7.09 (m, 5H), 6.96-6.85 (m, 2H), 6.84-6.73 (m, 1H), 4.55 (s, 2H), 4.42 (s, 2H), 4.20-3.97 (m, 2H), 3.03-2.90 (m, 2H), 2.30-2.16 (m, 2H); ESI MS m/z 530 [M+H−Na]+; HPLC 96.5% (AUC), T$_R$ 3.35 min; UV (MeOH) λ 431 nm, ε 4746.

Example 8

4-(3-((8-benzyl-3-oxo-6-phenyl-3,7-dihydroimidazo[1,2-a]pyrazin-2-yl)methyl)phenoxy)butanoic acid (JRW-0716)

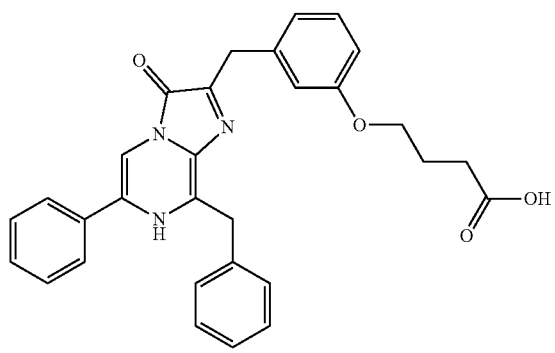 [SMILES: O=C(O)CCCOc1cccc(Cc2nc3c(Cc4ccccc4)[nH]c(-c4ccccc4)cn-3c2=O)c1]

Following general procedure F, tert-butyl 4-(3-((8-benzyl-3-oxo-6-phenyl-3,7-dihydroimidazo[1,2-a]pyrazin-2-yl)methyl)phenoxy)butanoate (100 mg, 0.18 mmol) was reacted with trifluoroacetic acid (1 mL) to afford the desired product (82 mg, 91%) as an orange solid. $^1$H NMR (300 MHz, CD$_3$OD) δ 7.80-7.58 (m, 3H), 7.51-7.37 (m, 5H), 7.35-7.12 (m, 4H), 6.95-6.87 (m, 2H), 6.78-6.70 (m, 1H), 4.41 (s, 2H), 4.13 (s, 2H), 3.96 (t, J=6.2, 2H), 2.44 (t, J=7.3, 2H), 2.10-1.93 (m, 2H); ESI MS m/z 494 [M+H]+; HPLC 98.4% (AUC), T$_R$ 4.99 min; UV (MeOH) λ 431 nm, ε 14786.

Example 9 tert-butyl 8-(3-((8-benzyl-3-oxo-6-phenyl-3,7-dihydroimidazo[1,2-a]pyrazin-2-yl)methyl)phenoxy)octanoate (JRW-0719)

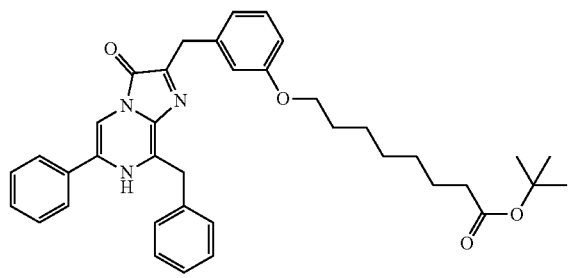 [SMILES: CC(C)(C)OC(=O)CCCCCCCOc1cccc(Cc2nc3c(Cc4ccccc4)[nH]c(-c4ccccc4)cn-3c2=O)c1]

Step 1. ethyl 8-(3-formylphenoxy)octanoate (JRW-0697)

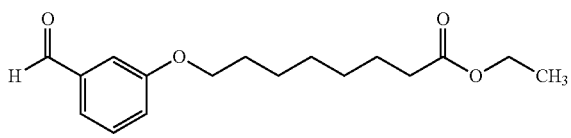 [SMILES: CCOC(=O)CCCCCCCOc1cccc(C=O)c1]

Following general procedure A, 3-hydroxybenzaldehyde (1.0 g, 8.2 mmol) was reacted with ethyl 8-bromooctanoate (2.47 g, 9.8 mmol) to afford the desired product (2.07 g, 87%) as a colorless oil. $^1$H NMR (300 MHz, CDCl$_3$) δ 9.97 (s, 1H), 7.47-7.36 (m, 3H), 7.20-7.13 (m, 1H), 4.12 (q, J=7.1, 2H), 4.01 (t, J=6.5, 2H), 2.29 (t, J=7.5, 2H), 1.87-1.72 (m, 2H), 1.71-1.55 (m, 2H), 1.54-1.30 (m, 6H), 1.25 (t, J=7.1 Hz, 3H).

Step 2. 8-(3-formylphenoxy)octanoic acid (JRW-0699)

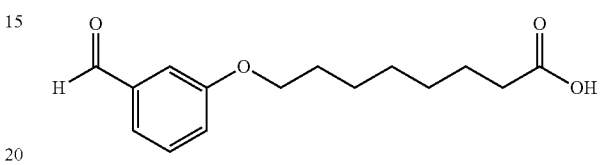

Following general procedure B, ethyl 8-(3-formylphenoxy)octanoate (2.07 g, 7.1 mmol) was reacted with sodium hydroxide (9.2 mL, 1 M, 9.2 mmol) to afford the desired product (1.8 g, 96%) as a white solid. ESI MS m/z 265 [M+H]+.

Step 3. tert-butyl 8-(3-formylphenoxy)octanoate (JRW-710)

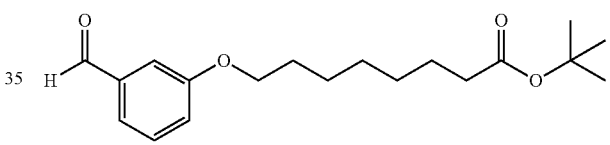

Following general procedure C, 8-(3-formylphenoxy)octanoic acid (0.5 g, 1.9 mmol) was reacted with 1,1-di-tert-butoxy-N,N-dimethylmethanamine (0.77 g, 3.8 mmol) to afford the desired product (0.15 g, 25%) as a colorless oil. $^1$H NMR (300 MHz, CDCl$_3$) δ 9.97 (s, 1H), 7.47-7.35 (m, 3H), 7.21-7.12 (m, 1H), 4.01 (t, J=6.5, 2H), 2.21 (t, J=7.4, 2H), 1.88-1.72 (m, 2H), 1.71-1.25 (m, 17H); ESI MS m/z 321 [M+H]+.

Step 4. tert-butyl (Z)-8-(3-((8-benzyl-3-oxo-6-phenylimidazo[1,2-a]pyrazin-2(3H)-ylidene)methyl)phenoxy)octanoate (JRW-0717)

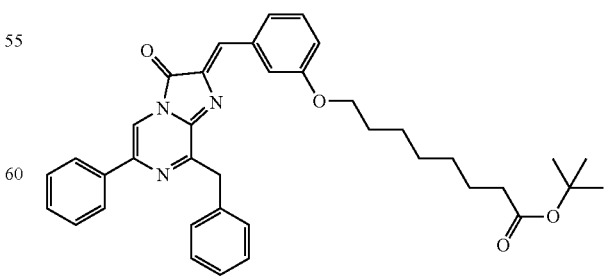

Following general procedure D, tert-butyl 8-(3-formylphenoxy)octanoate (141 mg, 0.44 mmol) was reacted with methyl 2-((3-benzyl-5-phenylpyrazin-2-yl)amino)-2-(diethoxyphosphoryl)acetate (200 mg, 0.37 mmol) to afford the desired crude product (145 mg) as a red black solid.

Step 5. tert-butyl 8-(3-((8-benzyl-3-oxo-6-phenyl-3,7-dihydroimidazo[1,2-a]pyrazin-2-yl)methyl)phenoxy)octanoate (JRW-0719)

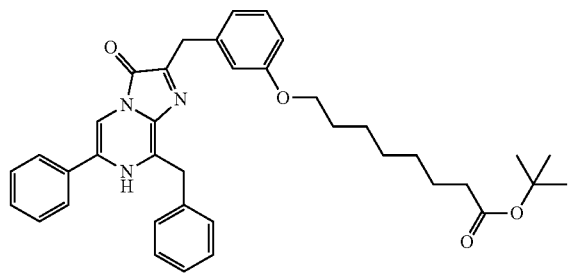 [SMILES: CC(C)(C)OC(=O)CCCCCCCOc1cccc(Cc2nc3c(Cc4ccccc4)[nH]c(-c4ccccc4)cn-3c2=O)c1]

Following general procedure E, tert-butyl (Z)-8-(3-((8-benzyl-3-oxo-6-phenylimidazo[1,2-a]pyrazin-2(3H)-ylidene)methyl)phenoxy)octanoate (145 mg, 0.24 mmol) was reacted with sodium borohydride (45 mg, 1.20 mmol) to afford the desired product (94 mg, 42% over two steps) as an orange foam. $^1$H NMR (300 MHz, CD$_3$OD) δ 7.75-7.59 (m, 3H), 7.50-7.35 (m, 5H), 7.33-7.11 (m, 4H), 6.93-6.86 (m, 2H), 6.74-6.68 (m, 1H), 4.40 (s, 2H), 4.13 (s, 2H), 3.90 (t, J=6.4, 2H), 2.18 (t, J=7.3, 2H), 1.80-1.24 (m, 19H); ESI MS m/z 606 [M+H]+; HPLC>99% (AUC), $T_R$ 7.82 min; UV (MeOH) λ 430 nm, ε 8272.

Example 10

8-benzyl-2-(4-((6-bromohexyl)oxy)-3-chlorobenzyl)-6-phenylimidazo[1,2-a]pyrazin-3(7H)-one (JRW-0720)

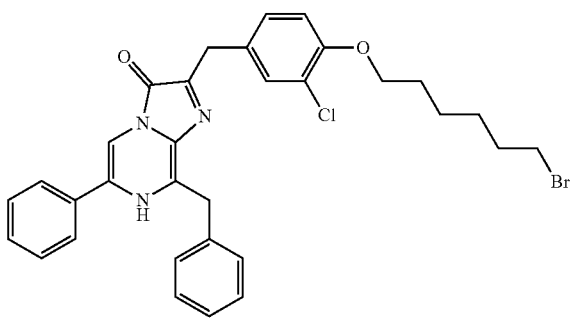 [SMILES: O=c1c(Cc2ccc(OCCCCCCBr)c(Cl)c2)nc2c(Cc3ccccc3)[nH]c(-c3ccccc3)cn1-2]

Step 1. 4-((6-bromohexyl)oxy)-3-chlorobenzaldehyde (JRW-0704)

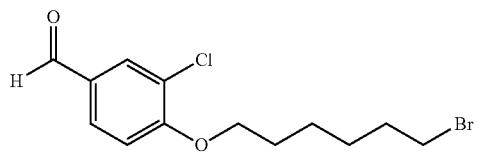 [SMILES: O=Cc1ccc(OCCCCCCBr)c(Cl)c1]

Following general procedure A, 3-chloro-4-hydroxybenzaldehyde (1.0 g, 6.4 mmol) was reacted with 1,6-dibromohexane (2.34 g, 9.6 mmol) to afford the desired product (1.2 g, 59%) as a colorless oil. $^1$H NMR (300 MHz, CDCl$_3$) δ 9.86 (s, 1H), 7.90 (d, J=2.0, 1H), 7.75 (dd, J=2.0, 8.5, 1H), 7.01 (t, J=8.5, 1H), 4.13 (t, J=6.3, 3H), 3.43 (t, J=6.7, 3H), 2.00-1.80 (m, 4H), 1.66-1.48 (m, 4H); ESI MS m/z 319 [M+H]+.

Step 2. (Z)-8-benzyl-2-(4-((6-bromohexyl)oxy)-3-chlorobenzylidene)-6-phenylimidazo[1,2-a]pyrazin-3(2H)-one (JRW-0718)

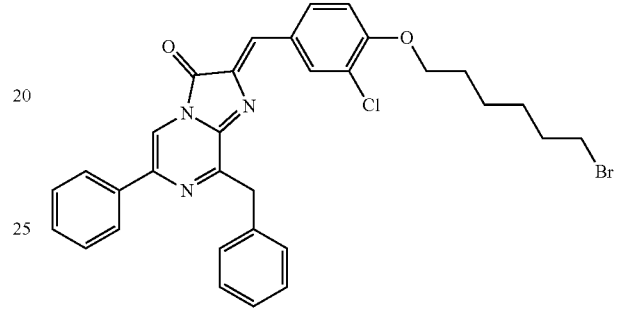

Following general procedure D, 4-((6-bromohexyl)oxy)-3-chlorobenzaldehyde (53 mg, 0.16 mmol) was reacted with methyl 2-((3-benzyl-5-phenylpyrazin-2-yl)amino)-2-(diethoxyphosphoryl)acetate (75 mg, 0.14 mmol) to afford the desired crude product (63 mg) as a red black solid. ESI MS m/z 602 [M+H]+.

Step 3. 8-benzyl-2-(4-((6-bromohexyl)oxy)-3-chlorobenzyl)-6-phenylimidazo[1,2-a]pyrazin-3(7H)-one (JRW-0720)

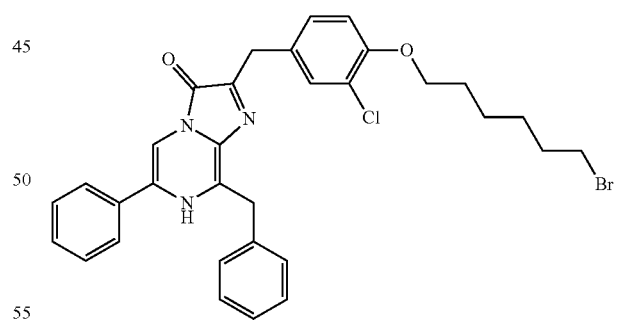

Following general procedure E, (Z)-8-benzyl-2-(4-((6-bromohexyl)oxy)-3-chlorobenzylidene)-6-phenylimidazo[1,2-a]pyrazin-3(2H)-one (63 mg, 0.10 mmol) was reacted with sodium borohydride (20 mg, 0.52 mmol) to afford the desired product (25 mg, 30% over two steps) as an orange foam. $^1$H NMR (300 MHz, CD$_3$OD) δ 7.78-7.58 (m, 3H), 7.54-7.15 (m, 10H), 6.97-6.91 (m, 1H), 4.40 (s, 2H), 4.08 (s, 2H), 3.99 (t, J=6.2, 2H), 3.42 (t, J=6.7, 2H), 1.91-1.70 (m, 4H), 1.60-1.43 (m, 4H); ESI MS m/z 606 [M+2+H]+; HPLC 98.1% (AUC), $T_R$ 7.63 min; UV (MeOH) λ 433 nm, ε 9173.

Example 11

8-(3-(((8-benzyl-3-oxo-6-phenyl-3,7-dihydroimidazo[1,2-a]pyrazin-2-yl)methyl)phenoxy)octanoic acid (JRW-0722)

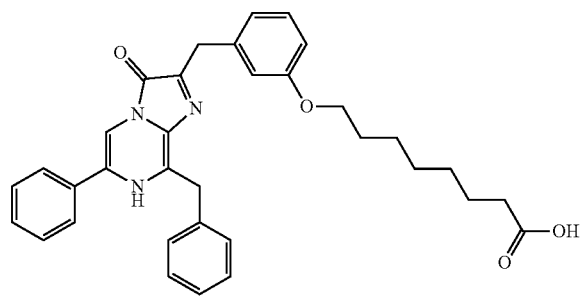 [SMILES: O=C(O)CCCCCCCOc1cccc(Cc2nc3c(Cc4ccccc4)[nH]c(-c4ccccc4)cn-3c2=O)c1]

Following general procedure F, tert-butyl 8-(3-((8-benzyl-3-oxo-6-phenyl-3,7-dihydroimidazo[1,2-a]pyrazin-2-yl)methyl)phenoxy)octanoate (85 mg, 0.14 mmol) was reacted with trifluoroacetic acid (1 mL) to afford the desired product (75 mg, 97%) as an orange solid. $^1$H NMR (300 MHz, CD$_3$OD) δ 7.80-7.55 (m, 3H), 7.54-7.34 (m, 5H), 7.34-7.07 (m, 4H), 6.95-6.86 (m, 2H), 6.74-6.68 (m, 1H), 4.40 (s, 2H), 4.13 (s, 2H), 3.90 (t, J=6.3, 2H), 2.25 (t, J=7.2, 2H), 1.81-1.24 (m, 10H); ESI MS m/z 550 [M+H]+; HPLC 99.5% (AUC), T$_R$ 5.96 min; UV (MeOH) λ 432 nm, ε 9798.

Example 12 tert-butyl 6-(4-((8-benzyl-3-oxo-6-phenyl-3,7-dihydroimidazo[1,2-a]pyrazin-2-yl)methyl)-2-chlorophenoxy)hexanoate (JRW-0725)

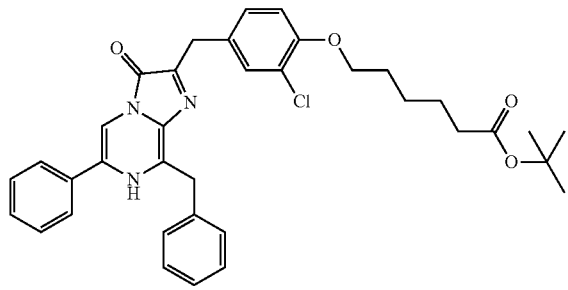 [SMILES: CC(C)(C)OC(=O)CCCCCOc1ccc(Cc2nc3c(Cc4ccccc4)[nH]c(-c4ccccc4)cn-3c2=O)cc1Cl]

Step 1. ethyl 6-(2-chloro-4-formylphenoxy)hexanoate (JRW-0705)

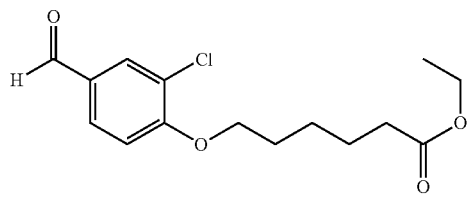 [SMILES: CCOC(=O)CCCCCOc1ccc(C=O)cc1Cl]

Following general procedure A, 3-chloro-4-hydroxybenzaldehyde (1.0 g, 6.4 mmol) was reacted with ethyl 6-bromohexanoate (2.14 g, 9.6 mmol) to afford the desired product (0.55 g, 29%) as a colorless oil.

Step 2. 6-(2-chloro-4-formylphenoxy)hexanoic acid (JRW-0707)

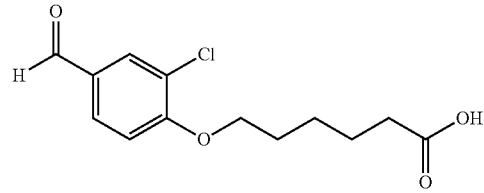 [SMILES: O=Cc1ccc(OCCCCCC(=O)O)c(Cl)c1]

Following general procedure B, ethyl 6-(2-chloro-4-formylphenoxy)hexanoate (0.55 g, 1.8 mmol) was reacted with sodium hydroxide (1.2 mL, 2 M, 2.4 mmol) to afford the desired product (0.43 g) as a white solid. ESI MS m/z 271 [M+H]+.

Step 3. tert-butyl 6-(2-chloro-4-formylphenoxy)hexanoate (JRW-0721)

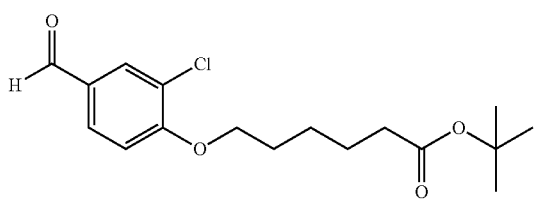 [SMILES: CC(C)(C)OC(=O)CCCCCOc1ccc(C=O)cc1Cl]

Following general procedure C, 6-(2-chloro-4-formylphenoxy)hexanoic acid (0.43 g, 1.6 mmol) was reacted with 1,1-di-tert-butoxy-N,N-dimethylmethanamine (0.65 g, 3.2 mmol) to afford the desired product (95 mg, 18%) as a white solid. $^1$H NMR (300 MHz, CDCl$_3$) δ 9.84 (s, 1H), 7.92-7.87 (m, 1H), 7.77-7.71 (m, 1H), 7.04-6.97 (m, 1H), 4.12 (t, J=5.3, 2H), 2.26 (t, J=6.3, 2H), 1.96-1.84 (m, 2H), 1.79-1.37 (m, 13H).

Step 4. tert-butyl (Z)-6-(4-((8-benzyl-3-oxo-6-phenylimidazo[1,2-a]pyrazin-2(3H)-ylidene)methyl)-2-chlorophenoxy)hexanoate (JRW-0724)

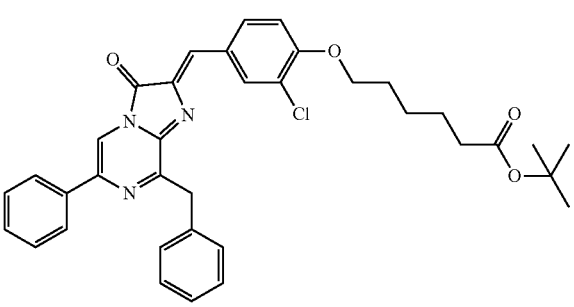 [SMILES: CC(C)(C)OC(=O)CCCCCOc1ccc(/C=C2\N=C3C(Cc4ccccc4)=NC(c4ccccc4)=CN3C2=O)cc1Cl]

Following general procedure D, tert-butyl 6-(2-chloro-4-formylphenoxy)hexanoate (104 mg, 0.32 mmol) was reacted with methyl 2-((3-benzyl-5-phenylpyrazin-2-yl)amino)-2-(diethoxyphosphoryl)acetate (150 mg, 0.32 mmol) to afford the desired crude product (180 mg) as a red black solid.

Step 5. tert-butyl 6-(4-((8-benzyl-3-oxo-6-phenyl-3,7-dihydroimidazo[1,2-a]pyrazin-2-yl)methyl)-2-chlorophenoxy)hexanoate (JRW-0725)

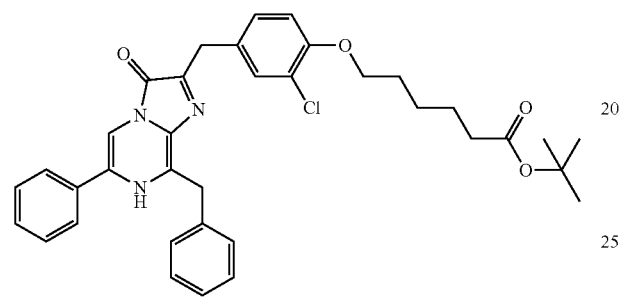

Following general procedure E, tert-butyl (Z)-6-(4-((8-benzyl-3-oxo-6-phenylimidazo[1,2-a]pyrazin-2(3H)-ylidene)methyl)-2-chlorophenoxy)hexanoate (180 mg, 0.29 mmol) was reacted with sodium borohydride (55 mg, 1.5 mmol) to afford the desired product (83 mg, 42% over two steps) as an orange foam. $^1$H NMR (300 MHz, CD$_3$OD) δ 7.82-7.58 (m, 3H), 7.57-7.14 (m, 9H), 6.96 (d, J=8.5, 1H), 4.42 (s, 2H), 4.10 (s, 2H), 4.00 (t, J=6.0, 2H), 2.23 (t, J=7.2, 2H), 1.85-1.40 (m, 15H); ESI MS m/z 610 [M−H]−; HPLC 98.8% (AUC), T$_R$ 7.63 min; UV (MeOH) λ 434 nm, ε 9028.

Example 13

6-(4-((8-benzyl-3-oxo-6-phenyl-3,7-dihydroimidazo[1,2-a]pyrazin-2-yl)methyl)-2-chlorophenoxy)hexanoic acid (JRW-0726)

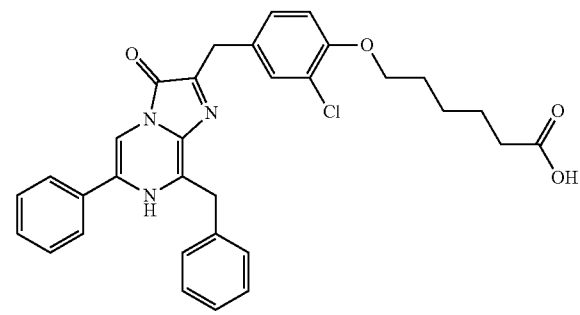 [SMILES: O=C(O)CCCCCOc1ccc(Cc2nc3c(Cc4ccccc4)[nH]c(-c4ccccc4)cn-3c2=O)cc1Cl]

Following general procedure F, tert-butyl 6-(4-((8-benzyl-3-oxo-6-phenyl-3,7-dihydroimidazo[1,2-a]pyrazin-2-yl)methyl)-2-chlorophenoxy)hexanoate (75 mg, 0.12 mmol) was reacted with trifluoroacetic acid (1 mL) to afford the desired product (63 mg, 92%) as an orange solid. $^1$H NMR (300 MHz, CD$_3$OD) δ 8.60 (s, 1H), 8.00-7.90 (m, 2H), 7.56-7.41 (m, 5H), 7.40-7.16 (m, 5H), 7.05-6.97 (m, 1H), 4.60 (s, 2H), 4.25 (s, 2H), 4.02 (t, J=6.2, 2H), 2.34 (t, J=7.3, 2H), 1.86-1.45 (m, 6H); ESI MS m/z 557 [M+H]+; HPLC 99.5% (AUC), T$_R$ 5.67 min; UV (MeOH) λ 426 nm, ε 5509.

Example 14 sodium 6-(4-((8-benzyl-3-oxo-6-phenyl-3,7-dihydroimidazo[1,2-a]pyrazin-2-yl)methyl)-2-chlorophenoxy)hexane-1-sulfonate (JRW-0728)

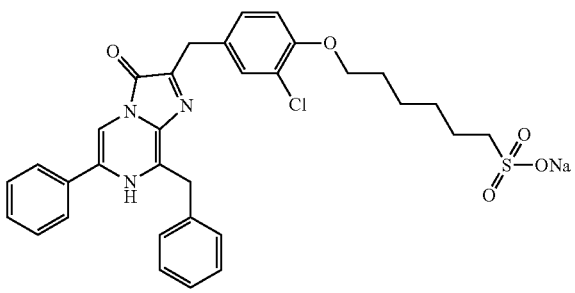

Step 1. sodium 6-(2-chloro-4-formylphenoxy)hexane-1-sulfonate (JRW-0723)

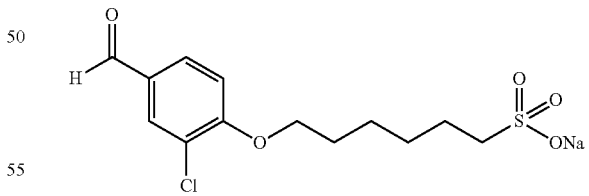

Following general procedure G, 4-((6-bromohexyl)oxy)-3-chlorobenzaldehyde (280 mg, 0.88 mmol) was reacted with sodium sulfite (552 mg, 4.4 mmol) to afford crude product (310 mg) as a white solid. $^1$H NMR (300 MHz, CD$_3$OD) δ 9.81 (s, 1H), 7.92-7.80 (m, 2H), 7.23 (d, J=8.5, 1H), 4.18 (t, J=6.3, 2H), 2.85-2.76 (m, 2H), 1.97-1.73 (m, 4H), 1.63-1.48 (m, 4H).

Step 2. sodium (Z)-6-(4-((8-benzyl-3-oxo-6-phenylimidazo[1,2-a]pyrazin-2(3H)-ylidene)methyl)-2-chlorophenoxy)hexane-1-sulfonate (JRW-0727)

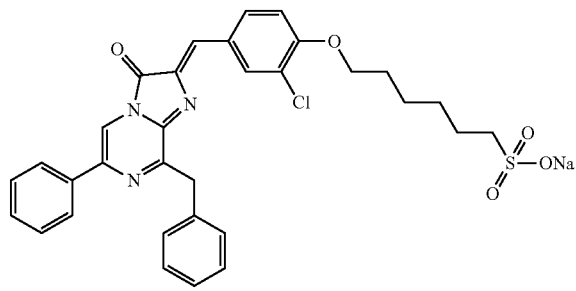

Following general procedure H, sodium 6-(2-chloro-4-formylphenoxy)hexane-1-sulfonate (292 mg, 0.85 mmol) was reacted with methyl 2-((3-benzyl-5-phenylpyrazin-2-yl)amino)-2-(diethoxyphosphoryl)acetate (200 mg, 0.42 mmol) to afford crude product (370 mg) as a red black solid.

Step 3. sodium 6-(4-((8-benzyl-3-oxo-6-phenyl-3,7-dihydroimidazo[1,2-a]pyrazin-2-yl)methyl)-2-chlorophenoxy)hexane-1-sulfonate (JRW-0728)

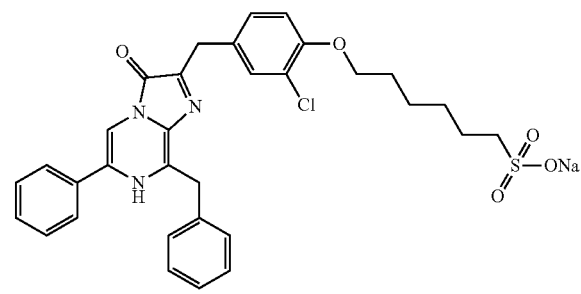

Following general procedure I, sodium (Z)-6-(4-((8-benzyl-3-oxo-6-phenylimidazo[1,2-a]pyrazin-2(3H)-ylidene)methyl)-2-chlorophenoxy)hexane-1-sulfonate (0.42 mmol) was reacted with sodium borohydride (80 mg, 2.1 mmol) to afford the desired product (198 mg, 73% over two steps) as an orange solid. Note: isolated material was not pure, impurities present. $^1$H NMR (300 MHz, CD$_3$OD) δ 7.80-7.55 (m, 3H), 7.52-7.16 (m, 10H), 7.03-6.93 (m, 1H), 4.42 (s, 2H), 4.10 (s, 2H), 4.07-3.95 (m, 2H), 2.84-2.76 (m, 2H), 1.93-1.72 (m, 4H), 1.65-1.44 (m, 4H); ESI MS m/z 605 [M–H]–; HPLC 97.9% (AUC), T$_R$ 4.64 min; UV (MeOH) λ 433 nm, ε 4777.

Example 15

(S)-3-acetamido-4-(((S)-1-(((S)-1-((6-(3-((8-benzyl-3-oxo-6-phenyl-3,7-dihydroimidazo[1,2-a]pyrazin-2-yl)methyl)phenoxy)hexyl)amino)-3-carboxy-1-oxopropan-2-yl)amino)-3-carboxy-1-oxopropan-2-yl)amino)-4-oxobutanoic acid (JRW-0741)

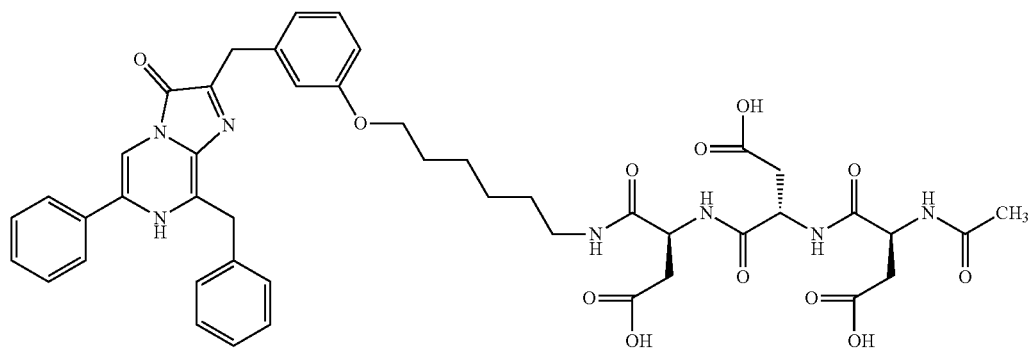 [SMILES: CC(=O)N[C@@H](CC(=O)O)C(=O)N[C@@H](CC(=O)O)C(=O)N[C@@H](CC(=O)O)C(=O)NCCCCCCOc1cccc(Cc2nc3c(Cc4ccccc4)[nH]c(-c4ccccc4)cn-3c2=O)c1]

Step 1. tert-butyl (6-(3-formylphenoxy)hexyl)carbamate (JRW-0730)

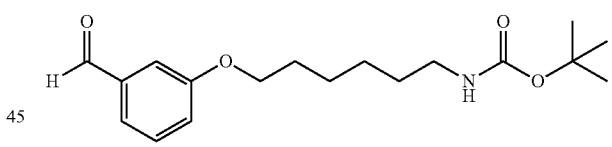

Following general procedure A, 3-hydroxybenzaldehyde (0.5 g, 4.1 mmol) was reacted with tert-butyl (6-bromohexyl)carbamate (1.15 g, 4.1 mmol) to afford the desired crude product (1.02 g) as a colorless oil.

Step 2. tert-butyl (Z)-(6-(3-((8-benzyl-3-oxo-6-phenylimidazo[1,2-a]pyrazin-2(3H)-ylidene)methyl)phenoxy)hexyl)carbamate (JRW-0733)

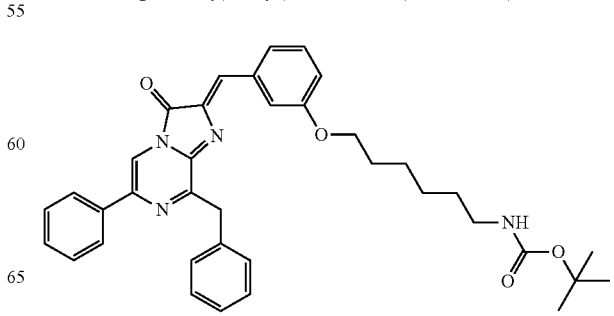

Following general procedure D, tert-butyl (6-(3-formylphenoxy)hexyl)carbamate (164 mg, 0.51 mmol) was reacted with methyl 2-((3-benzyl-5-phenylpyrazin-2-yl)amino)-2-(diethoxyphosphoryl)acetate (200 mg, 0.43 mmol) to afford the desired crude product (109 mg) as a red black solid. ESI MS m/z 605 [M+H]+.

Step 3. tert-butyl (6-(3-((8-benzyl-3-oxo-6-phenyl-3,7-dihydroimidazo[1,2-a]pyrazin-2-yl)methyl)phenoxy)hexyl)carbamate (JRW-0734)

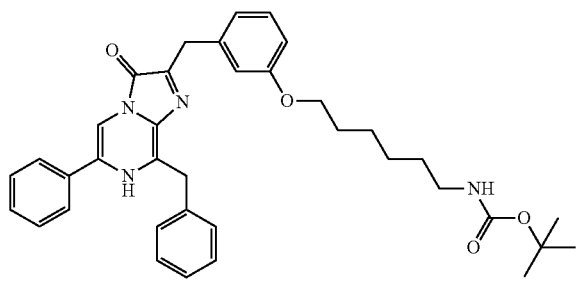 [SMILES: CC(C)(C)OC(=O)NCCCCCCOc1cccc(Cc2nc3c(Cc4ccccc4)[nH]c(-c4ccccc4)cn-3c2=O)c1]

Following general procedure E, tert-butyl (Z)-(6-(3-((8-benzyl-3-oxo-6-phenylimidazo[1,2-a]pyrazin-2(3H)-ylidene)methyl)phenoxy)hexyl)carbamate (109 mg, 0.18 mmol) was reacted with sodium borohydride (34 mg, 0.90 mmol) to afford the desired product (75 mg, 29% over two steps) as an orange foam. ESI MS m/z 607 [M+H]+.

Step 4. 2-(3-((6-aminohexyl)oxy)benzyl)-8-benzyl-6-phenylimidazo[1,2-a]pyrazin-3(7H)-one (JRW-0737 or TAK-0039)

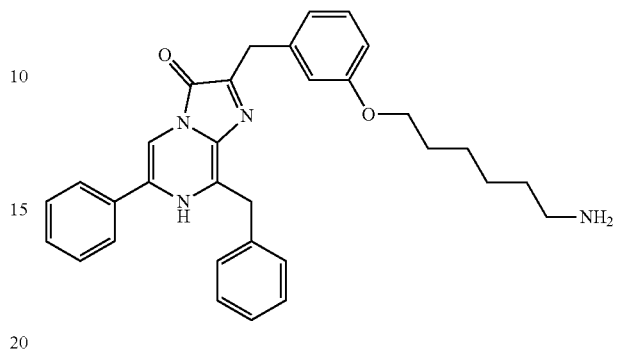

Following general procedure F, tert-butyl (6-(3-((8-benzyl-3-oxo-6-phenyl-3,7-dihydroimidazo[1,2-a]pyrazin-2-yl)methyl)phenoxy)hexyl)carbamate (75 mg, 0.12 mmol) was reacted with trifluoroacetic acid (1 mL) to afford the desired product (62 mg, quant) as an orange oil. ESI MS m/z 507 [M+H]+.

Step 5. tert-butyl (S)-3-acetamido-4-(((S)-1-(((S)-1-((6-(3-((8-benzyl-3-oxo-6-phenyl-3,7-dihydroimidazo[1,2-a]pyrazin-2-yl)methyl)phenoxy)hexyl)amino)-4-(tert-butoxy)-1,4-dioxobutan-2-yl)amino)-4-(tert-butoxy)-1,4-dioxobutan-2-yl)amino)-4-oxobutanoate (JRW-0739)

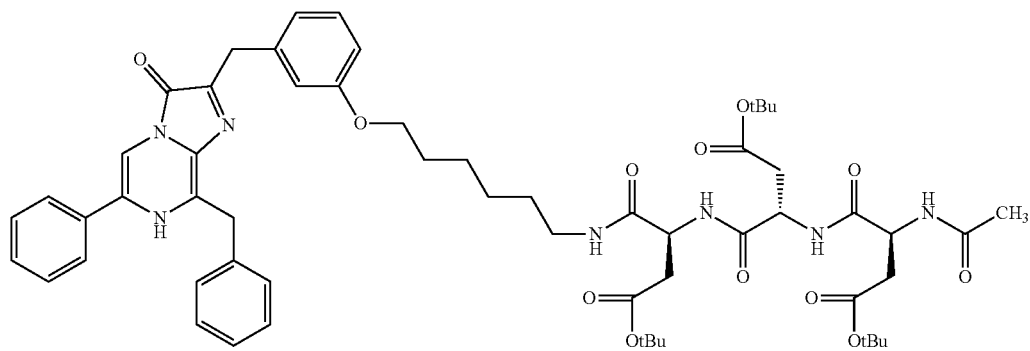 [SMILES: CC(=O)N[C@@H](CC(=O)OC(C)(C)C)C(=O)N[C@@H](CC(=O)OC(C)(C)C)C(=O)N[C@@H](CC(=O)OC(C)(C)C)C(=O)NCCCCCCOc1cccc(Cc2nc3c(Cc4ccccc4)[nH]c(-c4ccccc4)cn-3c2=O)c1]

To a solution of 2-(3-((6-aminohexyl)oxy)benzyl)-8-benzyl-6-phenylimidazo[1,2-a]pyrazin-3(7H)-one (62 mg, 0.12 mmol) in DCM (10 mL) and methanol (0.5 mL) was added 4-(tert-butyl) 1-(2,5-dioxopyrrolidin-1-yl) ((S)-2-((S)-2-acetamido-4-(tert-butoxy)-4-oxobutanamido)-4-(tert-butoxy)-4-oxobutanoyl)-L-aspartate (165 mg, 0.25 mmol) and 2,6-lutidine (75 mg, 0.62 mmol). The mixture stirred at rt for 1.5 h, diluted with dichloromethane and water. The aqueous layer was extracted with dichloromethane. The organic layers were combined, dried with sodium sulfate, filtered, concentrated, and purified with silica gel chromatography to afford crude product (89 mg) as an orange foam. ESI MS m/z 1062 [M+H]+.

Step 6. (S)-3-acetamido-4-(((S)-1-(((S)-1-((6-(3-((8-benzyl-3-oxo-6-phenyl-3,7-dihydroimidazo[1,2-a]pyrazin-2-yl)methyl)phenoxy)hexyl)amino)-3-carboxy-1-oxopropan-2-yl)amino)-3-carboxy-1-oxopropan-2-yl)amino)-4-oxobutanoic acid (JRW-0741)

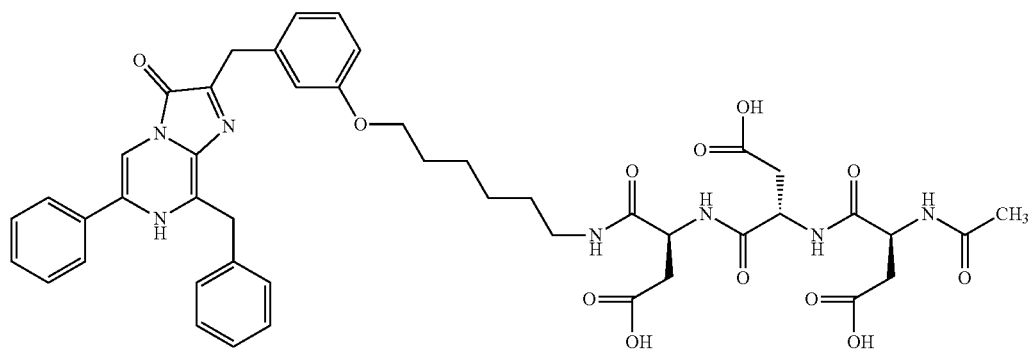 [SMILES: CC(=O)N[C@@H](CC(=O)O)C(=O)N[C@@H](CC(=O)O)C(=O)N[C@@H](CC(=O)O)C(=O)NCCCCCCOc1cccc(Cc2nc3c(Cc4ccccc4)[nH]c(-c4ccccc4)cn-3c2=O)c1]

Following general procedure F, tert-butyl (S)-3-acetamido-4-(((S)-1-(((S)-1-((6-(3-((8-benzyl-3-oxo-6-phenyl-3,7-dihydroimidazo[1,2-a]pyrazin-2-yl)methyl)phenoxy)hexyl)amino)-4-(tert-butoxy)-1,4-dioxobutan-2-yl)amino)-4-(tert-butoxy)-1,4-dioxobutan-2-yl)amino)-4-oxobutanoate (89 mg, 0.084 mmol) was reacted with TFA (1 mL) to afford the desired product (78 mg, quant) as an orange red solid. $^1$H NMR (300 MHz, CD$_3$OD) δ 8.63 (s, 1H), 8.02-7.93 (s, 2H), 7.58-7.40 (m, 5H), 7.39-7.13 (m, 4H), 6.93-6.77 (m, 3H), 4.73-4.48 (s, 5H), 4.30 (s, 2H), 4.01-3.88 (m, 2H), 3.25-3.08 (m, 2H), 3.00-2.65 (m, 7H), 1.98 (s, 3H), 1.85-1.68 (m, 2H), 1.60-1.25 (s, 6H); ESI MS m/z 894 [M+H]+; HPLC 95.3% (AUC), T$_R$ 4.53 min; UV (MeOH) λ 256 nm, ε 14007.

Example 16 sodium 8-(4-((8-benzyl-3-oxo-6-phenyl-3,7-dihydroimidazo[1,2-a]pyrazin-2-yl)methyl)-2-chlorophenoxy)octane-1-sulfonate (JRW-0761)

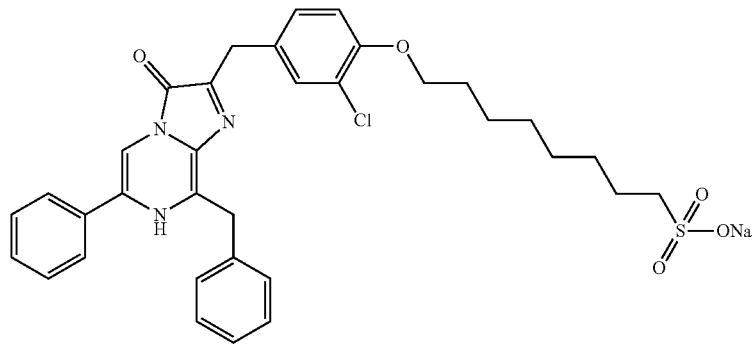

Step 1. 4-((8-bromooctyl)oxy)-3-chlorobenzaldehyde (JRW-0745)

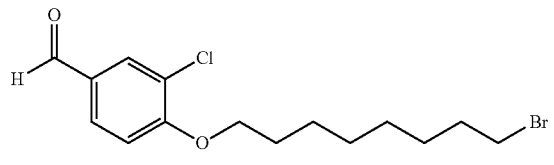 [SMILES: O=Cc1ccc(OCCCCCCCCBr)c(Cl)c1]

Following general procedure A, 3-chloro-4-hydroxybenzaldehyde (620 mg, 3.9 mmol) was reacted with 1,8-dibromooctane (1.62 g, 5.9 mmol) to afford the desired product (715 mg, 52%) as a white solid. $^1$H NMR (300 MHz, CDCl$_3$) δ 9.84 (s, 1H), 7.90 (d, J=2.0, 1H), 7.74 (dd, J=2.0, 8.5, 1H), 7.01 (d, J=8.4, 1H), 4.11 (t, J=6.4, 2H), 3.41 (t, J=6.8, 2H), 1.95-1.78 (m, 4H), 1.60-1.28 (m, 8H); ESI MS m/z 347 [M+H]+.

Step 2. sodium 8-(2-chloro-4-formylphenoxy)octane-1-sulfonate (JRW-0747)

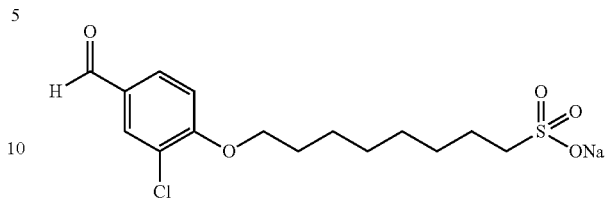

Following general procedure G, 4-((8-bromooctyl)oxy)-3-chlorobenzaldehyde (715 mg, 2.1 mmol) was reacted with sodium sulfite (1.3 g, 10.3 mmol) to afford crude product (810 mg) as a white solid. $^1$H NMR (300 MHz, CD$_3$OD) δ 9.81 (s, 1H), 7.94-7.80 (m, 2H), 7.23 (d, J=8.5, 1H), 4.17 (t, J=6.3, 2H), 2.87-2.70 (m, 2H), 1.96-1.74 (m, 4H), 1.62-1.35 (m, 8H).

Step 3. sodium (Z)-8-(4-((8-benzyl-3-oxo-6-phenylimidazo[1,2-a]pyrazin-2(3H)-ylidene)methyl)-2-chlorophenoxy)octane-1-sulfonate (JRW-0760)

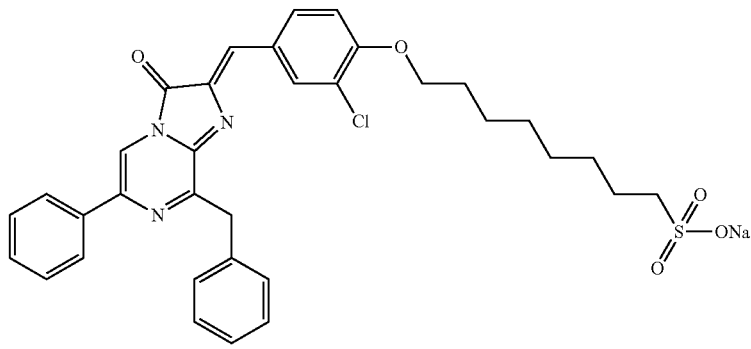

Following general procedure H, sodium 8-(2-chloro-4-formylphenoxy)octane-1-sulfonate (94 mg, 0.25 mmol) was reacted with methyl 2-((3-benzyl-5-phenylpyrazin-2-yl)amino)-2-(diethoxyphosphoryl)acetate (120 mg, 0.25 mmol) to afford crude product (150 mg) as a red black solid.

Step 4. sodium 8-(4-((8-benzyl-3-oxo-6-phenyl-3,7-dihydroimidazo[1,2-a]pyrazin-2-yl)methyl)-2-chlorophenoxy)octane-1-sulfonate (JRW-0761)

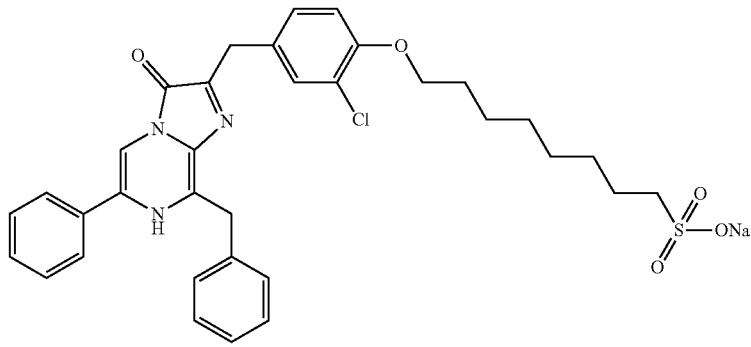

Following general procedure I, sodium (Z)-8-(4-((8-benzyl-3-oxo-6-phenylimidazo[1,2-a]pyrazin-2(3H)-ylidene)methyl)-2-chlorophenoxy)octane-1-sulfonate (150 mg, 0.23 mmol) was reacted with sodium borohydride (43 mg, 1.15 mmol) to afford the desired product (30 mg, 18% over two steps) as a yellow solid. $^1$H NMR (300 MHz, CD$_3$OD) δ 8.10 (s, 1H), 7.92-7.80 (m, 2H), 7.52-7.09 (m, 10H), 6.95-6.87 (m, 1H), 4.40 (s, 2H), 4.13-3.92 (m, 4H), 2.86-2.75 (m, 2H), 1.92-1.70 (m, 4H), 1.61-1.33 (m, 8H); ESI MS m/z 634 [M+H−Na]+; HPLC 87.9% (AUC), T$_R$ 3.69 min; UV (MeOH) λ 402 nm, ε 6345.

Example 17 sodium 10-(4-((8-benzyl-3-oxo-6-phenyl-3,7-dihydroimidazo[1,2-a]pyrazin-2-yl)methyl)-2-chlorophenoxy)decane-1-sulfonate (JRW-0765)

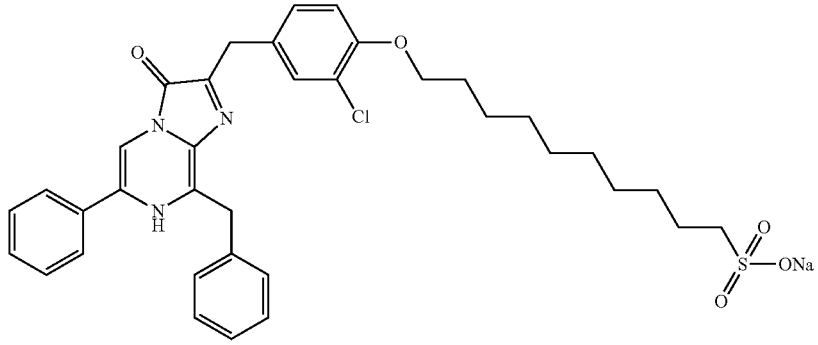

JRW-0765

Step 1. 4-((10-bromodecyl)oxy)-3-chlorobenzaldehyde (JRW-0746)

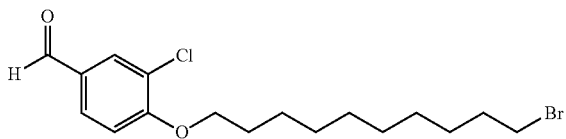 [SMILES: O=Cc1ccc(OCCCCCCCCCCBr)c(Cl)c1]

Following general procedure A, 3-chloro-4-hydroxybenzaldehyde (640 mg, 4.1 mmol) was reacted with 1,10-dibromodecane (1.84 g, 6.1 mmol) to afford the desired product (780 mg, 50%) as a white solid. $^1$H NMR (300 MHz, CDCl$_3$) δ 9.84 (s, 1H), 7.90 (d, J=2.0, 1H), 7.75 (dd, J=2.0, 8.5, 1H), 7.01 (d, J=8.4, 1H), 4.12 (t, J=6.5, 2H), 3.41 (t, J=6.8, 2H), 1.93-1.76 (m, 4H), 1.52-1.23 (m, 12H); ESI MS m/z 347 [M+H]+.

Step 2. sodium 10-(2-chloro-4-formylphenoxy)decane-1-sulfonate (JRW-0748)

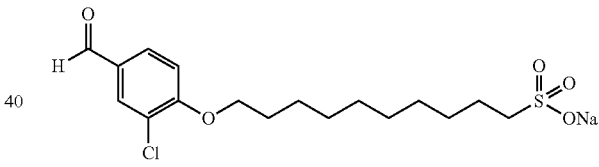

Following general procedure G, 4-((10-bromodecyl)oxy)-3-chlorobenzaldehyde (780 mg, 2.1 mmol) was reacted with sodium sulfite (1.3 g, 10.3 mmol) to afford crude product (910 mg) as a white solid. $^1$H NMR (300 MHz, CD$_3$OD) δ 9.81 (s, 1H), 7.90 (d, J=2.0, 1H), 7.85-7.80 (m, 1H), 7.23 (d, J=8.5, 1H), 4.17 (t, J=6.3, 2H), 2.85-2.70 (m, 2H), 1.93-1.71 (m, 4H), 1.60-1.30 (m, 12H).

Step 3. sodium (Z)-10-(4-((8-benzyl-3-oxo-6-phenylimidazo[1,2-a]pyrazin-2(3H)-ylidene)methyl)-2-chlorophenoxy)decane-1-sulfonate (JRW-0763)

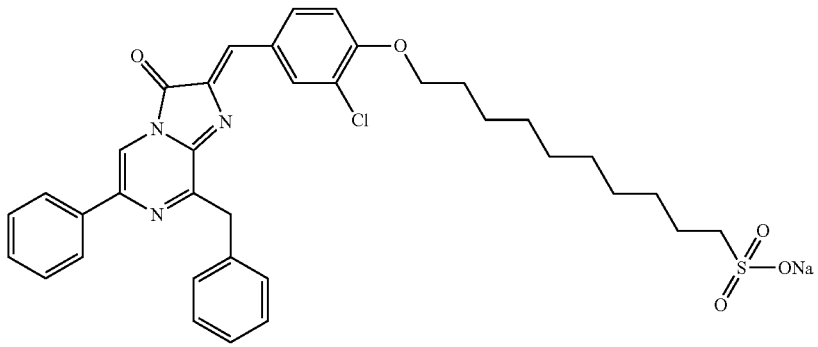

Following general procedure H, 4-((10-bromodecyl)oxy)-3-chlorobenzaldehyde (102 mg, 0.25 mmol) was reacted with methyl 2-((3-benzyl-5-phenylpyrazin-2-yl)amino)-2-(diethoxyphosphoryl)acetate (120 mg, 0.25 mmol) to afford crude product (120 mg) as a red black solid.

Step 4. sodium 10-(4-((8-benzyl-3-oxo-6-phenyl-3,7-dihydroimidazo[1,2-a]pyrazin-2-yl)methyl)-2-chlorophenoxy)decane-1-sulfonate (JRW-0765)

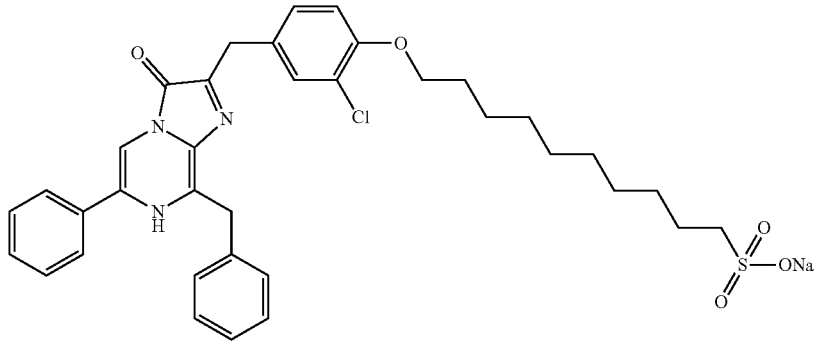

Following general procedure I, sodium (Z)-10-(4-((8-benzyl-3-oxo-6-phenylimidazo[1,2-a]pyrazin-2(3H)-ylidene)methyl)-2-chlorophenoxy)decane-1-sulfonate (120 mg, 0.18 mmol) was reacted with sodium borohydride (33 mg, 0.88 mmol) to afford the desired product (50 mg, 29% over two steps) as an orange solid. $^1$H NMR (300 MHz, CD$_3$OD) δ 7.81-7.58 (m, 3H), 7.56-7.18 (m, 10H), 7.00-6.91 (m, 1H), 4.41 (s, 2H), 4.15-3.90 (m, 4H), 2.83-2.73 (m, 2H), 1.90-1.68 (m, 4H), 1.58-1.25 (m, 12H); ESI MS m/z 662 [M+H−Na]+; HPLC 94.8% (AUC), T$_R$ 4.41 min; UV (MeOH) λ 430 nm, ε 7156.

Example 18 sodium 6-(5-((8-benzyl-3-oxo-6-phenyl-3,7-dihydroimidazo[1,2-a]pyrazin-2-yl)methyl)-2-chlorophenoxy)hexane-1-sulfonate (JRW-0766)

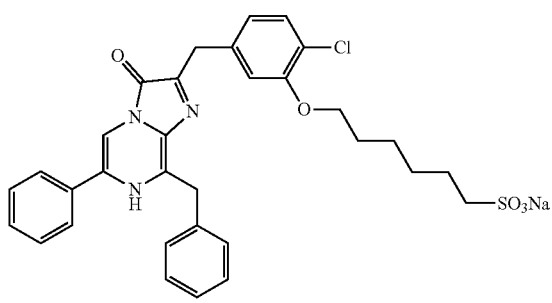

Step 1. 3-((6-bromohexyl)oxy)-4-chlorobenzaldehyde (JRW-0752)

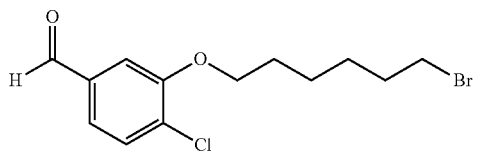 [SMILES: O=Cc1ccc(Cl)c(OCCCCCCBr)c1]

Following general procedure A, 4-chloro-3-hydroxybenzaldehyde (1.0 g, 6.4 mmol) was reacted with 1,6-dibromohexane (2.34 g, 9.6 mmol) to afford the desired product (1.05 g, 51%) as a colorless oil. $^1$H NMR (300 MHz, CDCl$_3$) δ 9.93 (s, 1H), 7.54 (d, J=7.9, 1H), 7.45-7.35 (m, 2H), 4.11 (t, J=6.3, 2H), 3.43 (t, J=6.8, 2H), 2.01-1.80 (m, 4H), 1.65-1.47 (m, 4H); ESI MS m/z 319 [M+H]+.

Step 2. sodium 6-(2-chloro-5-formylphenoxy)hexane-1-sulfonate (JRW-0758)

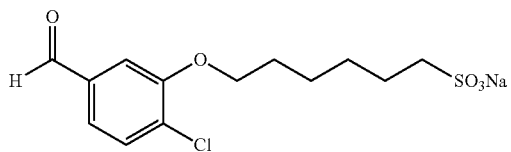

Following general procedure G, 3-((6-bromohexyl)oxy)-4-chlorobenzaldehyde (1.0 g, 3.1 mmol) was reacted with sodium sulfite (2.0 g, 15.6 mmol) to afford crude product (210 mg) as a white solid. $^1$H NMR (300 MHz, CD$_3$OD) δ 7.34 (d, J=8.1, 1H), 7.09 (d, J=1.8, 1H), 6.97 (dd, J=1.8, 8.1, 1H), 5.35 (s, 1H), 4.05 (t, J=6.3, 2H), 2.91-2.77 (m, 2H), 1.93-1.72 (m, 4H), 1.65-1.42 (m, 4H).

Step 3. sodium (Z)-6-(5-((8-benzyl-3-oxo-6-phenylimidazo[1,2-a]pyrazin-2(3H)-ylidene)methyl)-2-chlorophenoxy)hexane-1-sulfonate (JRW-0764)

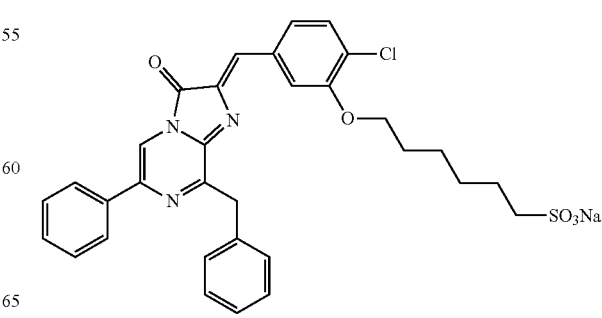

Following general procedure H, sodium 6-(2-chloro-5-formylphenoxy)hexane-1-sulfonate (87 mg, 0.25 mmol) was reacted with methyl 2-((3-benzyl-5-phenylpyrazin-2-yl)amino)-2-(diethoxyphosphoryl)acetate (120 mg, 0.25 mmol) to afford crude product (90 mg) as a red black solid.

Step 4. sodium 6-(5-((8-benzyl-3-oxo-6-phenyl-3,7-dihydroimidazo[1,2-a]pyrazin-2-yl)methyl)-2-chlorophenoxy)hexane-1-sulfonate (JRW-0766)

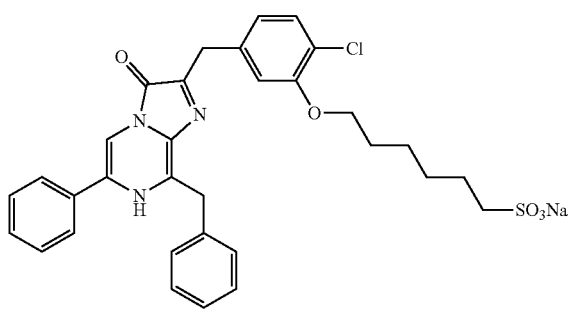

Following general procedure I, sodium (Z)-6-(5-((8-benzyl-3-oxo-6-phenylimidazo[1,2-a]pyrazin-2(3H)-ylidene)methyl)-2-chlorophenoxy)hexane-1-sulfonate (90 mg, 0.14 mmol) was reacted with sodium borohydride (27 mg, 0.72 mmol) to afford the desired product (30 mg, 19% over two steps) as an orange red solid. $^1$H NMR (300 MHz, CD$_3$OD) δ 7.80-7.60 (m, 3H), 7.58-7.15 (m, 9H), 7.06 (s, 1H), 6.96-6.80 (m, 1H), 4.42 (s, 2H), 4.14 (s, 2H), 4.02-3.96 (m, 2H), 2.90-2.68 (m, 2H), 1.90-1.70 (m, 4H), 1.60-1.40 (m, 4H); ESI MS m/z 606 [M+H−Na]+; HPLC 94.9% (AUC), T$_R$ 3.31 min; UV (MeOH) λ 432 nm, ε 7869.

Example 19 sodium 6-(4-((8-benzyl-3-oxo-6-phenyl-3,7-dihydroimidazo[1,2-a]pyrazin-2-yl)methyl)-2-fluorophenoxy)hexane-1-sulfonate (JRW-0769)

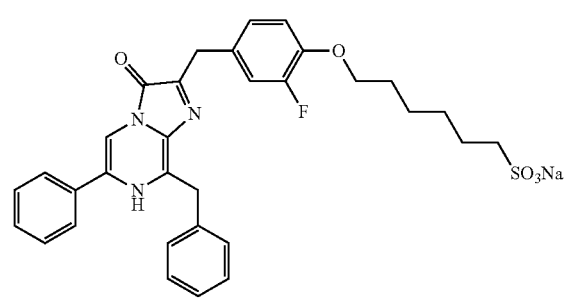

Step 1. 4-((6-bromohexyl)oxy)-3-fluorobenzaldehyde (JRW-0757)

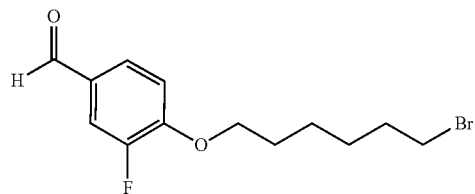 [SMILES: O=Cc1ccc(OCCCCCCBr)c(F)c1]

Following general procedure A, 3-fluoro-4-hydroxybenzaldehyde (1.0 g, 7.3 mmol) was reacted with 1,6-dibromohexane (2.66 g, 10.9 mmol) to afford the desired product (1.42 g, 64%) as a colorless oil. $^1$H NMR (300 MHz, CDCl$_3$) δ 9.85 (s, 1H), 7.67-7.56 (m, 2H), 7.10-7.02 (m, 1H), 4.12 (t, J=6.4, 2H), 3.43 (t, J=6.7, 2H), 1.97-1.80 (m, 4H), 1.73-1.41 (m, 4H); ESI MS m/z 303 [M+H]+.

Step 2. sodium 6-(2-fluoro-4-formylphenoxy)hexane-1-sulfonate (JRW-0762)

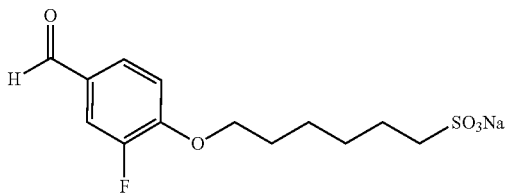

Following general procedure G, 4-((6-bromohexyl)oxy)-3-fluorobenzaldehyde (1.38 g, 4.55 mmol) was reacted with sodium sulfite (2.9 g, 22.7 mmol) to afford crude product (1.5 g) as a white solid. $^1$H NMR (300 MHz, DMSO-d$_6$) δ 9.84 (s, 1H), 7.80-7.70 (m, 1H), 7.66 (dd, J=1.9, 11.4, 1H), 7.37 (t, J=8.3, 1H), 4.15 (t, J=6.6, 2H), 2.42-2.34 (m, 2H), 1.80-1.65 (m, 2H), 1.64-1.49 (m, 2H), 1.47-1.29 (m, 4H).

Step 3. sodium (Z)-6-(4-((8-benzyl-3-oxo-6-phenylimidazo[1,2-a]pyrazin-2(3H)-ylidene)methyl)-2-fluorophenoxy)hexane-1-sulfonate (JRW-0767)

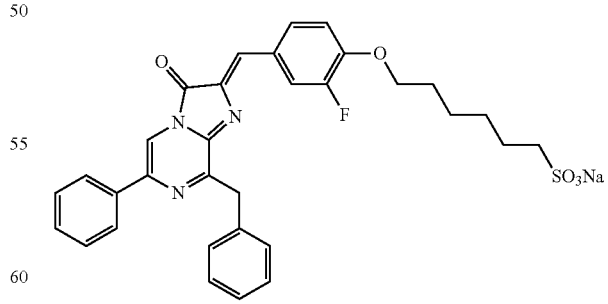

Following general procedure H, sodium 6-(2-fluoro-4-formylphenoxy)hexane-1-sulfonate (83 mg, 0.25 mmol) was reacted with methyl 2-((3-benzyl-5-phenylpyrazin-2-yl)amino)-2-(diethoxyphosphoryl)acetate (120 mg, 0.25 mmol) to afford crude product (155 mg) as a red black solid.

Step 4. sodium 6-(4-((8-benzyl-3-oxo-6-phenyl-3,7-dihydroimidazo[1,2-a]pyrazin-2-yl)methyl)-2-fluorophenoxy)hexane-1-sulfonate (JRW-0769)

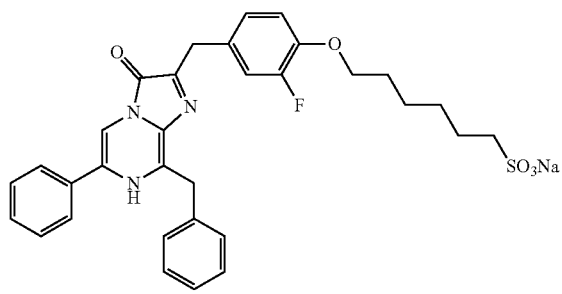

Following general procedure I, sodium (Z)-6-(5-((8-benzyl-3-oxo-6-phenylimidazo[1,2-a]pyrazin-2(3H)-ylidene)methyl)-2-chlorophenoxy)hexane-1-sulfonate (0.25 mmol) was reacted with sodium borohydride (29 mg, 0.76 mmol) to afford the desired product (72 mg, 47% over two steps) as an orange solid. $^1$H NMR (300 MHz, CD$_3$OD) δ 7.80-7.58 (m, 3H), 7.50-7.37 (m, 5H), 7.35-7.16 (m, 3H), 7.13-6.93 (m, 3H), 4.41 (s, 2H), 4.10 (s, 2H), 4.00 (t, J=6.5, 2H), 2.86-2.72 (m, 2H), 1.91-1.71 (m, 4H), 1.60-1.45 (m, 4H); ESI MS m/z 590 [M+H−Na]+; HPLC 96.1% (AUC), T$_R$ 2.94 min; UV (MeOH) λ 432 nm, ε 7831.

Example 20 sodium 6-(4-((8-benzyl-3-oxo-6-phenyl-3,7-dihydroimidazo[1,2-a]pyrazin-2-yl)methyl)-2,6-difluorophenoxy)hexane-1-sulfonate (JRW-0771)

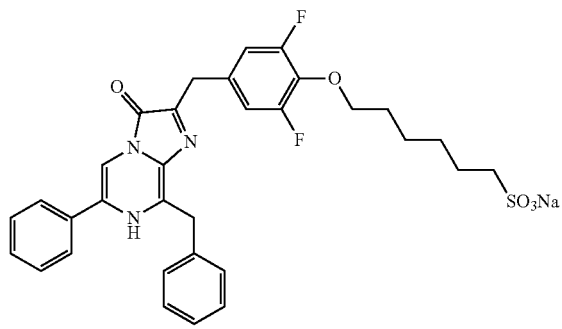

Step 1. 4-((6-bromohexyl)oxy)-3,5-difluorobenzaldehyde (JRW-0753)

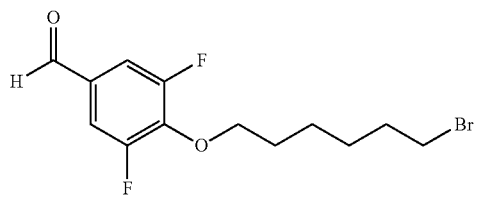 [SMILES: O=Cc1cc(F)c(OCCCCCCBr)c(F)c1]

Following general procedure A, 3,5-difluoro-4-hydroxybenzaldehyde (1.0 g, 6.3 mmol) was reacted with 1,6-dibromohexane (2.31 g, 9.5 mmol) to afford the desired product (0.54 g, 27%) as a colorless oil. $^1$H NMR (300 MHz, CDCl$_3$) δ 9.83 (t, J=1.8, 1H), 7.50-7.38 (m, 2H), 4.29 (t, J=6.4, 2H), 3.47-3.36 (m, 2H), 1.95-1.75 (m, 4H), 1.60-1.39 (m, 4H).

Step 2. sodium 6-(2,6-difluoro-4-formylphenoxy)hexane-1-sulfonate (JRW-0759)

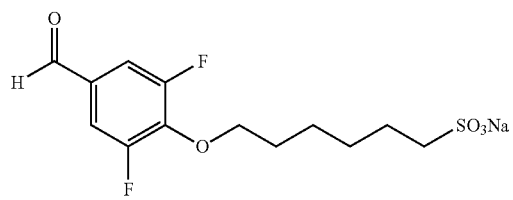

Following general procedure G, 4-((6-bromohexyl)oxy)-3,5-difluorobenzaldehyde (500 mg, 1.6 mmol) was reacted with sodium sulfite (980 mg, 7.8 mmol) to afford crude product (530 mg) as a light pink solid. $^1$H NMR (300 MHz, CD$_3$OD) δ 7.09-6.97 (m, 2H), 5.33 (s, 1H), 4.11 (t, J=6.3, 2H), 2.90-2.77 (m, 2H), 1.89-1.66 (m, 4H), 1.64-1.31 (m, 4H).

Step 3. sodium (Z)-6-(4-((8-benzyl-3-oxo-6-phenylimidazo[1,2-a]pyrazin-2(3H)-ylidene)methyl)-2,6-difluorophenoxy)hexane-1-sulfonate (JRW-0770)

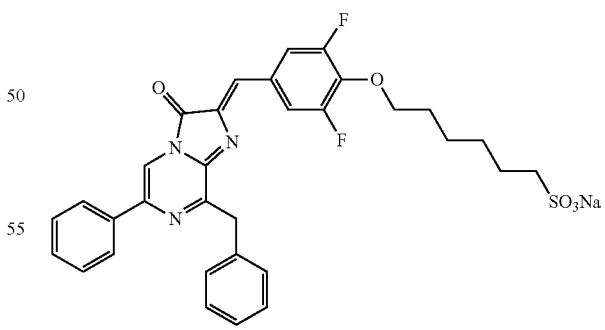

Following general procedure H, sodium 6-(2,6-difluoro-4-formylphenoxy)hexane-1-sulfonate (80 mg, 0.23 mmol) was reacted with methyl 2-((3-benzyl-5-phenylpyrazin-2-yl)amino)-2-(diethoxyphosphoryl)acetate (110 mg, 0.23 mmol) to afford crude product as a red black solid.

Step 4. sodium 6-(4-((8-benzyl-3-oxo-6-phenyl-3,7-dihydroimidazo[1,2-a]pyrazin-2-yl)methyl)-2,6-difluorophenoxy)hexane-1-sulfonate (JRW-0771)

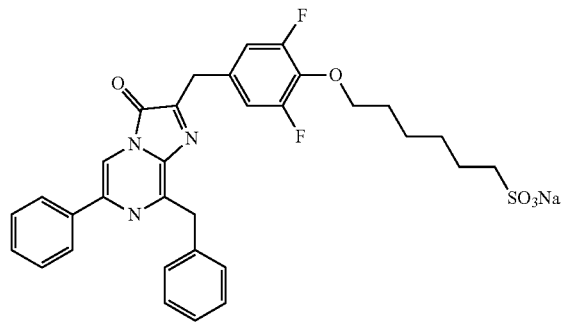

Following general procedure I, sodium (Z)-6-(4-((8-benzyl-3-oxo-6-phenylimidazo[1,2-a]pyrazin-2(3H)-ylidene)methyl)-2,6-difluorophenoxy)hexane-1-sulfonate (0.23 mmol) was reacted with sodium borohydride (26 mg, 0.69 mmol) to afford the desired product (8 mg, 5% over two steps) as an orange solid. $^1$H NMR (300 MHz, CD$_3$OD) δ 7.81-7.59 (m, 3H), 7.55-7.38 (m, 5H), 7.35-7.18 (m, 3H), 7.05-6.93 (m, 2H), 4.42 (s, 2H), 4.15-4.01 (m, 4H), 2.86-2.71 (m, 2H), 1.90-1.67 (m, 4H), 1.58-1.40 (m, 4H); ESI MS m/z 606 [M−H−Na]−; HPLC 97.3% (AUC), T$_R$ 3.12 min; UV (MeOH) λ 434 nm, ε 7456.

Example 21

2-(4-((6-aminohexyl)oxy)-3-fluorobenzyl)-8-benzyl-6-phenylimidazo[1,2-a]pyrazin-3(7H)-one (JRW-0801)

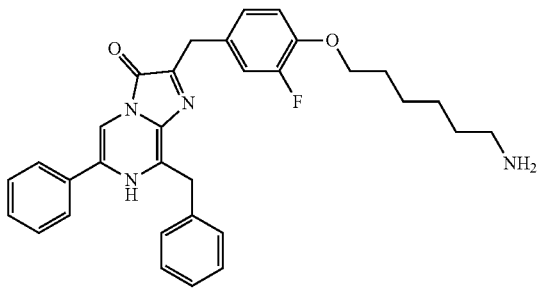 [SMILES: NCCCCCCOc1ccc(Cc2nc3c(Cc4ccccc4)[nH]c(-c4ccccc4)cn-3c2=O)cc1F]

Step 1. tert-butyl (6-(2-fluoro-4-formylphenoxy)hexyl)carbamate (JRW-0797)

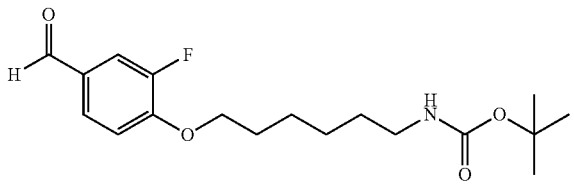 [SMILES: CC(C)(C)OC(=O)NCCCCCCOc1ccc(C=O)cc1F]

Following general procedure A, 3-fluoro-4-hydroxybenzaldehyde (200 mg, 1.4 mmol) was reacted with tert-butyl (6-bromohexyl)carbamate (400 mg, 1.4 mmol) to afford the desired product (470 mg, 97%) as a colorless oil. $^1$H NMR (300 MHz, CDCl$_3$) δ 9.85 (s, 1H), 7.70-7.55 (m, 2H), 7.10-7.00 (m, 1H), 4.50 (br s, 1H), 4.10 (t, J=6.5, 2H), 3.20-3.02 (m, 2H), 1.95-1.79 (m, 2H), 1.71-1.17 (m, 15H); ESI MS m/z 240 [M+H−Boc]+.

Step 2. tert-butyl (Z)-(6-(4-((8-benzyl-3-oxo-6-phenylimidazo[1,2-a]pyrazin-2(3H)-ylidene)methyl)-2-fluorophenoxy)hexyl)carbamate (JRW-0798)

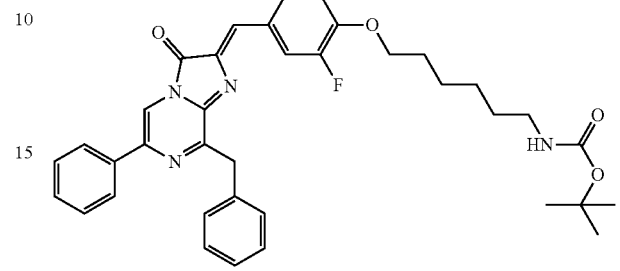

Following general procedure D, tert-butyl (6-(2-fluoro-4-formylphenoxy)hexyl)carbamate (216 mg, 0.64 mmol) was reacted with methyl 2-((3-benzyl-5-phenylpyrazin-2-yl)amino)-2-(diethoxyphosphoryl)acetate (200 mg, 0.43 mmol) to afford the desired crude product (250 mg) as a red black solid.

Step 3. tert-butyl (6-(4-((8-benzyl-3-oxo-6-phenyl-3,7-dihydroimidazo[1,2-a]pyrazin-2-yl)methyl)-2-fluorophenoxy)hexyl)carbamate (JRW-0799)

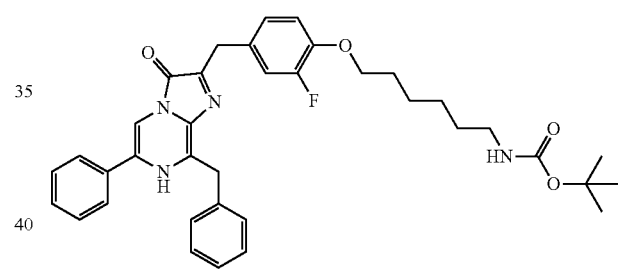

Following general procedure E, tert-butyl (Z)-(6-(4-((8-benzyl-3-oxo-6-phenylimidazo[1,2-a]pyrazin-2(3H)-ylidene)methyl)-2-fluorophenoxy)hexyl)carbamate (250 mg, 0.40 mmol) was reacted with sodium borohydride (76 mg, 2.0 mmol) to afford the desired product (108 mg, 40% over two steps).

Step 4. 2-(4-((6-aminohexyl)oxy)-3-fluorobenzyl)-8-benzyl-6-phenylimidazo[1,2-a]pyrazin-3(7H)-one (JRW-0801)

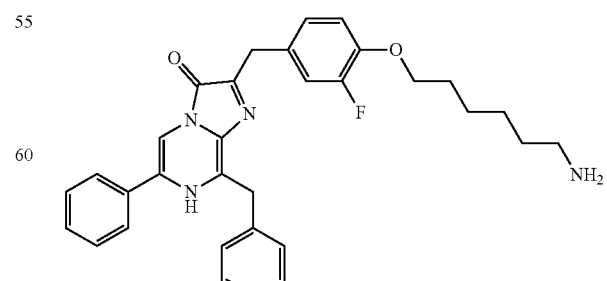

Following general procedure F, tert-butyl (6-(4-((8-benzyl-3-oxo-6-phenyl-3,7-dihydroimidazo[1,2-a]pyrazin-2-yl)methyl)-2-fluorophenoxy)hexyl)carbamate (108 mg, 0.12 mmol) was reacted with trifluoroacetic acid (1 mL) to afford the desired product (110 mg, quant) as a red orange foam. ¹H NMR (300 MHz, CD₃OD) δ 7.80-7.58 (m, 3H), 7.58-7.17 (m, 8H), 7.15-6.93 (m, 3H), 4.42 (s, 2H), 4.16-3.97 (m, 4H), 3.01-2.83 (m, 2H), 1.90-1.39 (m, 9H); ESI MS m/z 525 [M+H]+; HPLC 99.8% (AUC), T$_R$ 4.12 min; UV (MeOH) λ 433 nm, ε 6091.

Example 22

6-(4-((8-benzyl-6-(3-hydroxyphenyl)-3-oxo-3,7-dihydroimidazo[1,2-a]pyrazin-2-yl)methyl)-2-chlorophenoxy)hexane-1-sulfonic acid (JRW-0805)

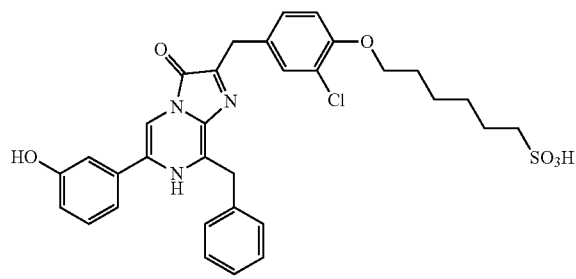 [SMILES: O=c1c(Cc2ccc(OCCCCCCS(=O)(=O)O)c(Cl)c2)nc2c(Cc3ccccc3)[nH]c(-c3cccc(O)c3)cn1-2]

Step 1. sodium (Z)-6-(4-((8-benzyl-6-(3-((tert-butyldimethylsilyl)oxy)phenyl)-3-oxoimidazo[1,2-a]pyrazin-2(3H)-ylidene)methyl)-2-chlorophenoxy)hexane-1-sulfonate (JRW-0802)

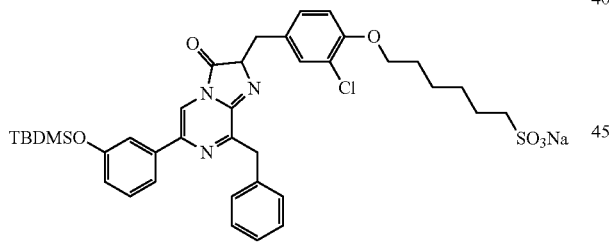

Following general procedure H, sodium 6-(2-chloro-4-formylphenoxy)hexane-1-sulfonate (100 mg, 0.29 mmol) was reacted with methyl 2-((3-benzyl-5-(3-((tert-butyldimethylsilyl)oxy)phenyl)pyrazin-2-yl)amino)-2-(diethoxyphosphoryl)acetate (175 mg, 0.29 mmol) to afford crude product (120 mg) as a red black solid.

Step 2. 6-(4-((8-benzyl-6-(3-hydroxyphenyl)-3-oxo-3,7-dihydroimidazo[1,2-a]pyrazin-2-yl)methyl)-2-chlorophenoxy)hexane-1-sulfonic acid (JRW-0805)

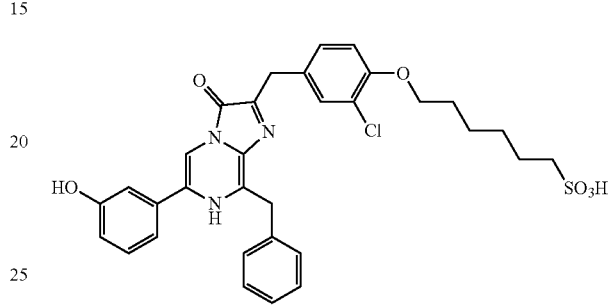

Following general procedure I, sodium (Z)-6-(4-((8-benzyl-6-(3-((tert-butyldimethylsilyl)oxy)phenyl)-3-oxoimidazo[1,2-a]pyrazin-2(3H)-ylidene)methyl)-2-chlorophenoxy)hexane-1-sulfonate (120 mg, 0.16 mmol) was reacted with sodium borohydride (30 mg, 0.79 mmol) to afford the desired product (16 mg, 13% over two steps) as an orange solid. ¹H NMR (300 MHz, CD₃OD) δ 8.01 (s, 1H), 7.55-7.40 (s, 2H), 7.40-6.99 (m, 7H), 6.98-6.85 (m, 2H), 6.73-6.52 (m, 1H), 4.36 (s, 2H), 4.11-3.90 (m, 4H), 2.92-2.75 (m, 2H), 1.95-1.72 (m, 4H), 1.65-1.45 (m, 4H); ESI MS m/z 620 [M−H]−; HPLC 89.6% (AUC), T$_R$ 4.09 min; UV (MeOH) λ 352 nm, ε 6835.

Example 23

(S)-3-acetamido-4-(((S)-1-(((S)-1-((6-(4-((8-benzyl-3-oxo-6-phenyl-3,7-dihydroimidazo[1,2-a]pyrazin-2-yl)methyl)-2-fluorophenoxy)hexyl)amino)-3-carboxy-1-oxopropan-2-yl)amino)-3-carboxy-1-oxopropan-2-yl)amino)-4-oxobutanoic acid (JRW-0806)

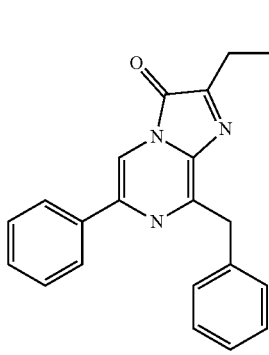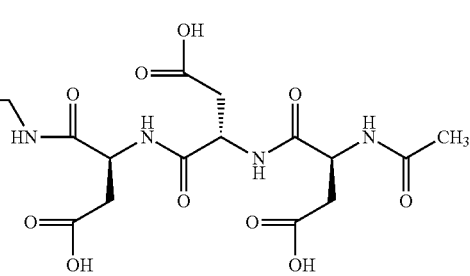

Step 1. tert-butyl (S)-3-acetamido-4-(((S)-1-(((S)-1-((6-(4-((8-benzyl-3-oxo-6-phenyl-3,7-dihydroimidazo[1,2-a]pyrazin-2-yl)methyl)-2-fluorophenoxy)hexyl)amino)-4-(tert-butoxy)-1,4-dioxobutan-2-yl)amino)-4-(tert-butoxy)-1,4-dioxobutan-2-yl)amino)-4-oxobutanoate (JRW-0803)

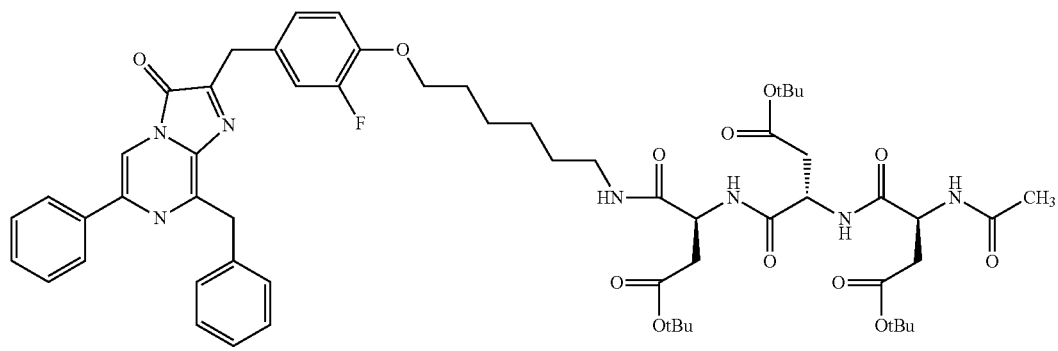 [SMILES: CC(=O)N[C@@H](CC(=O)OC(C)(C)C)C(=O)N[C@@H](CC(=O)OC(C)(C)C)C(=O)N[C@@H](CC(=O)OC(C)(C)C)C(=O)NCCCCCCOc1ccc(Cc2nc3c(Cc4ccccc4)[nH]c(-c4ccccc4)cn-3c2=O)cc1F]

To a solution of 2-(4-((6-aminohexyl)oxy)-3-fluorobenzyl)-8-benzyl-6-phenylimidazo[1,2-a]pyrazin-3(7H)-one (40 mg, 0.076 mmol) in DCM (10 mL) and methanol (0.5 mL), 4-(tert-butyl) 1-(2,5-dioxopyrrolidin-1-yl) ((S)-2-((S)-2-acetamido-4-(tert-butoxy)-4-oxobutanamido)-4-(tert-butoxy)-4-oxobutanoyl)-L-aspartate (76 mg, 0.11 mmol) and 2,6-lutidine (46 mg, 0.38 mmol) was added. The mixture stirred at RT for 3 h, and then diluted with dichloromethane and water. The aqueous layer was extracted with dichloromethane. The organic layers were combined, dried with sodium sulfate, filtered, concentrated, and purified with silica gel chromatography to afford crude product (110 mg) as an orange foam. ESI MS m/z 1080 [M+H]+.

Step 2. (S)-3-acetamido-4-(((S)-1-(((S)-1-((6-(4-((8-benzyl-3-oxo-6-phenyl-3,7-dihydroimidazo[1,2-a]pyrazin-2-yl)methyl)-2-fluorophenoxy)hexyl)amino)-3-carboxy-1-oxopropan-2-yl)amino)-3-carboxy-1-oxopropan-2-yl)amino)-4-oxobutanoic acid (JRW-0806)

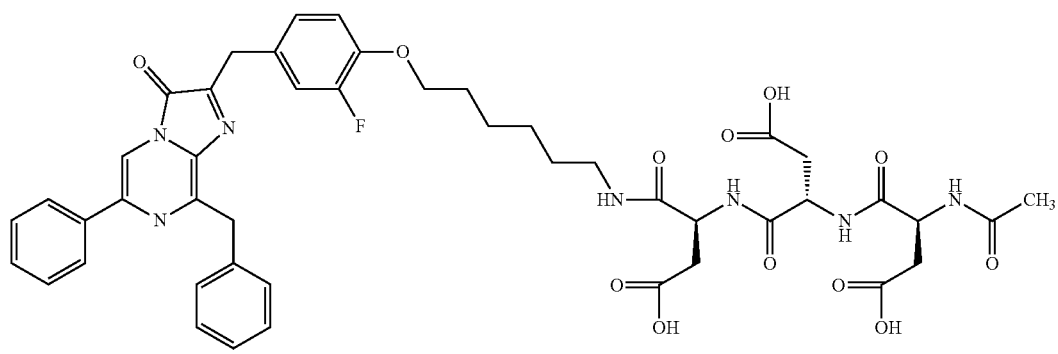 [SMILES: CC(=O)N[C@@H](CC(=O)O)C(=O)N[C@@H](CC(=O)O)C(=O)N[C@@H](CC(=O)O)C(=O)NCCCCCCOc1ccc(Cc2nc3c(Cc4ccccc4)[nH]c(-c4ccccc4)cn-3c2=O)cc1F]

Following general procedure F, tert-butyl (S)-3-acetamido-4-(((S)-1-(((S)-1-((6-(4-((8-benzyl-3-oxo-6-phenyl-3,7-dihydroimidazo[1,2-a]pyrazin-2-yl)methyl)-2-fluorophenoxy)hexyl)amino)-4-(tert-butoxy)-1,4-dioxobutan-2-yl)amino)-4-(tert-butoxy)-1,4-dioxobutan-2-yl)amino)-4-oxobutanoate (110 mg, 0.10 mmol) was reacted with trifluoroacetic acid (1 mL) to afford the desired product (49 mg, 70% over two steps) as a red solid. Note: isolated material was not pure, impurities present. ESI MS m/z 913 [M+H]+; HPLC 87.8% (AUC), $T_R$ 4.40 min; UV (MeOH) λ 432 nm, ε 2860.

Example 24 tert-butyl 3-(8-benzyl-2-(furan-2-ylmethyl)-3-oxo-3,7-dihydroimidazo[1,2-a]pyrazin-6-yl)benzoate (JRW-0755)

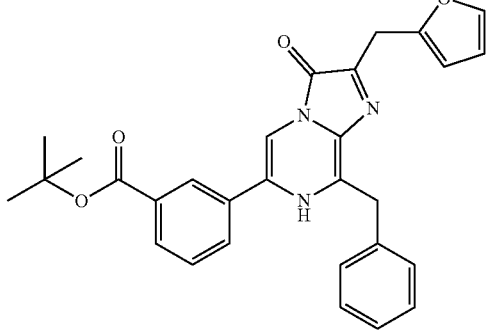

Step 1. tert-butyl 3-(5-amino-6-benzylpyrazin-2-yl)benzoate (JRW-0750)

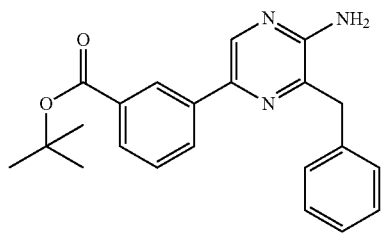 [SMILES: CC(C)(C)OC(=O)c1cccc(-c2cnc(N)c(Cc3ccccc3)n2)c1]

To a degassed suspension of 3-benzyl-5-bromopyrazin-2-amine (190 mg, 0.72 mmol), (3-(tert-butoxycarbonyl)phenyl)boronic acid (191 mg, 0.86 mmol), and [1,1'-bis(diphenylphosphino)ferrocene]dichloropalladium(II) (58 mg, 0.072 mmol) in dioxane (5 mL), cesium carbonate (2.2 mL, 1 M, 2.2 mmol) was added. The mixture was heated to 75° C. for 30 min, diluted with ethyl acetate, and washed with water. The organic layers were combined, dried with sodium sulfate, filtered, concentrated, and purified with silica gel chromatography to afford the desired product (205 mg, 79%) as a light yellow solid. $^1$H NMR (300 MHz, CDCl$_3$) δ 8.62-8.45 (m, 2H), 8.19-7.90 (m, 2H), 7.60-7.22 (m, 6H), 4.57 (s, 2H), 4.20 (s, 2H), 1.82-1.47 (m, 9H); ESI MS m/z 362 [M+H]+.

Step 2. tert-butyl 3-(6-benzyl-5-((1-(diethoxyphosphoryl)-2-methoxy-2-oxoethyl)amino)pyrazin-2-yl)benzoate (JRW-0751)

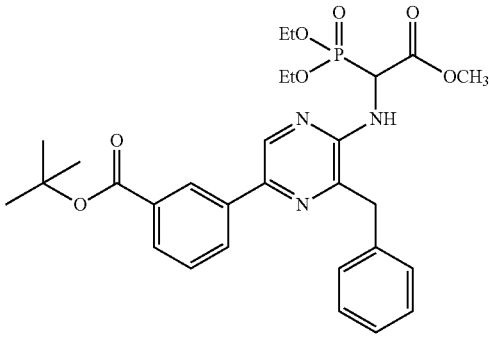 [SMILES: CCOP(=O)(OCC)C(Nc1ncc(-c2cccc(C(=O)OC(C)(C)C)c2)nc1Cc1ccccc1)C(=O)OC]

To a solution of tert-butyl 3-(5-amino-6-benzylpyrazin-2-yl)benzoate (205 mg, 0.56 mmol) in chlorobenzene (5 mL), methyl 2-diazo-2-(diethoxyphosphoryl)acetate (401 mg, 1.7 mmol) and rhodium acetate (12 mg, 0.028 mmol) was added. The mixture was heated 100° C. for 24 h. The mixture was diluted with ethyl acetate, added to Celite, concentrated, and purified with silica gel chromatography to afford the desired crude product (442 mg) as a dark brown oil. $^1$H NMR (300 MHz, CDCl$_3$) δ 8.60-8.52 (m, 1H), 8.44, (s, 1H), 8.15-8.08 (m, 1H), 8.01-7.95 (m, 1H), 7.50 (t, J=7.8, 1H), 7.40-7.20 (m, 5H), 5.43-5.12 (m, 2H), 4.33-4.13 (m, 4H), 3.74 (s, 3H), 1.61 (s, 9H), 1.28-1.13 (m, 6H); ESI MS m/z 570 [M+H]+.

Step 3. tert-butyl (Z)-3-(8-benzyl-2-(furan-2-ylmethylene)-3-oxo-2,3-dihydroimidazo[1,2-a]pyrazin-6-yl)benzoate (JRW-0754)

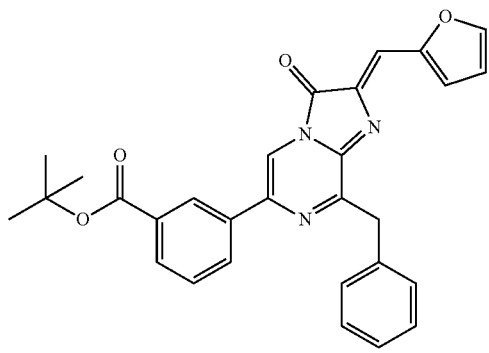 [SMILES: CC(C)(C)OC(=O)c1cccc(C2=CN3C(=O)/C(=C/c4ccco4)N=C3C(Cc3ccccc3)=N2)c1]

Following general procedure D, furfural (111 mg, 1.2 mmol) was reacted with tert-butyl 3-(6-benzyl-5-((1-(diethoxyphosphoryl)-2-methoxy-2-oxoethyl)amino)pyrazin-2-yl)benzoate (440 mg, 0.77 mmol) to afford the desired crude product (369 mg) as a red black solid.

Step 4. tert-butyl 3-(8-benzyl-2-(furan-2-ylmethyl)-3-oxo-3,7-dihydroimidazo[1,2-a]pyrazin-6-yl)benzoate (JRW-0755)

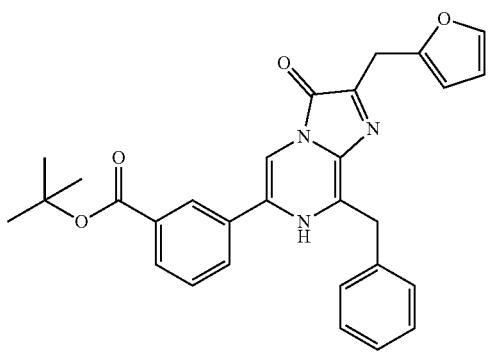 [SMILES: CC(C)(C)OC(=O)c1cccc(-c2cn3c(=O)c(Cc4ccco4)nc-3c(Cc3ccccc3)[nH]2)c1]

Following general procedure E, tert-butyl (Z)-3-(8-benzyl-2-(furan-2-ylmethylene)-3-oxo-2,3-dihydroimidazo[1,2-a]pyrazin-6-yl)benzoate (0.77 mmol) was reacted with sodium borohydride (87 mg, 2.3 mmol) to afford the desired product (130 mg, 35% over two steps) as a yellow foam. $^1$H NMR (300 MHz, CD$_3$OD) δ 8.28 (br s, 1H), 8.12-7.80 (m, 3H), 7.64-7.17 (m, 7H), 6.41-6.00 (m, 2H), 4.44 (s, 2H), 4.19 (s, 2H), 1.60 (s, 9H); ESI MS m/z 480 [M−H]−; HPLC 90.0% (AUC), T$_R$ 5.52 min; UV (MeOH) λ 306 nm, ε 21203.

Example 25

3-(8-benzyl-2-(furan-2-ylmethyl)-3-oxo-3,7-dihydroimidazo[1,2-a]pyrazin-6-yl)benzoic acid (JRW-0756)

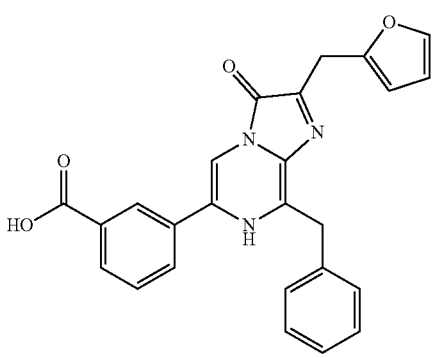 [SMILES: O=C(O)c1cccc(-c2cn3c(=O)c(Cc4ccco4)nc-3c(Cc3ccccc3)[nH]2)c1]

Following general procedure F, tert-butyl 3-(8-benzyl-2-(furan-2-ylmethyl)-3-oxo-3,7-dihydroimidazo[1,2-a]pyrazin-6-yl)benzoate (115 mg, 0.24 mmol) was reacted with trifluoroacetic acid (1 mL) to afford the desired product (64 mg, 63%) as a brown solid. $^1$H NMR (300 MHz, CD$_3$OD) δ 8.73 (s, 1H), 8.64 (t, J=1.6, 1H), 8.27-8.15 (m, 1H), 8.15-8.02 (m, 1H), 7.60 (t, J=7.8, 1H), 7.54-7.39 (m, 3H), 7.39-7.18 (m, 3H), 6.38-6.24 (m, 2H), 4.63 (s, 2H), 4.37 (s, 2H); ESI MS m/z 425 [M+H]+; HPLC 91.3% (AUC), T$_R$ 3.63 min; UV (MeOH) λ 306 nm, ε 19518.

Example 26

4-(8-benzyl-2-(furan-2-ylmethyl)-3-oxo-3,7-dihydroimidazo[1,2-a]pyrazin-6-yl)benzoic acid (JRW-0790)

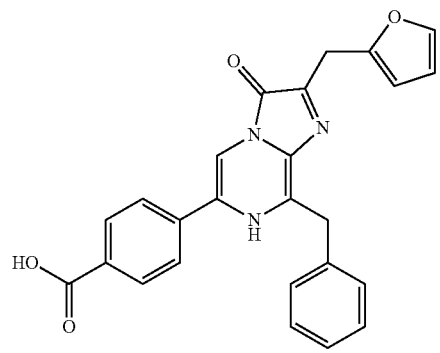 [SMILES: O=C(O)c1ccc(-c2cn3c(=O)c(Cc4ccco4)nc-3c(Cc3ccccc3)[nH]2)cc1]

Step 1. tert-butyl 4-(5-amino-6-benzylpyrazin-2-yl)benzoate (JRW-0781)

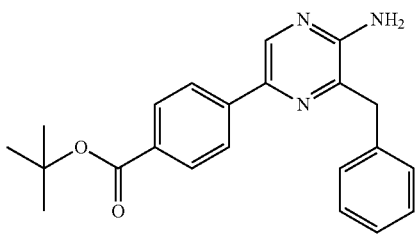 [SMILES: CC(C)(C)OC(=O)c1ccc(-c2cnc(N)c(Cc3ccccc3)n2)cc1]

To a degassed suspension of 3-benzyl-5-bromopyrazin-2-amine (190 mg, 0.72 mmol), (4-(tert-butoxycarbonyl)phenyl)boronic acid (191 mg, 0.86 mmol), and [1,1'-bis(diphenylphosphino)ferrocene]dichloropalladium(II) (58 mg, 0.072 mmol) in dioxane (5 mL), cesium carbonate (2.2 mL, 1 M, 2.2 mmol) was added. The mixture was heated to 75° C. for 30 min, diluted with ethyl acetate, and washed with water. The organic layers were combined, dried with sodium sulfate, filtered, concentrated, and purified with silica gel chromatography to afford the desired product (240 mg, 92%) as a light yellow solid. $^1$H NMR (300 MHz, CDCl$_3$) δ 8.45 (s, 1H), 8.08-7.97 (m, 4H), 7.38-7.19 (m, 5H), 4.55 (s, 2H), 4.20 (s, 2H), 1.62 (s, 9H); ESI MS m/z 362 [M+H]+.

Step 2. tert-butyl 4-(6-benzyl-5-((1-(diethoxyphosphoryl)-2-methoxy-2-oxoethyl)amino)pyrazin-2-yl)benzoate (JRW-0783)

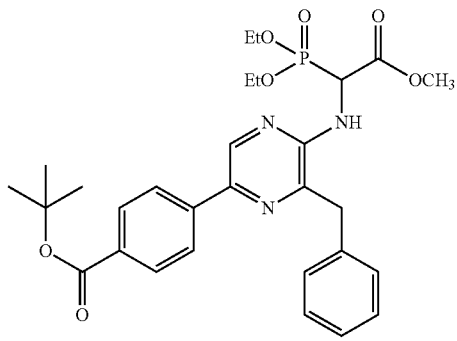 [SMILES: CCOP(=O)(OCC)C(Nc1ncc(-c2ccc(C(=O)OC(C)(C)C)cc2)nc1Cc1ccccc1)C(=O)OC]

To a solution of tert-butyl 4-(5-amino-6-benzylpyrazin-2-yl)benzoate (240 mg, 0.66 mmol) in chlorobenzene (5 mL), methyl 2-diazo-2-(diethoxyphosphoryl)acetate (470 mg, 2.0 mmol) and rhodium acetate (15 mg, 0.033 mmol) was added. The mixture was heated 100° C. for 24 h. The mixture was diluted with ethyl acetate, added to Celite, concentrated, and purified with silica gel chromatography to afford the desired crude product (620 mg) as a dark brown oil. ESI MS m/z 570 [M+H]+.

Step 3. tert-butyl (Z)-4-(8-benzyl-2-(furan-2-ylmethylene)-3-oxo-2,3-dihydroimidazo[1,2-a]pyrazin-6-yl)benzoate (JRW-0787)

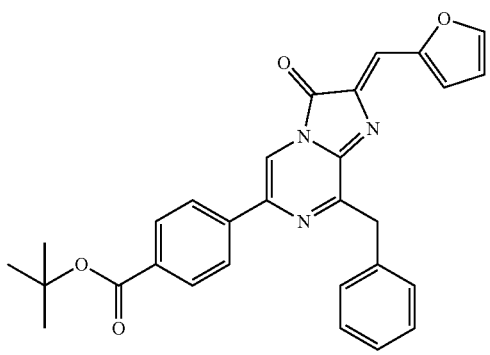 [SMILES: CC(C)(C)OC(=O)c1ccc(C2=CN3C(=O)/C(=C/c4ccco4)N=C3C(Cc3ccccc3)=N2)cc1]

Following general procedure D, furfural (95 mg, 1.0 mmol) was reacted with tert-butyl 3-(6-benzyl-5-((1-(diethoxyphosphoryl)-2-methoxy-2-oxoethyl)amino)pyrazin-2-yl)benzoate (0.66 mmol) to afford the desired crude product (590 mg) as a red black solid.

Step 4. tert-butyl 4-(8-benzyl-2-(furan-2-ylmethyl)-3-oxo-3,7-dihydroimidazo[1,2-a]pyrazin-6-yl)benzoate (JRW-0788)

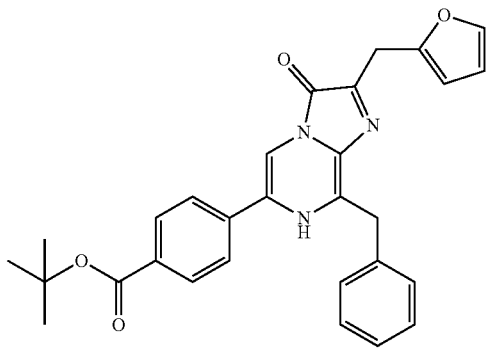 [SMILES: CC(C)(C)OC(=O)c1ccc(-c2cn3c(=O)c(Cc4ccco4)nc-3c(Cc3ccccc3)[nH]2)cc1]

Following general procedure E, tert-butyl (Z)-4-(8-benzyl-2-(furan-2-ylmethylene)-3-oxo-2,3-dihydroimidazo[1,2-a]pyrazin-6-yl)benzoate (0.66 mmol) was reacted with sodium borohydride (75 mg, 2.0 mmol) to afford the desired product (72 mg, 22% over three steps) as an orange red foam.

Step 5. 4-(8-benzyl-2-(furan-2-ylmethyl)-3-oxo-3,7-dihydroimidazo[1,2-a]pyrazin-6-yl)benzoic acid (JRW-0790)

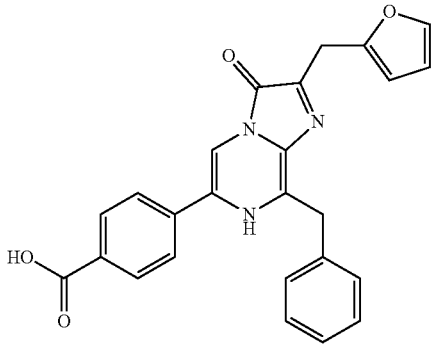 [SMILES: O=C(O)c1ccc(-c2cn3c(=O)c(Cc4ccco4)nc-3c(Cc3ccccc3)[nH]2)cc1]

Following general procedure F, tert-butyl 4-(8-benzyl-2-(furan-2-ylmethyl)-3-oxo-3,7-dihydroimidazo[1,2-a]pyrazin-6-yl)benzoate (72 mg, 0.15 mmol) was reacted with trifluoroacetic acid (1 mL) to afford the desired product (45 mg, 71%) as an orange solid. $^1$H NMR (300 MHz, CD$_3$OD) δ 8.21-7.78 (m, 5H), 7.55-7.19 (m, 6H), 6.35-6.28 (m, 1H), 6.15-6.07 (m, 1H), 4.43 (s, 2H), 4.18 (s, 2H); ESI MS m/z 426 [M+H]+; HPLC 97.9% (AUC), T$_R$ 4.31 min; UV (MeOH) λ 396 nm, ε 4554.

Example 27

6-(4-((6-aminohexyl)oxy)phenyl)-8-benzyl-2-(furan-2-ylmethyl)imidazo[1,2-a]pyrazin-3(7H)-one (JRW-0817)

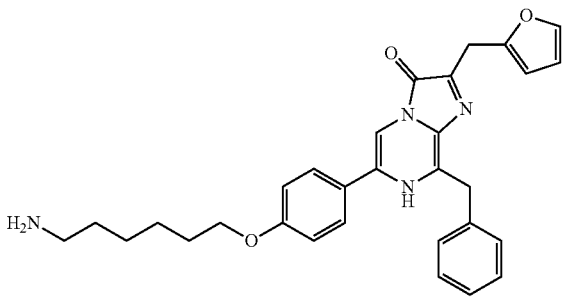 [SMILES: NCCCCCCOc1ccc(-c2cn3c(=O)c(Cc4ccco4)nc-3c(Cc3ccccc3)[nH]2)cc1]

Step 1. tert-butyl (6-(4-(5-amino-6-benzylpyrazin-2-yl)phenoxy)hexyl)carbamate (JRW-0807)

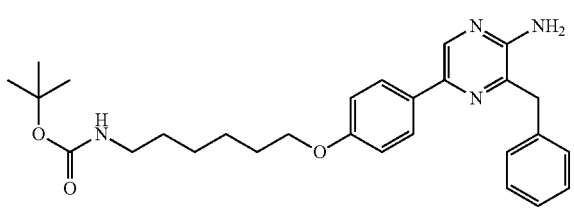 [SMILES: CC(C)(C)OC(=O)NCCCCCCOc1ccc(-c2cnc(N)c(Cc3ccccc3)n2)cc1]

Following general procedure A, 4-(5-amino-6-benzylpyrazin-2-yl)phenol (250 mg, 0.90 mmol) was reacted with tert-butyl (6-bromohexyl)carbamate (252 mg, 0.90 mmol) to afford the desired product (350 mg, 81%) as a brown foam. $^1$H NMR (300 MHz, CDCl$_3$) δ 8.32 (s, 1H), 7.86 (d, J=8.8, 2H), 7.39-7.20 (m, 5H), 6.97 (d, J=8.8, 2H), 4.58-4.43 (m, 1H), 4.35 (s, 2H), 4.17 (s, 2H), 4.00 (t, J=6.5, 2H), 3.20-3.03 (m, 2H), 1.87-1.75 (m, 2H), 1.61-1.34 (m, 15H); ESI MS m/z 477 [M+H]+.

Step 2. methyl 2-((3-benzyl-5-(4-((6-((tert-butoxy-carbonyl)amino)hexyl)oxy)phenyl)pyrazin-2-yl)amino)-2-(diethoxyphosphoryl)acetate (JRW-0809)

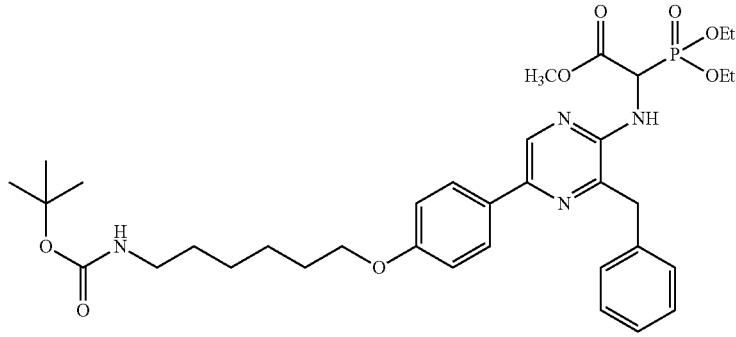 [SMILES: CCOP(=O)(OCC)C(Nc1ncc(-c2ccc(OCCCCCCNC(=O)OC(C)(C)C)cc2)nc1Cc1ccccc1)C(=O)OC]

To a solution of tert-butyl (6-(4-(5-amino-6-benzylpyrazin-2-yl)phenoxy)hexyl)carbamate (350 mg, 0.73 mmol) in chlorobenzene (5 mL), methyl 2-diazo-2-(diethoxyphosphoryl)acetate (520 mg, 2.2 mmol) and rhodium acetate (16 mg, 0.036 mmol) was added. The mixture was heated 100° C. for 24 h. The mixture was diluted with ethyl acetate, added to Celite, concentrated, and purified with silica gel chromatography to afford the desired crude product (170 mg, 33%). $^1$H NMR (300 MHz, CDCl$_3$) δ 8.33 (s, 1H), 7.85 (d, J=8.6, 2H), 7.36-7.19 (m, 5H), 6.96 (d, J=8.7, 2H), 5.33-5.09 (m, 2H), 4.60-4.40 (m, 1H), 4.23 (s, 2H), 4.15-3.88 (m, 6H), 3.73 (s, 3H), 3.18-3.03 (m, 2H), 1.88-1.74 (m, 2H), 1.57-1.30 (m, 15H), 1.29-1.14 (m, 6H); ESI MS m/z 685 [M+H]+.

Step 3. tert-butyl (Z)-(6-(4-(8-benzyl-2-(furan-2-ylmethylene)-3-oxo-2,3-dihydroimidazo[1,2-a]pyrazin-6-yl)phenoxy)hexyl)carbamate (JRW-0814)

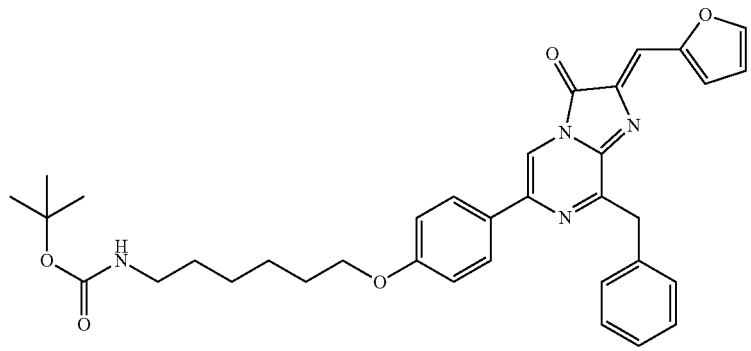 [SMILES: CC(C)(C)OC(=O)NCCCCCCOc1ccc(C2=CN3C(=O)/C(=C/c4ccco4)N=C3C(Cc3ccccc3)=N2)cc1]

Following general procedure D, furfural (33 mg, 0.33 mmol) was reacted with methyl 2-((3-benzyl-5-(4-((6-((tert-butoxycarbonyl)amino)hexyl)oxy)phenyl)pyrazin-2-yl)amino)-2-(diethoxyphosphoryl)acetate (160 mg, 0.23 mmol) to afford the desired crude product as a black solid.

Step 4. tert-butyl (6-(4-(8-benzyl-2-(furan-2-ylmethyl)-3-oxo-3,7-dihydroimidazo[1,2-a]pyrazin-6-yl)phenoxy)hexyl)carbamate (JRW-0815)

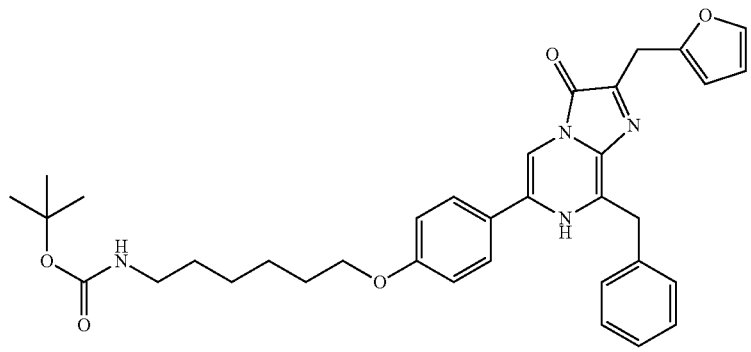 [SMILES: CC(C)(C)OC(=O)NCCCCCCOc1ccc(-c2cn3c(=O)c(Cc4ccco4)nc-3c(Cc3ccccc3)[nH]2)cc1]

Following general procedure E, tert-butyl (Z)-(6-(4-(8-benzyl-2-(furan-2-ylmethylene)-3-oxo-2,3-dihydroimidazo[1,2-a]pyrazin-6-yl)phenoxy)hexyl)carbamate (0.23 mmol) was reacted with sodium borohydride (44 mg, 1.2 mmol) to afford the desired product (20 mg, 14% over two steps) as a yellow solid. ESI MS m/z 597 [M+H]+.

Step 5. 6-(4-((6-aminohexyl)oxy)phenyl)-8-benzyl-2-(furan-2-ylmethyl)imidazo[1,2-a]pyrazin-3(7H)-one (JRW-0817)

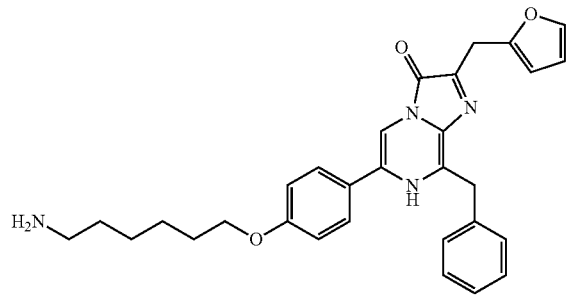 [SMILES: NCCCCCCOc1ccc(-c2cn3c(=O)c(Cc4ccco4)nc-3c(Cc3ccccc3)[nH]2)cc1]

Following general procedure F, tert-butyl (6-(4-(8-benzyl-2-(furan-2-ylmethyl)-3-oxo-3,7-dihydroimidazo[1,2-a]pyrazin-6-yl)phenoxy)hexyl)carbamate (20 mg, 0.033 mmol) was reacted with trifluoroacetic acid (1 mL) to afford the desired product (18 mg, quant) as a brown solid. $^1$H NMR (300 MHz, CD$_3$OD) δ 7.75-7.53 (m, 3H), 7.45-7.35 (m, 3H), 7.34-7.19 (m, 3H), 7.00 (d, J=8.5, 2H), 6.33-6.29 (m, 1H), 6.12-6.08 (m, 1H), 4.42 (s, 2H), 4.18 (s, 2H), 4.07-3.98 (m, 2H), 3.02-2.84 (m, 2H), 1.92-1.38 (m, 8H); ESI MS m/z 497 [M+H]+; HPLC 98.6% (AUC), $T_R$ 3.93 min; UV (MeOH) λ 428 nm, ε 4535.

Example 28

Luminescent Properties

Figure 1B:
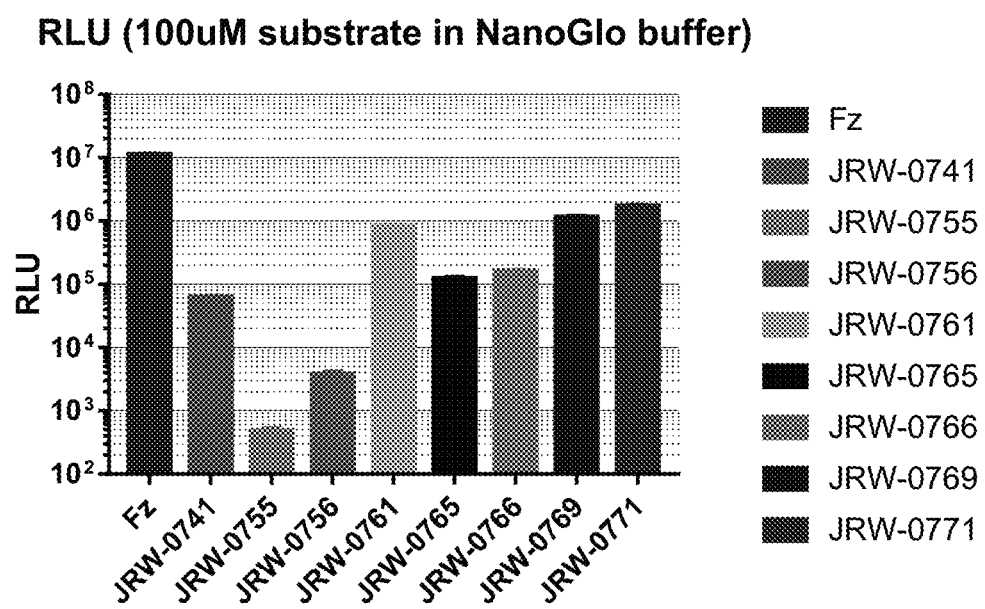
Figure 1C:
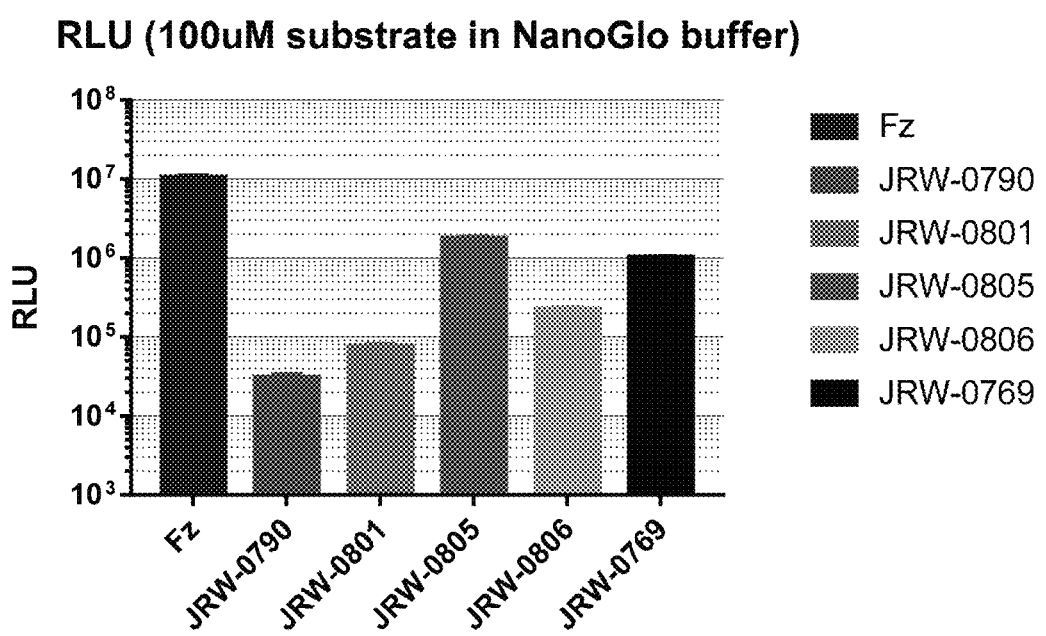

Luminescence Assay Procedure:
Each compound to be screened was dissolved in DMSO (5 mM) and then further diluted to 100 uM in NANO-GLO® Luciferase Assay Buffer. Each diluted substrate was then combined in equal volumes with purified NANOLUC® Luciferase diluted into CO$_2$ independent media+10% FBS. Initial light output for each substrate was measured in a GloMax®-Multi+ luminometer three minutes after substrate addition and then at five minute intervals as a means to determine signal half-life. The bioluminescent activity of exemplary compounds is depicted in FIGS. 1A-C. Km was calculated using GraphPad Prism using non linear Michaelis-Menten regression. Light output, signal half life, and Km values are summarized in Table 1.

TABLE 1

| Compound | RLU at 100 uM | Signal Half Life | Km | AutoLuminescence in NanoGlo Buffer |
|---|---|---|---|---|
| Furimazine | 1 | 1 | 1 | 1 |
| TAK-0039 | 0.0077 | 5.1 | 5 | 0.6 |
| JRW-0665 | 0.0055 | 2.1 | 5.6 | 0.4 |
| JRW-0682 | 0.0024 | 4.1 | 6.2 | 0.3 |
| JRW-0684 | 0.0057 | 3.2 | 4.5 | 1.2 |
| JRW-0692 | 0.0025 | 4.1 | 5.6 | 0.6 |
| JRW-0703 | 0.016 | 2.6 | 6.3 | 0.8 |

TABLE 1-continued

| Compound | RLU at 100 uM | Signal Half Life | Km | AutoLuminescence in NanoGlo Buffer |
|---|---|---|---|---|
| JRW-0714 | 0.0013 | 4.1 | 5.5 | 0.5 |
| JRW-0713 | 0.00081 | 3.1 | 5.6 | 1.3 |
| JRW-0716 | 0.0022 | 3.5 | 3.4 | 2.1 |
| JRW-0719 | 0.0011 | 5.6 | 4.5 | 0.4 |
| JRW-0720 | 0.0085 | 4.4 | 5.1 | 0.4 |
| JRW-0722 | 0.023 | 2.7 | 5.2 | 0.9 |
| JRW-0725 | 0.013 | 3.4 | 4.1 | 0.4 |
| JRW-0726 | 0.061 | 2.5 | 3 | 0.8 |
| JRW-0728 | 0.14 | 1.4 | 4.5 | 0.8 |
| JRW-0741 | 0.0057 | 2.9 | 4.4 | 1.2 |
| JRW-0755 | 0.000043 | not calculated | 1 | 0.6 |
| JRW-0756 | 0.00034 | not calculated | 3.7 | 2.3 |
| JRW-0761 | 0.075 | 1.5 | 3.2 | 4.6 |
| JRW-0765 | 0.011 | 2 | not calculated | 1.1 |
| JRW-0766 | 0.015 | 2.4 | 5.3 | 1 |
| JRW-0769 | 0.1 | 2.5 | 2.6 | 1 |
| JRW-0771 | 0.15 | 2.1 | 2.5 | 1.2 |
| JRW-0790 | 0.0029 | 18.8 | 5.7 | 9 |
| JRW-0801 | 0.0073 | 2.5 | 4.1 | 0.6 |
| JRW-0805 | 0.17 | 1 | 3.6 | 2 |
| JRW-0806 | 0.021 | 4.6 | 7.3 | 0.7 |

Data in Table 1 demonstrate that the disclosed compounds are substrates for NanoLuc despite having a variety of functional groups. The values are represented as relative values where furimazine is set to 1 in each category (~1.0× $10^7$ RLU at 2.5 ng/mL NanoLuc).

Example 29

Cell Permeability and Bioluminescent Activity

Cell Culture:
HEK293 cells were maintained in DMEM containing 100 IU/ml penicillin, 100 µg/ml streptomycin, and 10% fetal calf serum at 37° C. in 5% CO$_2$. Dulbecco's modified eagle medium (DMEM), Opti-MEM, Penicillin/Streptomycin, and Trypsin-EDTA are purchased from Life Technologies (Carlsbad). Fetal calf serum (FBS) is purchased from HyClone (GE Healthcare). Microtiter plates were purchased from Corning.

Cell-Based Luciferase Assay:
HEK293 cells were transiently transfected with two different integral membrane NanoLuc fusion proteins: 1) NanoLuc:KDR, presenting NanoLuc on the cell surface; 2) KDR:NanoLuc, presenting NanoLuc in the interior of the cell. After 24 hours, transfected cells were collected, resuspended in OptiM at 200,000 cell/ml and plated into wells of white, 96-well plates at 100 µL/well. For luminescent measurements, cells were treated with the indicated substrates at a final concentration of 10 µM or 20 µM in the presence or absence of 20 µM cell impermeable NanoLuc inhibitor JRW-0344. The luminescent signal was analyzed 3 minutes after substrate addition using a GLOMAX® Discover multimode detection plate reader (Promega).

Figure 2A:
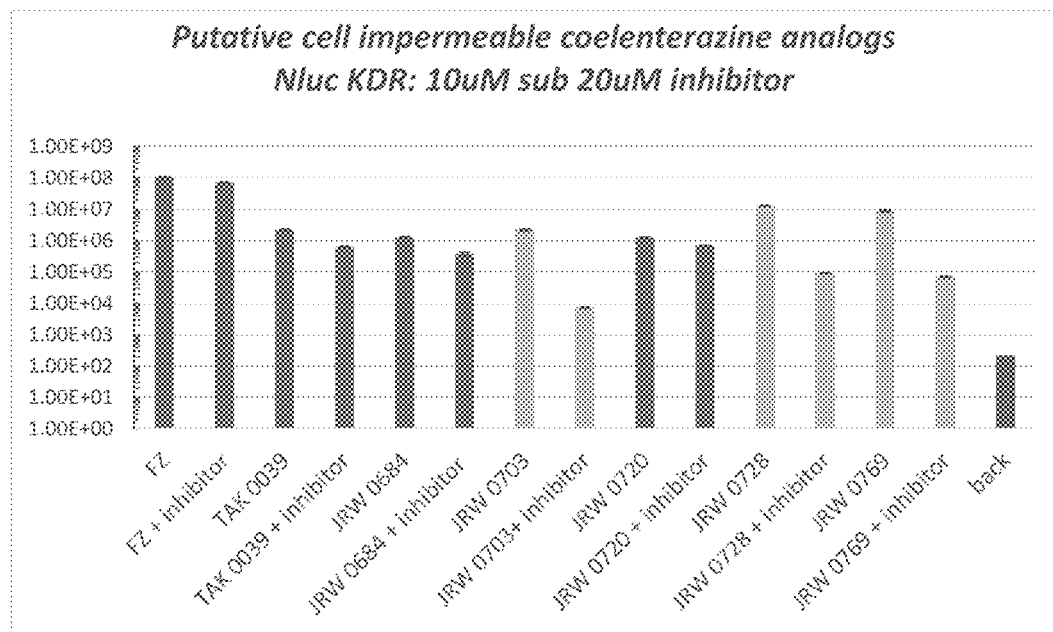
FIGS. 2A-2D show extracellular bioluminescent activity of exemplary compounds in HEK293 cells. HEK293 cells were transfected with two different membrane bound NANOLUC® fusions: 1) NanoLuc:KDR, presenting NanoLuc on the outside of the membrane; 2) KDR:NanoLuc, presenting NanoLuc on the inside of the membrane. The cell impermeable NANOLUC® inhibitor JRW-0344 (disclosed in U.S. Ser. No. 15/192,420 to Duellman et al., "THIENOPYRROLE COMPOUNDS AND USES THEREOF," filed Jun. 24, 2016), was added to the cells to inhibit extracellular bioluminescent activity.
Figure 2B:
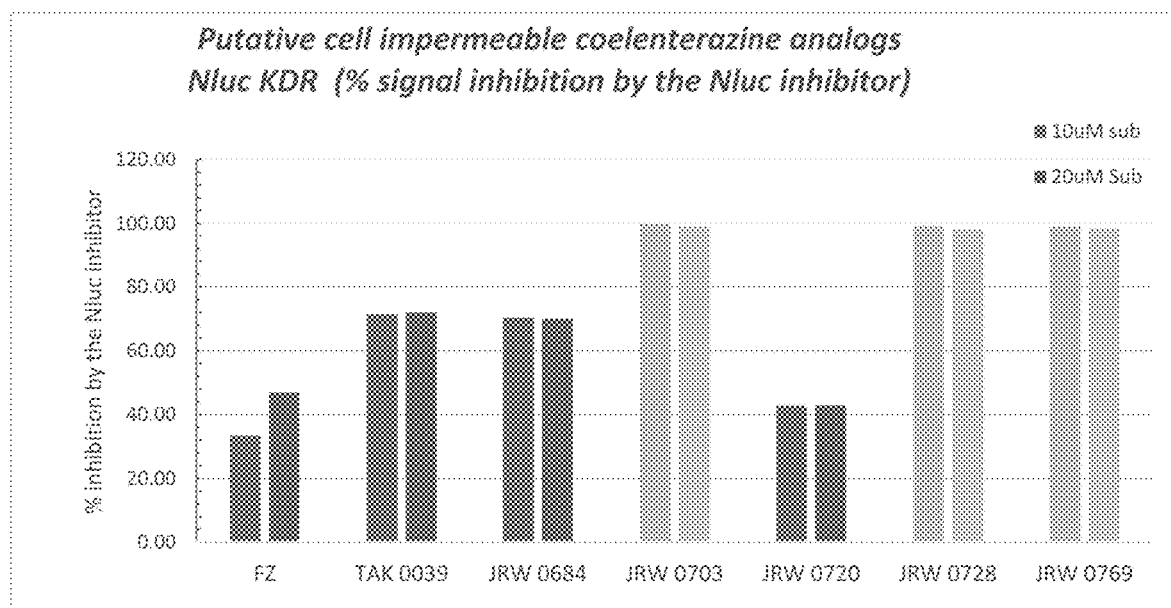
Figure 2C:
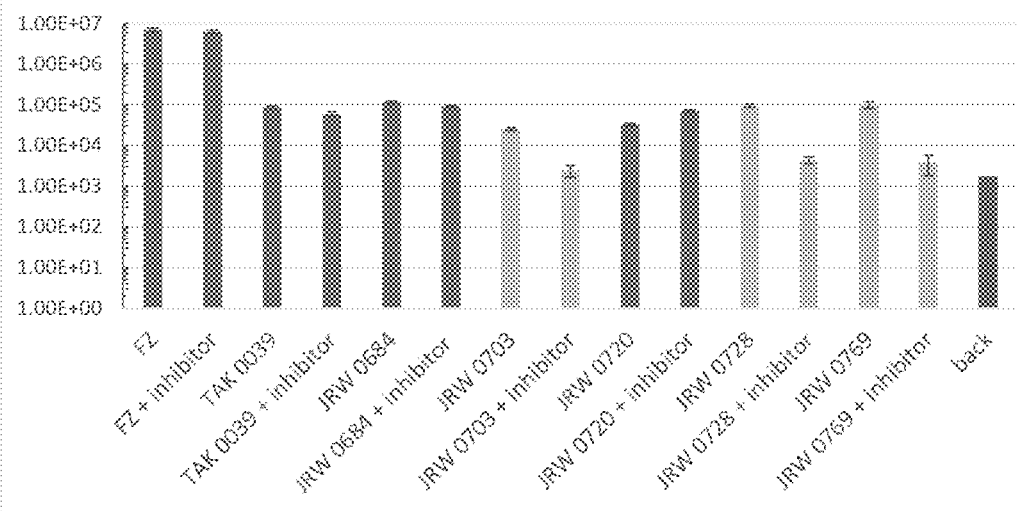
Figure 2D:
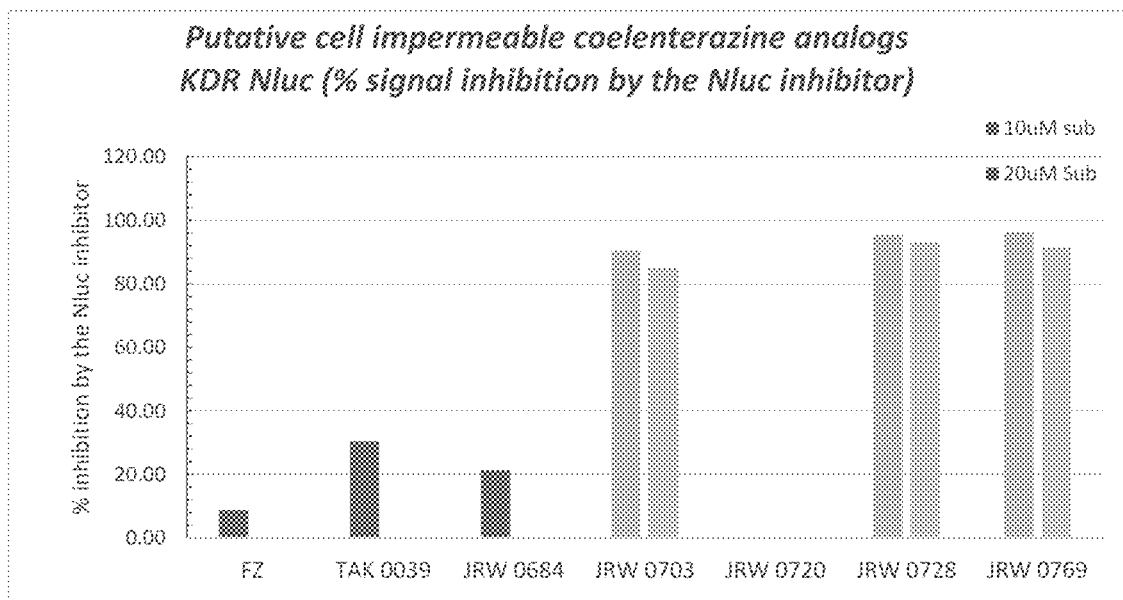

The difference in luminescent signal in the presence and absence of JRW-0344 is depicted in FIGS. 2A-D. These data indicate significant inhibition of impermeable substrates by the extracellular inhibitor. On the contrary, permeable substrates that can access NanoLuc inside and outside the cell membrane are not significantly affected by the extracellular inhibitor. FIG. 2A displays the luminescence from cells expressing NanoLuc:KDR and treated with 10 µM substrate±20 µM PBI 6096. Larger differences in RLU's in the presence and absence of the inhibitor were observed for cells treated with substrates containing a sulfonate group (JRW-0703, JRW-0728, JRW-0769). Small differences in RLU's in the presence and absence of the inhibitor were observed for cells treated with substrates containing an amine (TAK-0039), a carboxylate (JRW-0684), or a bromide (JRW-0720). FIG. 2B shows no significant differences in percent inhibition of cells treated with 10 μM and 20 μM substrate by the NanoLuc inhibitor JRW-0344. FIG. 2C shows the RLU data for cells expressing KDR:Nluc and treated with 10 μM substrate and ±20 μM JRW-0344. The results indicate that sulfonated, impermeable substrates (JRW-0703, JRW-0728, JRW-0769) are much dimmer and can be inhibited close to background level by the extracellular inhibitor. However, RLU's from cell permeable substrates (TAK-0039, JRW-0684, JRW-0720) are not affected by the extracellular inhibitor. FIG. 2D shows no significant differences in percent inhibition of cells treated with 10 μM and 20 μM substrate by the NanoLuc inhibitor JRW-0344.

Figure 3A:
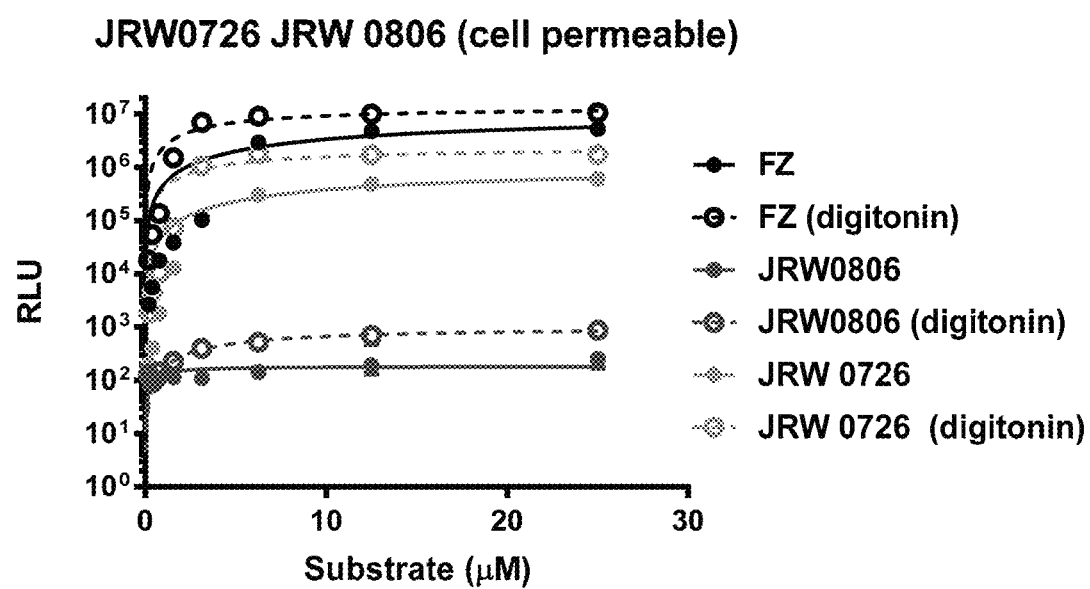
FIGS. 3A-D show the activities of cell permeable and cell impermeable compounds at various substrate concentrations. HEK293 cells were transfected (1:100 carrier DNA) with the fusion protein KDR:NanoLuc, which presents membrane bound NanoLuc on the inside of the membrane. Cells were then treated with digitonin (for lytic format) or JRW-0344 (for live cell format). Both sets were treated with varying substrate concentrations to give Michaelis-Menten type plots. Substrates that are cell permeable (TAK-0039, JRW-0726, JRW-0720, JRW-0806) have similar dose response curves as seen in FIGS. 3A and 3B. However, substrates that are cell impermeable (or mostly impermeable) show large differences between live and lytic cell formats (FIG. 3C). The sulfontes JRW-0703, JRW-0728, and JRW-0769 gave 100-fold lowered activity in the live cell format demonstrating that the substrates have limited access to the intracellular NanoLuc.
Figure 3B:
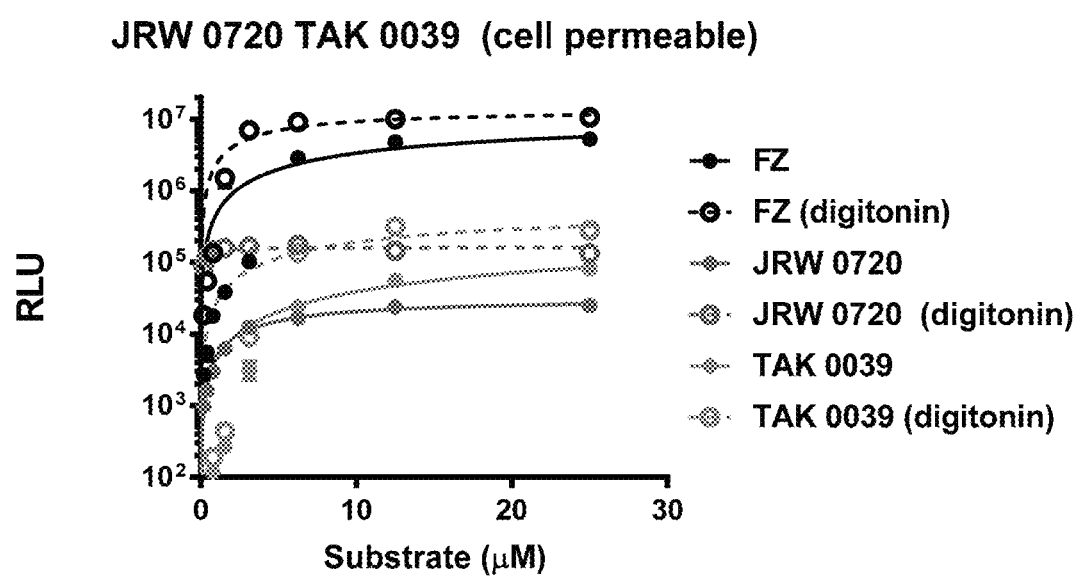
Figure 3C:
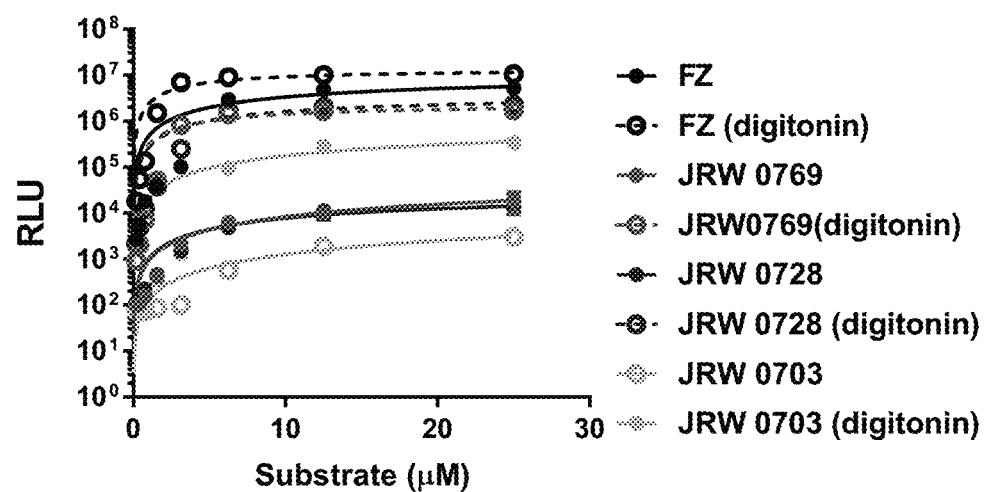
Figure 3D:
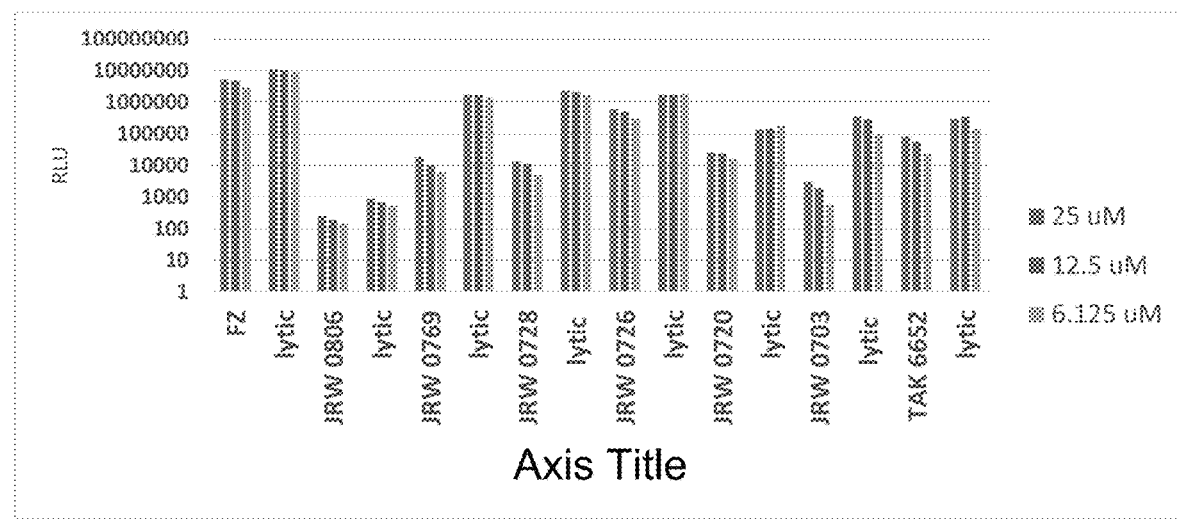
Figure 4A:
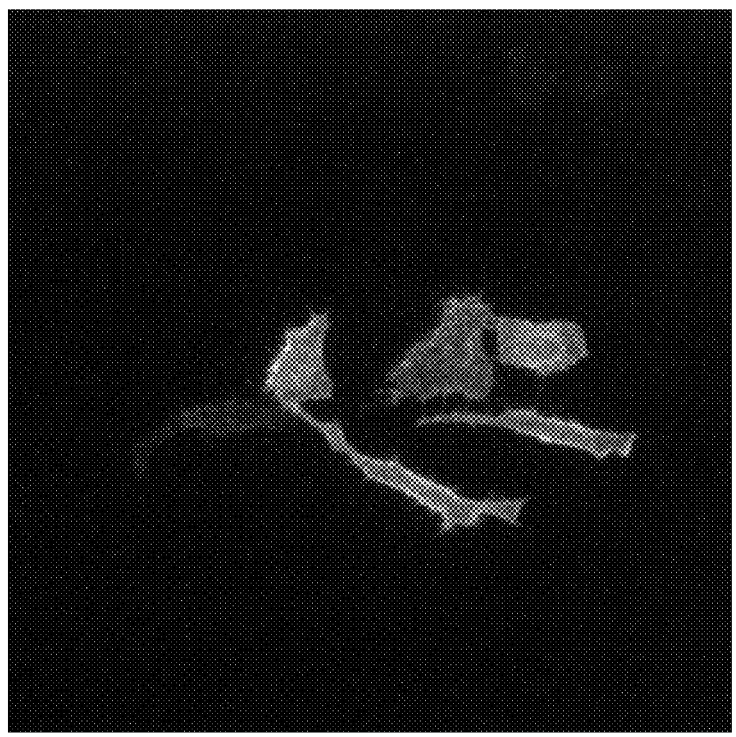
FIGS. 4A and 4B show the results of imaging of Nluc-B2AR in HeLa cells using furimazine and JRW-0769. HeLa cells were reverse transfected with an expression construct for Nluc-b2 adrenergic receptor (B2AR) and plated into a LabTEKII chambered coverslip (50,000 cells per well in 400 uL medium) and incubated overnight. For imaging, the medium was removed and replaced with $CO_2$-independent medium. Immediately before placing the sample onto the imaging instrument, Furimazine or JRW-0769 was added to the cells at a final concentration of 10 uM. Image acquisition was performed on an Olympus LV200 bioluminescence imager using a 40×/0.95 NA objective with electromultiplying gain set to 400 and an acquisition time of 0.5 sec (Furimazine) and 2.5 sec (JRW-0769).
Figure 4B:
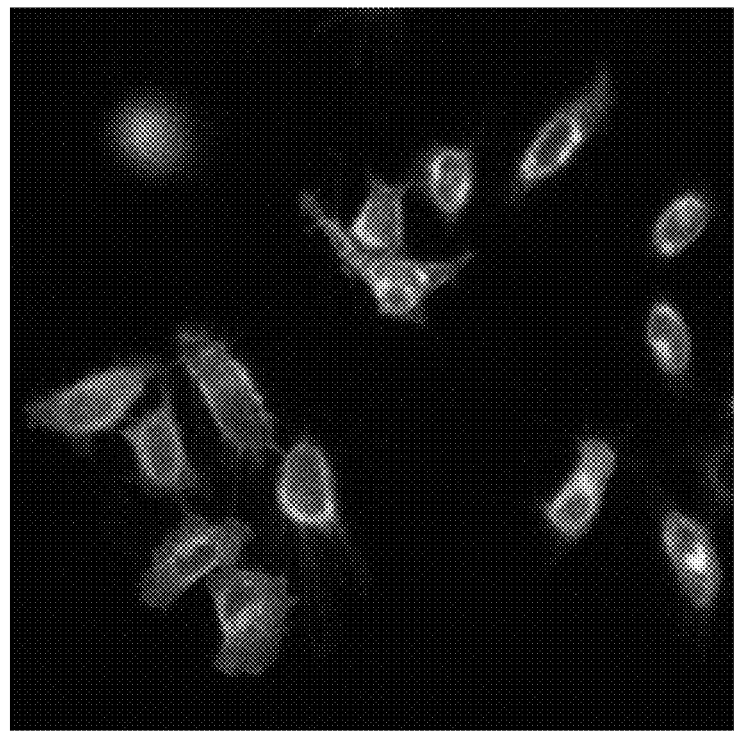

Lytic Vs. Live Cell Format:

HEK293 cells were transfected (1:100 carrier DNA) with the fusion protein KDR:NanoLuc, which presents membrane bound NanoLuc on the inside of the membrane. Cells were then treated with digitonin to lyse the cell membrane (for lytic format) or JRW-0344 (for live cell format) to compare activity of cell permeable and non-cell permeable substrates. Both sets were treated with varying substrate concentrations to give Michaelis-Menten type plots. Substrates that are cell permeable (TAK-0039, JRW-0726, JRW-0720, JRW-0806) have similar dose response curves as seen in FIGS. 3A and 3B. However, substrates that are cell impermeable (or mostly impermeable) show large differences between live and lytic cell formats (FIG. 3C). The sulfontes JRW-0703, JRW-0728, and JRW-0769 gave 100-fold lowered activity in the live cell format demonstrating that the substrates have limited access to the intracellular NanoLuc. FIG. 3D shows the highest of the three concentrations for each substrate plotted by 'live' and 'lytic' formats for each compound.

Cell Viability Assay:

After measuring luminescence, MultiTox-Fluor Multiplex Cytotoxicity Assay reagent (Promega Corporation) can be added to the plates, and the plates incubated for 30 min at 37° C. in 5% $CO_2$. Fluorescence can then be measured.

Prophetic Example 30

Detection of Cell Death

Target cells expressing NanoLuc may be used in an assay to detect cell death. HEK293 cells may be maintained in DMEM containing 100 IU/ml penicillin, 100 μg/ml streptomycin, and 10% fetal calf serum at 37° C. in 5% $CO_2$. HEK293 cells may be transfected (1:100 carrier DNA) with the fusion protein KDR:NanoLuc, which presents membrane bound NanoLuc on the inside of the membrane. The disclosed compounds may be added to the cells, and baseline luminescent signal may be analyzed using a GLOMAX® Discover multimode detection plate reader (Promega). Following baseline measurements, a compound of interest may be added to the target cells to induce cell death. The luminescent signal may be analyzed 3 minutes after addition of the compound of interest using a GLOMAX® Discover multimode detection plate reader (Promega). The difference in luminescent signal in the presence and absence of the compound of interest may be calculated and used to quantify cell death. A large difference in RLU would indicate that KDR:NanoLuc fusion protein was released from the dying target cells, enabling detection by the disclosed cell impermeable compounds.

Prophetic Example 31

Detection of Secreted Luciferase

Cells expressing secretable luciferase may be used in a method to measure secretion of luciferase from live cells. HEK293 cells may be maintained in DMEM containing 100 IU/ml penicillin, 100 μg/ml streptomycin, and 10% fetal calf serum at 37° C. in 5% $CO_2$. HEK293 cells may be transfected (1:100 carrier DNA) with a secretable luciferase. The disclosed compounds may be added to the cells, and luminescent signal may be analyzed using a GLOMAX® Discover multimode detection plate reader (Promega). For example, the sequence of wild-type luciferase may be modified to contain a signal peptide directing the protein for secretion from the cell. Upon secretion, the signal peptide could be cleaved, and the resulting wild-type luciferase may be detected by the disclosed cell-impermeable compounds.

Example 32

Imaging of Nluc-B2AR in HeLa Cells—Furimazine Vs. JRW-0769

HeLa cells were reverse transfected with an expression construct for Nluc-b2 adrenergic receptor (B2AR) and plated into a LabTEKII chambered coverslip (50,000 cells per well in 400 uL medium) and incubated overnight. For imaging, the medium was removed and replaced with $CO_2$-independent medium. Immediately before placing the sample onto the imaging instrument, Furimazine or JRW-0769 was added to the cells at a final concentration of 10 uM. Image acquisition was performed on an Olympus LV200 bioluminescence imager using a 40×/0.95 NA objective with electromultiplying gain set to 400 and an acquisition time of 0.5 sec (Furimazine) and 2.5 sec (JRW-0769).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method for imaging a cell surface, comprising:
(a) contacting the cell with a compound of formula (I):

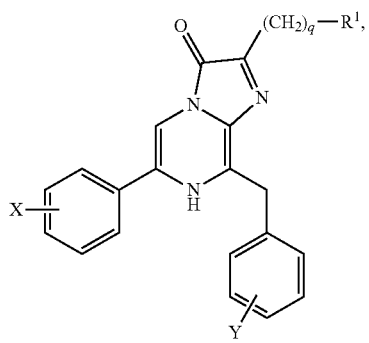

or a tautomer, or a pharmaceutically acceptable salt thereof, wherein

X and Y are independently absent, hydroxy, amino, —COOR$^2$, —SO$_2$—OR$^3$, —PO (OR$^4$)(OR$^5$), or —O—(CR$^{1a}$R$^{1b}$)$_m$—Z;

R$^1$ is optionally substituted aryl, optionally substituted heteroaryl, optionally substituted heterocycle, or optionally substituted cycloalkyl, wherein R$^1$ is substituted at least with -Q-L-Z;

Z at each occurrence is independently —COOR$^2$, —SO$_2$—OR$^3$, —PO (OR$^4$)(OR$^5$), halogen, —NR$^6$R$^7$, or —NR$^8$—CO—R$^9$;

Q is —O—, —NR$^Q$—, —NR$^Q$—CO—, —CO—NR$^Q$—, —O—CO—NR$^Q$—, or —NR$^Q$—CO—O—;

L is —(CR$^{1a}$R$^{1b}$)$_m$— or —(CR$^{1x}$R$^{1y}$—CR$^{1x}$R$^{1y}$—O)$_{t1}$—(CR$^{1x}$R$^{1y}$)$_{t2}$-Q$^1$-, wherein Q$^1$ is absent, —O—, or —NR$^{Q1}$—;

R$^2$, R$^3$, R$^4$, R$^5$, R$^8$, and R$^9$ at each occurrence are independently hydrogen, optionally substituted C$_1$-C$_8$ alkyl, optionally substituted aryl, optionally substituted cycloalkyl, optionally substituted heteroaryl, or optionally substituted heterocycle;

R$^6$ and R$^7$ at each occurrence are independently hydrogen, optionally substituted C$_1$-C$_8$ alkyl, optionally substituted aryl, optionally substituted cycloalkyl, optionally substituted heteroaryl, or optionally substituted heterocycle; or R$^6$ and R$^7$, together with the nitrogen atom to which they are attached, together form an optionally substituted ring;

R$^{1a}$, R$^{1b}$, R$^Q$, R$^{Q1}$, R$^{1x}$, and R$^{1y}$ at each occurrence are independently hydrogen, C$_1$-C$_4$ alkyl, or C$_1$-C$_4$ haloalkyl;

q is 0, 1, or 2;

m at each occurrence is independently 1-12;

t1 is 1-10; and t2 is 0-5, and (b) detecting luminescence on the cell surface;
wherein the cell expresses a protein comprising a coelenterazine-utilizing luciferase enzyme on the cell surface.

2. The method of claim 1, wherein
Q is —O—, —NH—, —NH—CO—, —CO—NH—, —O—CO—NH—, or —NH—CO—O—; and
L is —(CR$^{1a}$R$^{1b}$)$_m$—.

3. The method of claim 1, wherein
Q is —O—; and
L is —(CR$^{1a}$R$^{1b}$)$_m$—.

4. The method of claim 1 wherein
L is —(CR$^{1x}$R$^{1y}$—CR$^{1x}$R$^{1y}$—O)$_{t1}$—(CR$^{1x}$R$^{1y}$)$_{t2}$-Q$^1$-.

5. The method of claim 1, wherein R$^1$ is phenyl or furyl optionally further substituted with 1, 2, 3, or 4 substituents, each independently selected from the group consisting of halogen, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, aryloxy, phenoxy, benzyloxy, amino, alkylamino, dialkylamino, acylamino, aminoalkyl, arylamino, sulfonylamino, sulfinylamino, alkylsulfonyl, arylsulfonyl, aminosulfonyl, —COOH, ketone, amide, carbamate, silyl, substituted silyl, t-butyldimethylsilyl, alkylsulfanyl, sulfanyl, and acyl.

6. The method of claim 1, wherein R$^1$ is phenyl or furyl substituted with -Q-L-Z, in which Q is —O— and L is —(CR$^{1a}$R$^{1b}$)$_m$—.

7. The method of claim 1, wherein q is 1.

8. The method of claim 1, wherein the compound of formula (I) is a compound of formula (I-a):

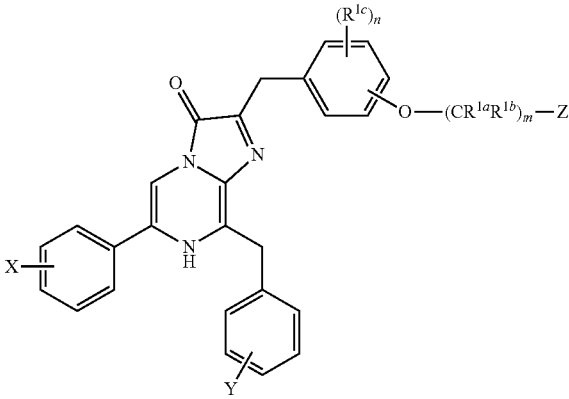

or a tautomer, or a pharmaceutically acceptable salt thereof, wherein

R$^{1c}$ is selected from the group consisting of alkyl, halogen, cyano, nitro, haloalkyl, hydroxy, hydroxyalkyl, amino, and —COOH;

n is 0, 1, 2, 3, or 4; and

X, Y, R$^{1a}$, R$^{1b}$, m, and Z are as defined in claim 1.

9. The method of claim 8, wherein at least one of X and Y is absent.

10. The method of claim 8, wherein both X and Y are absent.

11. The method of claim 8, wherein n is 0.

12. The method of claim 8, wherein n is 1 or 2, and each $R^{1c}$ is independently halogen.

13. The method of claim 8, wherein m is 3, 4, 5, 6, 7, 8, 9, or 10.

14. The method of claim 8, wherein Z is —COOR², —SO₂—OR³, or —PO(OR⁴)(OR⁵), or a pharmaceutically acceptable salt thereof.

15. The method of claim 8, wherein:
Z is —NR⁶R⁷ or —NR⁸—CO—R⁹, or a pharmaceutically acceptable salt thereof;
R⁹ is —(CR⁹ᵃR⁹ᵇ—NH—CO)ᵤ—R¹⁰;
R⁹ᵃ and R⁹ᵇ at each occurrence are independently hydrogen or C₁-C₄ alkyl optionally substituted with —COOR⁹ᶜ;
R⁹ᶜ at each occurrence is independently hydrogen or C₁-C₄ alkyl;
R¹⁰ is optionally substituted C₁-C₈ alkyl; and
u is 0-10.

16. The method of claim 8, wherein:
Z is —NR⁸—CO—R⁹, or a pharmaceutically acceptable salt thereof;
R⁸ is hydrogen; and
R⁹ is

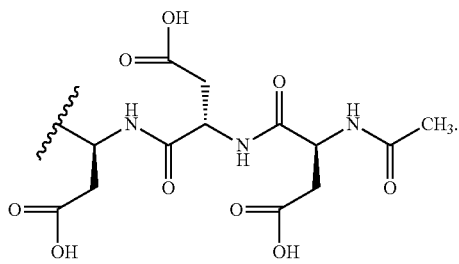

17. The method of claim 1, wherein the compound of formula (I) is selected from the group consisting of:
2,2,2-trichloroethyl 6-(4-((8-benzyl-3-oxo-6-phenyl-3,7-dihydroimidazo[1,2-a]pyrazin-2-yl)methyl)-2-chlorophenoxy)hexane-1-sulfonate;
tert-butyl 6-(3-((8-benzyl-3-oxo-6-phenyl-3,7-dihydroimidazo[1,2-a]pyrazin-2-yl)methyl)phenoxy)hexanoate;
6-(3-((8-benzyl-3-oxo-6-phenyl-3,7-dihydroimidazo[1,2-a]pyrazin-2-yl)methyl)phenoxy)hexanoic acid;
8-benzyl-2-(3-((6-bromohexyl)oxy)benzyl)-6-phenylimidazo[1,2-a]pyrazin-3(7H)-one;
sodium 6-(3-((8-benzyl-3-oxo-6-phenyl-3,7-dihydroimidazo[1,2-a]pyrazin-2-yl)methyl)phenoxy)hexane-1-sulfonate;
tert-butyl 4-(3-((8-benzyl-3-oxo-6-phenyl-3,7-dihydroimidazo[1,2-a]pyrazin-2-yl)methyl)phenoxy)butanoate;
sodium 3-(3-((8-benzyl-3-oxo-6-phenyl-3,7-dihydroimidazo[1,2-a]pyrazin-2-yl)methyl)phenoxy)propane-1-sulfonate;
4-(3-((8-benzyl-3-oxo-6-phenyl-3,7-dihydroimidazo[1,2-a]pyrazin-2-yl)methyl)phenoxy)butanoic acid;
tert-butyl 8-(3-((8-benzyl-3-oxo-6-phenyl-3,7-dihydroimidazo[1,2-a]pyrazin-2-yl)methyl)phenoxy)octanoate;
8-benzyl-2-(4-((6-bromohexyl)oxy)-3-chlorobenzyl)-6-phenylimidazo[1,2-a]pyrazin-3(7H)-one;
8-(3-((8-benzyl-3-oxo-6-phenyl-3,7-dihydroimidazo[1,2-a]pyrazin-2-yl)methyl)phenoxy)octanoic acid;
tert-butyl 6-(4-((8-benzyl-3-oxo-6-phenyl-3,7-dihydroimidazo[1,2-a]pyrazin-2-yl)methyl)-2-chlorophenoxy)hexanoate;
6-(4-((8-benzyl-3-oxo-6-phenyl-3,7-dihydroimidazo[1,2-a]pyrazin-2-yl)methyl)-2-chlorophenoxy)hexanoic acid;
sodium 6-(4-((8-benzyl-3-oxo-6-phenyl-3,7-dihydroimidazo[1,2-a]pyrazin-2-yl)methyl)-2-chlorophenoxy hexane-1-sulfonate;
(S)-3-acetamido-4-(((S)-1-(((S)-1-((6-(3-((8-benzyl-3-oxo-6-phenyl-3,7-dihydroimidazo[1,2-a]pyrazin-2-yl)methyl)phenoxy)hexyl)amino)-3-carboxy-1-oxopropan-2-yl)amino)-3-carboxy-1-oxopropan-2-yl)amino)-4-oxobutanoic acid;
sodium 8-(4-((8-benzyl-3-oxo-6-phenyl-3,7-dihydroimidazo[1,2-a]pyrazin-2-yl)methyl)-2-chlorophenoxy)octane-1-sulfonate;
sodium 10-(4-((8-benzyl-3-oxo-6-phenyl-3,7-dihydroimidazo[1,2-a]pyrazin-2-yl)methyl)-2-chlorophenoxy)decane-1-sulfonate;
sodium 6-(5-((8-benzyl-3-oxo-6-phenyl-3,7-dihydroimidazo[1,2-a]pyrazin-2-yl)methyl)-2-chlorophenoxy)hexane-1-sulfonate;
sodium 6-(4-((8-benzyl-3-oxo-6-phenyl-3,7-dihydroimidazo[1,2-a]pyrazin-2-yl)methyl)-2-fluorophenoxy)hexane-1-sulfonate;
sodium 6-(4-((8-benzyl-3-oxo-6-phenyl-3,7-dihydroimidazo[1,2-a]pyrazin-2-yl)methyl)-2,6-difluorophenoxy)hexane-1-sulfonate;
2-(4-((6-aminohexyl)oxy)-3-fluorobenzyl)-8-benzyl-6-phenylimidazo[1,2-a]pyrazin-3(7H)-one;
6-(4-((8-benzyl-6-(3-hydroxyphenyl)-3-oxo-3,7-dihydroimidazo[1,2-a]pyrazin-2-yl)methyl)-2-chlorophenoxy)hexane-1-sulfonic acid; and
(S)-3-acetamido-4-(((S)-1-(((S)-1-((6-(4-((8-benzyl-3-oxo-6-phenyl-3,7-dihydroimidazo[1,2-a]pyrazin-2-yl)methyl)-2-fluorophenoxy)hexyl)amino)-3-carboxy-1-oxopropan-2-yl)amino)-3-carboxy-1-oxopropan-2-yl)amino)-4-oxobutanoic acid.

18. The method of claim 1, wherein the protein comprising a coelenterazine-utilizing luciferase enzyme is a fusion protein in which a coelenterazine-utilizing luciferase enzyme is fused to a cell surface protein.

19. A method for monitoring an exocytotic event in a cell, comprising:
(a) contacting the cell with a compound of formula (I):

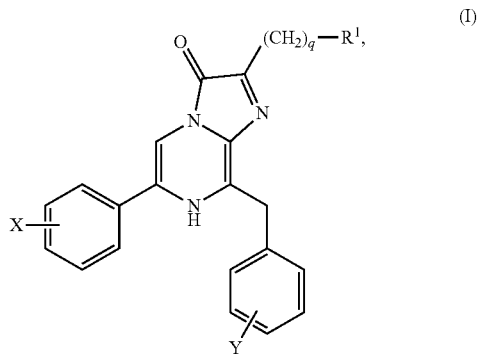

or a tautomer, or a pharmaceutically acceptable salt thereof, wherein

X and Y are independently absent, hydroxy, amino, —COOR$^2$, —SO$_2$—OR$^3$, —PO (OR$^4$)(OR$^5$), or —O—(CR$^{1a}$R$^{1b}$)$_m$—Z;

R$^1$ is optionally substituted aryl, optionally substituted heteroaryl, optionally substituted heterocycle, or optionally substituted cycloalkyl, wherein R$^1$ is substituted at least with -Q-L-Z;

Z at each occurrence is independently —COOR$^2$, —SO$_2$—OR$^3$, —PO (OR$^4$)(OR$^5$), halogen, —NR$^6$R$^7$, or —NR$^8$—CO—R$^9$;

Q is —O—, —NR$^Q$—, —NR$^Q$—CO—, —CO—NR$^Q$—, —O—CO—NR$^Q$—, or —NR$^Q$—CO—O—;

L is —(CR$^{1a}$R$^{1b}$)$_m$— or —(CR$^{1x}$R$^{1y}$—CR$^{1x}$R$^{1y}$—O)$_{t1}$—(CR$^{1x}$R$^{1y}$)$_{t2}$-Q$^1$-, wherein Q$^1$ is absent, —O—, or —NR$^{Q1}$—;

R$^2$, R$^3$, R$^4$, R$^5$, R$^8$, and R$^9$ at each occurrence are independently hydrogen, optionally substituted C$_1$-C$_8$ alkyl, optionally substituted aryl, optionally substituted cycloalkyl, optionally substituted heteroaryl, or optionally substituted heterocycle;

R$^6$ and R$^7$ at each occurrence are independently hydrogen, optionally substituted C$_1$-C$_8$ alkyl, optionally substituted aryl, optionally substituted cycloalkyl, optionally substituted heteroaryl, or optionally substituted heterocycle; or R$^6$ and R$^7$, together with the nitrogen atom to which they are attached, together form an optionally substituted ring;

R$^{1a}$, R$^{1b}$, R$^Q$, R$^{Q1}$, R$^{1x}$, and R$^{1y}$ at each occurrence are independently hydrogen, C$_1$-C$_4$ alkyl, or C$_1$-C$_4$ haloalkyl;

q is 0, 1, or 2;

m at each occurrence is independently 1-12;

t1 is 1-10; and t2 is 0-5, and (b) detecting luminescence on the cell surface;

wherein the cell expresses a protein comprising a coelenterazine-utilizing luciferase enzyme that is secreted from the cell.

20. The method of claim 19, wherein
Q is —O—, —NH—, —NH—CO—, —CO—NH—, —O—CO—NH—, or —NH—CO—O—; and
L is —(CR$^{1a}$R$^{1b}$)$_m$—.

21. The method of claim 19, wherein
Q is —O—; and
L is —(CR$^{1a}$R$^{1b}$)$_m$—.

22. The method of claim 19 wherein
L is —(CR$^{1x}$R$^{1y}$—CR$^{1x}$R$^{1y}$—O)$_{t1}$—(CR$^{1x}$R$^{1y}$)$_{t2}$-Q$^1$-.

23. The method of claim 19, wherein R$^1$ is phenyl or furyl optionally further substituted with 1, 2, 3, or 4 substituents, each independently selected from the group consisting of halogen, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, aryloxy, phenoxy, benzyloxy, amino, alkylamino, dialkylamino, acylamino, aminoalkyl, arylamino, sulfonylamino, sulfinylamino, alkylsulfonyl, arylsulfonyl, aminosulfonyl, —COOH, ketone, amide, carbamate, silyl, substituted silyl, t-butyldimethylsilyl, alkylsulfanyl, sulfanyl, and acyl.

24. The method of claim 19, wherein R$^1$ is phenyl or furyl substituted with -Q-L-Z, in which Q is —O— and L is —(CR$^{1a}$R$^{1b}$)$_m$—.

25. The method of claim 19, wherein q is 1.

26. The method of claim 19, wherein the compound of formula (I) is a compound of formula (I-a):

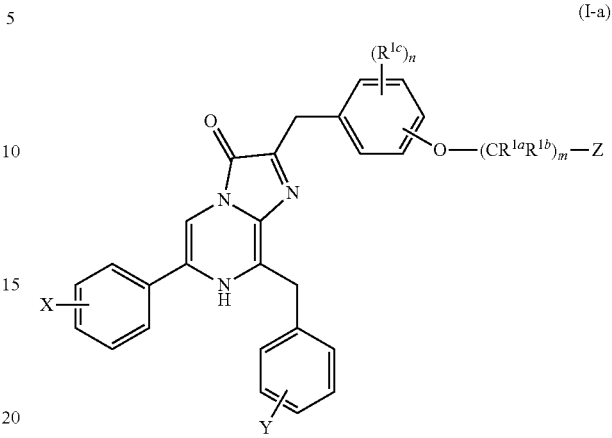

(I-a)

or a tautomer, or a pharmaceutically acceptable salt thereof, wherein

R$^{1c}$ is selected from the group consisting of alkyl, halogen, cyano, nitro, haloalkyl, hydroxy, hydroxyalkyl, amino, and —COOH;

n is 0, 1, 2, 3, or 4; and

X, Y, R$^{1a}$, R$^{1b}$, m, and Z are as defined in claim 19.

27. The method of claim 26, wherein at least one of X and Y is absent.

28. The method of claim 26, wherein both X and Y are absent.

29. The method of claim 26, wherein n is 0.

30. The method of claim 26, wherein n is 1 or 2, and each R$^{1c}$ is independently halogen.

31. The method of claim 26, wherein m is 3, 4, 5, 6, 7, 8, 9, or 10.

32. The method of claim 26, wherein Z is —COOR$^2$, —SO$_2$—OR$^3$, or —PO(OR$^4$)(OR$^5$), or a pharmaceutically acceptable salt thereof.

33. The method of claim 26, wherein:
Z is —NR$^6$R$^7$ or —NR$^8$—CO—R$^9$, or a pharmaceutically acceptable salt thereof;
R$^9$ is —(CR$^{9a}$R$^{9b}$—NH—CO)$_u$—R$^{10}$;
R$^{9a}$ and R$^{9b}$ at each occurrence are independently hydrogen or C$_1$-C$_4$ alkyl optionally substituted with —COOR$^{9c}$;
R$^{9c}$ at each occurrence is independently hydrogen or C$_1$-C$_4$ alkyl;
R$^{10}$ is optionally substituted C$_1$-C$_8$ alkyl; and
u is 0-10.

34. The method of claim 26, wherein:
Z is —NR$^8$—CO—R$^9$, or a pharmaceutically acceptable salt thereof;
R$^8$ is hydrogen; and
R$^9$ is

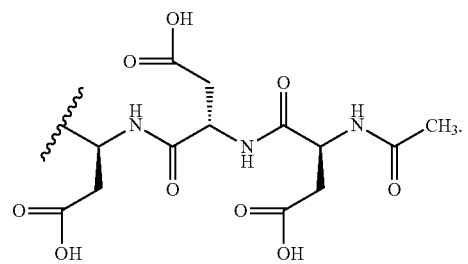 [SMILES: *[C@H](CC(=O)O)NC(=O)[C@H](CC(=O)O)NC(=O)[C@H](CC(=O)O)NC(C)=O]

35. The method of claim 19, wherein the compound of formula (I) is selected from the group consisting of:

- 2,2,2-trichloroethyl 6-(4-((8-benzyl-3-oxo-6-phenyl-3,7-dihydroimidazo[1,2-a]pyrazin-2-yl)methyl)-2-chlorophenoxy)hexane-1-sulfonate;
- tert-butyl 6-(3-((8-benzyl-3-oxo-6-phenyl-3,7-dihydroimidazo[1,2-a]pyrazin-2-yl)methyl)phenoxy)hexanoate;
- 6-(3-((8-benzyl-3-oxo-6-phenyl-3,7-dihydroimidazo[1,2-a]pyrazin-2-yl)methyl)phenoxy)hexanoic acid;
- 8-benzyl-2-(3-((6-bromohexyl)oxy)benzyl)-6-phenylimidazo[1,2-a]pyrazin-3(7H)-one;
- sodium 6-(3-((8-benzyl-3-oxo-6-phenyl-3,7-dihydroimidazo[1,2-a]pyrazin-2-yl)methyl)phenoxy)hexane-1-sulfonate;
- tert-butyl 4-(3-((8-benzyl-3-oxo-6-phenyl-3,7-dihydroimidazo[1,2-a]pyrazin-2-yl)methyl)phenoxy)butanoate;
- sodium 3-(3-((8-benzyl-3-oxo-6-phenyl-3,7-dihydroimidazo[1,2-a]pyrazin-2-yl)methyl)phenoxy)propane-1-sulfonate;
- 4-(3-((8-benzyl-3-oxo-6-phenyl-3,7-dihydroimidazo[1,2-a]pyrazin-2-yl)methyl)phenoxy)butanoic acid;
- tert-butyl 8-(3-((8-benzyl-3-oxo-6-phenyl-3,7-dihydroimidazo[1,2-a]pyrazin-2-yl)methyl)phenoxy)octanoate;
- 8-benzyl-2-(4-((6-bromohexyl)oxy)-3-chlorobenzyl)-6-phenylimidazo[1,2-a]pyrazin-3(7H)-one;
- 8-(3-((8-benzyl-3-oxo-6-phenyl-3,7-dihydroimidazo[1,2-a]pyrazin-2-yl)methyl)phenoxy)octanoic acid;
- tert-butyl 6-(4-((8-benzyl-3-oxo-6-phenyl-3,7-dihydroimidazo[1,2-a]pyrazin-2-yl)methyl)-2-chlorophenoxy)hexanoate;
- 6-(4-((8-benzyl-3-oxo-6-phenyl-3,7-dihydroimidazo[1,2-a]pyrazin-2-yl)methyl)-2-chlorophenoxy)hexanoic acid;
- sodium 6-(4-((8-benzyl-3-oxo-6-phenyl-3,7-dihydroimidazo[1,2-a]pyrazin-2-yl)methyl)-2-chlorophenoxy)hexane-1-sulfonate;
- (S)-3-acetamido-4-(((S)-1-(((S)-1-((6-(3-((8-benzyl-3-oxo-6-phenyl-3,7-dihydroimidazo[1,2-a]pyrazin-2-yl)methyl)phenoxy)hexyl)amino)-3-carboxy-1-oxopropan-2-yl)amino)-3-carboxy-1-oxopropan-2-yl)amino)-4-oxobutanoic acid;
- sodium 8-(4-((8-benzyl-3-oxo-6-phenyl-3,7-dihydroimidazo[1,2-a]pyrazin-2-yl)methyl)-2-chlorophenoxy)octane-1-sulfonate;
- sodium 10-(4-((8-benzyl-3-oxo-6-phenyl-3,7-dihydroimidazo[1,2-a]pyrazin-2-yl)methyl)-2-chlorophenoxy)decane-1-sulfonate;
- sodium 6-(5-((8-benzyl-3-oxo-6-phenyl-3,7-dihydroimidazo[1,2-a]pyrazin-2-yl)methyl)-2-chlorophenoxy)hexane-1-sulfonate;
- sodium 6-(4-((8-benzyl-3-oxo-6-phenyl-3,7-dihydroimidazo[1,2-a]pyrazin-2-yl)methyl)-2-fluorophenoxy)hexane-1-sulfonate;
- sodium 6-(4-((8-benzyl-3-oxo-6-phenyl-3,7-dihydroimidazo[1,2-a]pyrazin-2-yl)methyl)-2,6-difluorophenoxy)hexane-1-sulfonate;
- 2-(4-((6-aminohexyl)oxy)-3-fluorobenzyl)-8-benzyl-6-phenylimidazo[1,2-a]pyrazin-3(7H)-one;
- 6-(4-((8-benzyl-6-(3-hydroxyphenyl)-3-oxo-3,7-dihydroimidazo[1,2-a]pyrazin-2-yl)methyl)-2-chlorophenoxy)hexane-1-sulfonic acid; and
- (S)-3-acetamido-4-(((S)-1-(((S)-1-((6-(4-((8-benzyl-3-oxo-6-phenyl-3,7-dihydroimidazo[1,2-a]pyrazin-2-yl)methyl)-2-fluorophenoxy)hexyl)amino)-3-carboxy-1-oxopropan-2-yl)amino)-3-carboxy-1-oxopropan-2-yl)amino)-4-oxobutanoic acid.

36. The method of claim 19, wherein the exocytotic event is receptor recycling, and the protein comprising a coelenterazine-utilizing luciferase enzyme is a fusion protein in which a coelenterazine-utilizing luciferase enzyme is fused to a cell surface receptor.

\* \* \* \* \*